(12) United States Patent
Xiong et al.

(10) Patent No.: US 11,725,009 B2
(45) Date of Patent: *Aug. 15, 2023

(54) ANTI-INFLUENZA VIRUS PYRIMIDINE DERIVATIVE

(71) Applicant: GUANGDONG RAYNOVENT BIOTECH CO., LTD., Guangzhou (CN)

(72) Inventors: Jian Xiong, Shanghai (CN); Chaofeng Long, Guangzhou (CN); Jingjing Wang, Shanghai (CN); Xiaoxin Chen, Guangzhou (CN); Kevin X Chen, Shanghai (CN); Cheng Xie, Shanghai (CN); Peng Li, Shanghai (CN); Xuanjia Peng, Shanghai (CN); Jian Li, Shanghai (CN); Shuhui Chen, Shanghai (CN)

(73) Assignee: GUANGDONG RAYNOVENT BIOTECH CO., LTD., Guangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/410,801

(22) Filed: Aug. 24, 2021

(65) Prior Publication Data

US 2022/0135558 A1    May 5, 2022

Related U.S. Application Data

(62) Division of application No. 16/330,353, filed as application No. PCT/CN2017/100461 on Sep. 5, 2017, now Pat. No. 11,136,319.

(30) Foreign Application Priority Data

Sep. 5, 2016 (CN) .......................... 201610804101.3
Dec. 28, 2016 (CN) .......................... 201611238759.9

(51) Int. Cl.
  A61K 31/506  (2006.01)
  A61P 31/16   (2006.01)
  C07D 471/04  (2006.01)

(52) U.S. Cl.
  CPC .......... C07D 471/04 (2013.01); A61K 31/506 (2013.01); A61P 31/16 (2018.01); *C07B 2200/07* (2013.01)

(58) Field of Classification Search
  CPC .............................. A61K 31/506; A61P 31/16
  See application file for complete search history.

(56) References Cited

U.S. PATENT DOCUMENTS

| | | | |
|---|---|---|---|
| 11,136,319 B2 * | 10/2021 | Xiong | A61P 31/16 |
| 11,535,613 B2 * | 12/2022 | Xiong | C07D 471/04 |
| 2020/0407354 A1 * | 12/2020 | Xiong | C07D 471/04 |

FOREIGN PATENT DOCUMENTS

| | | |
|---|---|---|
| CN | 103492381 A | 1/2014 |
| CN | 104922128 A | 9/2015 |
| CN | 201610804101.3 | 9/2016 |
| CN | 201611238759.9 | 12/2016 |
| WO | 2010148197 A1 | 12/2010 |
| WO | 2012083117 A1 | 6/2012 |
| WO | 2016020526 A1 | 2/2016 |
| WO | 2017097234 A1 | 6/2017 |
| WO | 2017133670 A1 | 8/2017 |
| WO | 2018033082 A1 | 2/2018 |

OTHER PUBLICATIONS

International Search Report dated Dec. 11, 2017 issued for related PCT patent app. No. PCT/CN2017/100461.
Berge et al., "Pharmaceutical Salts", Journal of Pharmaceutical Science 66: 1-19 (1977).
Remington: The Science and Practice of Pharmacy, 21st Ed., Lippincott, Williams & Wilkins (2005), Philip P. Gerbino, Article 71.
Communication pursuant to Article 94(3) EPC issued by European Patent Office dated Jan. 13, 2021 for related EP Patent App. No. 17845565.5.

* cited by examiner

*Primary Examiner* — Laura L Stockton
(74) *Attorney, Agent, or Firm* — D'Ambrosio & Menon, PLLC; Usha Menon

(57) ABSTRACT

The present invention discloses a class of anti-influenza virus compounds, and the use thereof in the preparation of a drug for treating diseases associated with influenza viruses. In particular, the present invention discloses a compound represented by formula (I) and a pharmaceutically acceptable salt thereof.

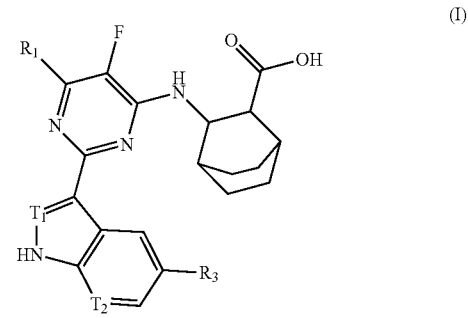

17 Claims, No Drawings

ANTI-INFLUENZA VIRUS PYRIMIDINE DERIVATIVE

CROSS-REFERENCE TO RELATED APPLICATIONS

This application is a divisional of U.S. patent application Ser. No. 16/330,353 filed Mar. 4, 2019, which is a 35 U.S.C. 371 National Stage filing of PCT/CN2017/100461 filed Sep. 5, 2017, which claims priority under 35 U.S.C. 119 from the People's Republic of China Application No. 201610804101.3 filed Sep. 5, 2016, and China Application No. 201611238759.9 filed Dec. 28, 2016, the contents of each of which are herein by incorporated by reference in their entirety.

TECHNICAL FIELD

The present invention relates to a class of anti-influenza virus compounds, and the use thereof in the preparation of a drug for treating diseases associated with influenza viruses. In particular, the present invention relates to a compound represented by formula (I) and a pharmaceutically acceptable salt thereof.

BACKGROUND

Epidemic influenza virus, that is influenza virus (IFV), is a segmented single-strand antisense RNA virus capable of causing influenza in human and animals. Pandemic influenza results in thousands of deaths, causing great social panic and increasing the risks of social instability.

Influenza would bring forth direct costs due to loss of productivity and related medical resources as well as indirect costs on preventive measures. In U.S., influenza causes a loss of approximate 10 billion dollars accumulatively each year, it is estimated that pandemic influenza in future may cause direct and indirect costs of hundreds of billion dollars. The prevention cost would also be very high, governments around the world have spent billions of dollars on preparing for the possible H5N1 avian influenza pandemic, with the costs being related to the purchase of medicines and vaccines as well as the strategies of developing the disaster exercising and enhancing the border control.

Currently, therapeutic options for influenza include vaccination and chemical therapy and chemical prevention with antiviral drugs. Antiviral drugs may also be used to treat influenza, wherein neuraminidase inhibitors, such as Oseltamivir (Tamiflu), have obvious effects on influenza A virus, while upon clinical observation, it was found that there have been virus strains resistant to such type of neuraminidase inhibitors. In the field of anti-influenza virus, it is urgently needed clinically an anti-influenza virus drug with a novel action mechanism, which is capable of treating influenza A with a single drug, or being used for the prevention and treatment of influenza A in combination with the marketed anti-influenza virus drugs with other action mechanisms.

Wherein, WO2010148197 reported the following compound:

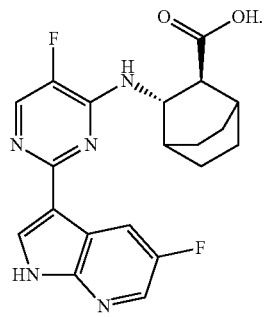 [SMILES: O=C(O)[C@H]1C2CCC(CC2)[C@@H]1Nc1nc(-c2c[nH]c3ncc(F)cc23)ncc1F]

SUMMARY OF THE INVENTION

The present invention provides a compound of formula (I) or a pharmaceutically acceptable salt thereof,

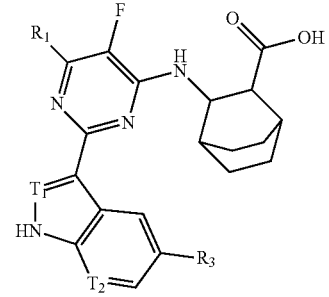

wherein, $R_1$ is selected from the group consisting of: $C_{1-6}$ alkylthio, 5-6 membered heteroaryl, $C_{2-6}$ alkynyl, $C_{3-6}$ cycloalkyl which are optionally substituted with 1, 2 or 3 R or R';

$T_1$ is selected from the group consisting of N or CH;

$T_2$ is selected from the group consisting of N or C($R_2$);

$R_2$ is selected from the group consisting of H, F, Cl, Br, I;

$R_3$ is selected from the group consisting of H, halogen, CN, $NH_2$, OH, or selected from the group consisting of: $C_{1-6}$ alkyl which is optionally substituted with 1, 2 or 3 R or R';

R is selected from the group consisting of halogen, OH, $NH_2$, CN, COOH,

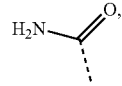

or selected from the group consisting of: $C_{1-6}$ alkyl, $C_{1-6}$ heteroalkyl, $C_{3-6}$ cycloalkyl, 3-6 membered heterocycloalkyl, 3-6 membered heterocycloalkyl-C(=O)—, 3-6 membered heterocycloalkyl-$(CH_2)_{1-3}$— which are optionally substituted with 1, 2 or 3 R';

R' is selected from the group consisting of: F, Cl, Br, I, CN, OH, $NH_2$, COOH, Me, $NHCH_3$, $N(CH_3)_2$,

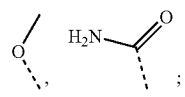

"hetero-" in the 5-6 membered heteroaryl, $C_{1-6}$ heteroalkyl, $C_{3-6}$ cycloalkyl, 3-6 membered heterocycloalkyl is selected from the group consisting of: N, —S—, —O—, —NH—;

in any one of the aforesaid cases, the number of heteroatoms or heteroatomic groups is each independently selected from the group consisting of 1, 2 or 3.

In some embodiments of the present invention, the aforesaid R is selected from the group consisting of: F, Cl, Br, I, OH, $NH_2$, CN, COOH,

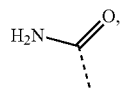

or selected from the group consisting of: $C_{1-3}$ alkyl, $C_{1-3}$ heteroalkyl, $C_{3-6}$ cycloalkyl, 3-6 membered heterocycloalkyl, 3-6 membered heterocycloalkyl-C(=O)—, 3-6 membered heterocycloalkyl-$CH_2$— which are optionally substituted with 1, 2 or 3 R'.

In some embodiments of the present invention, the aforesaid R is selected from the group consisting of: F, Cl, Br, I, OH, $NH_2$, CN, COOH,

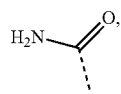

or selected from the group consisting of: Me, Et, $C_{1-3}$ alkylthio, $C_{3-6}$ cycloalkyl, azetidinyl, pyrrolidinyl, piperazinyl, morpholinyl, piperazinyl-C(=O)—, morpholinyl-C(=O)—, pyrrolidinyl-C(=O)—, piperazinyl-$CH_2$—, morpholinyl-$CH_2$—, pyrrolidinyl-$CH_2$— which are optionally substituted with 1, 2 or 3 R'.

In some embodiments of the present invention, the aforesaid R is selected from the group consisting of: F, Cl, Br, I, OH, $NH_2$, CN, COOH,

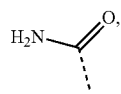

or selected from the group consisting of: Me, Et,

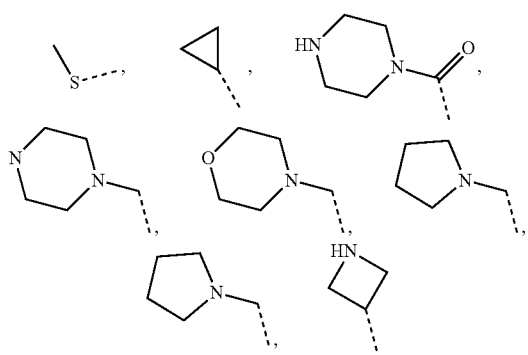

which are optionally substituted with 1, 2 or 3 R'.

In some embodiments of the present invention, the aforesaid R is selected from the group consisting of: F, Cl, Br, I, OH, $NH_2$, Me, Et, CN, COOH,

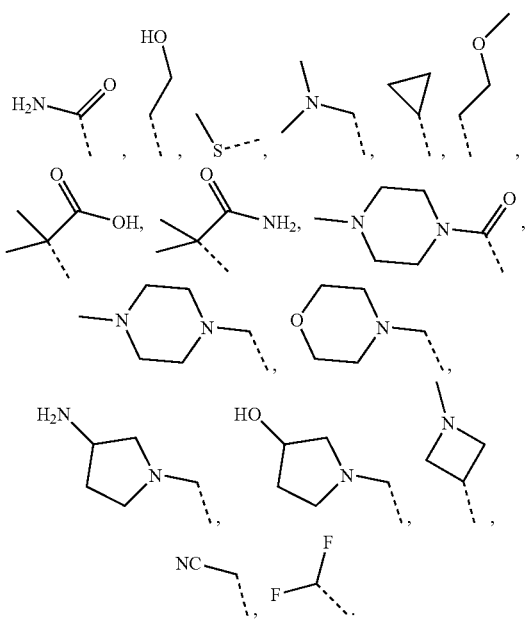

In some embodiments of the present invention, the aforesaid $R_1$ is selected from the group consisting of: $C_{1-3}$ alkylthio, $C_{2-4}$ alkynyl, $C_{3-5}$ cycloalkyl which are optionally substituted with 1, 2 or 3 R or R'.

In some embodiments of the present invention, the aforesaid $R_1$ is selected from the group consisting of:

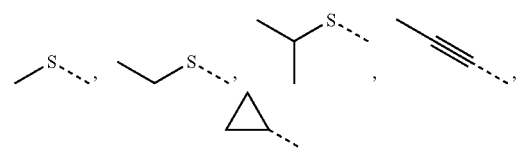

which are optionally substituted with 1, 2 or 3 R or R'.

In some embodiments of the present invention, the aforesaid $R_1$ is selected from the group consisting of:

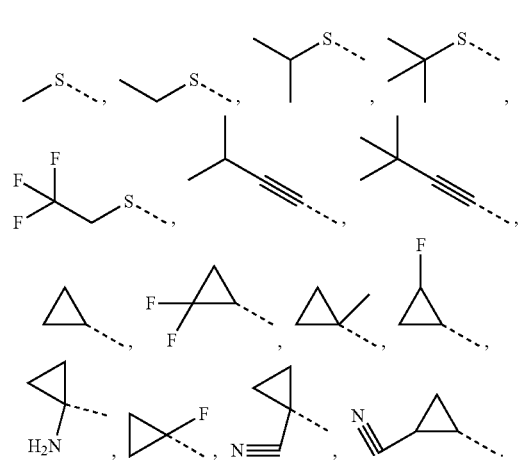

In some embodiments of the present invention, the aforesaid $R_1$ is selected from the group consisting of: pyridyl, pyrazolyl, imidazolyl, thienyl, oxazolyl, isoxazolyl which are optionally substituted with 1, 2 or 3 R or R'.

In some embodiments of the present invention, the aforesaid $R_1$ is selected from the group consisting of:

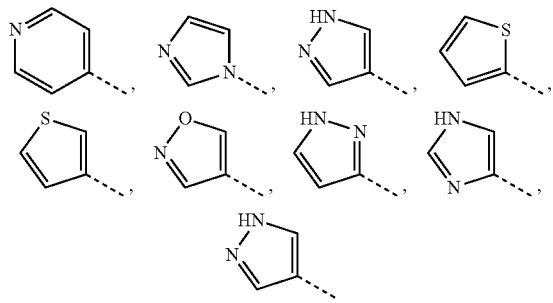

which are optionally substituted with 1, 2 or 3 R or R'.

In some embodiments of the present invention, the aforesaid $R_1$ is selected from the group consisting of:

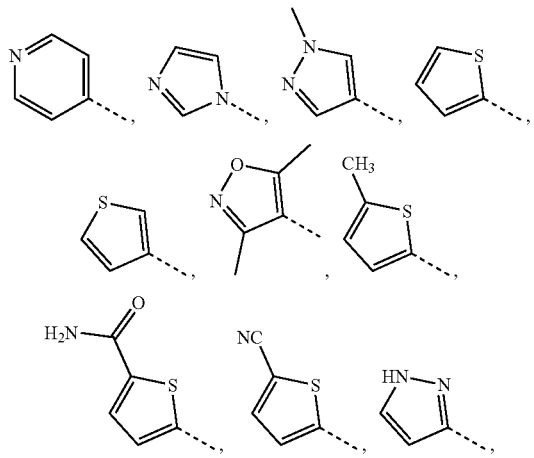

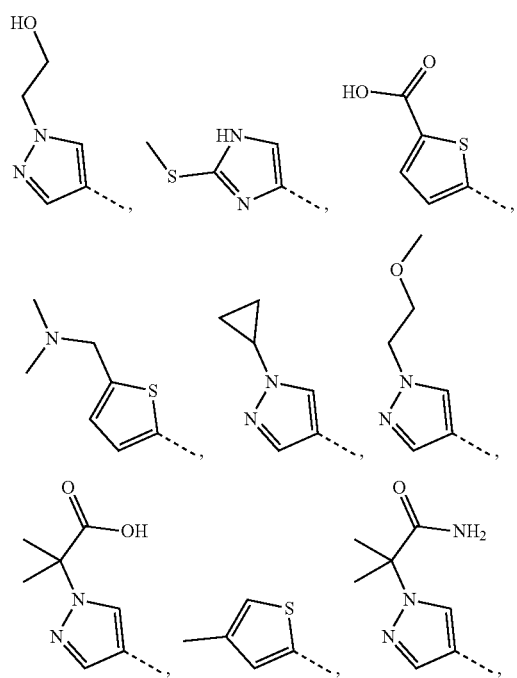

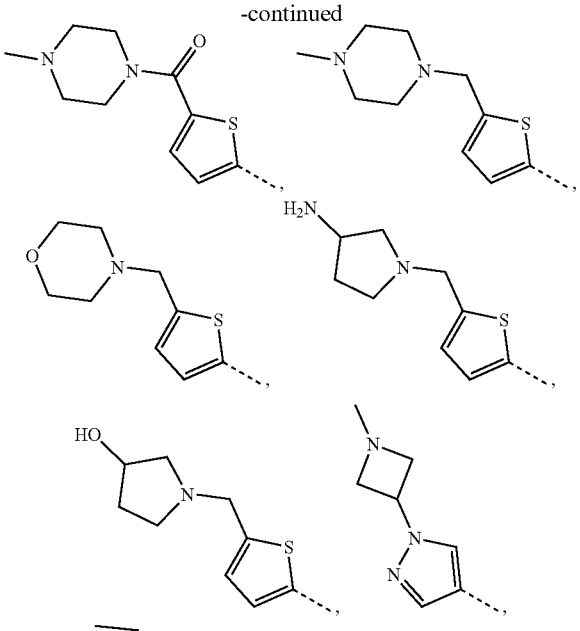

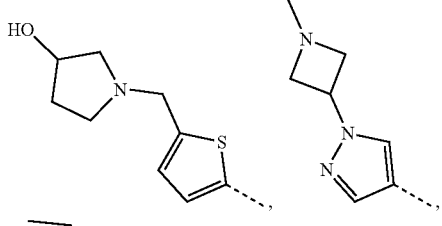

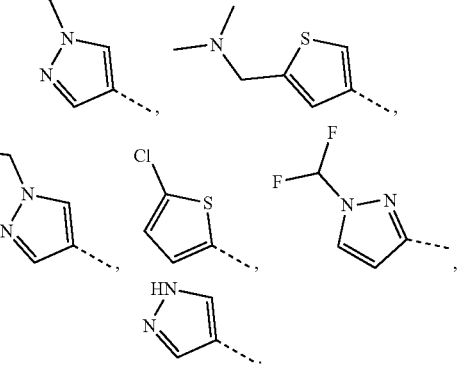

In some embodiments of the present invention, the aforesaid $R_1$ is selected from the group consisting of:

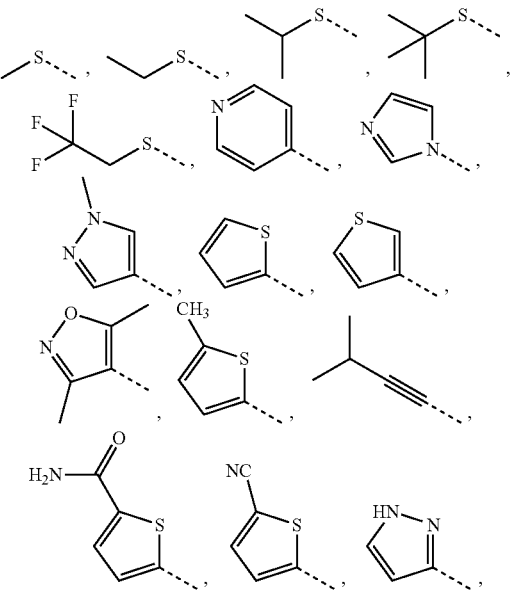

-continued

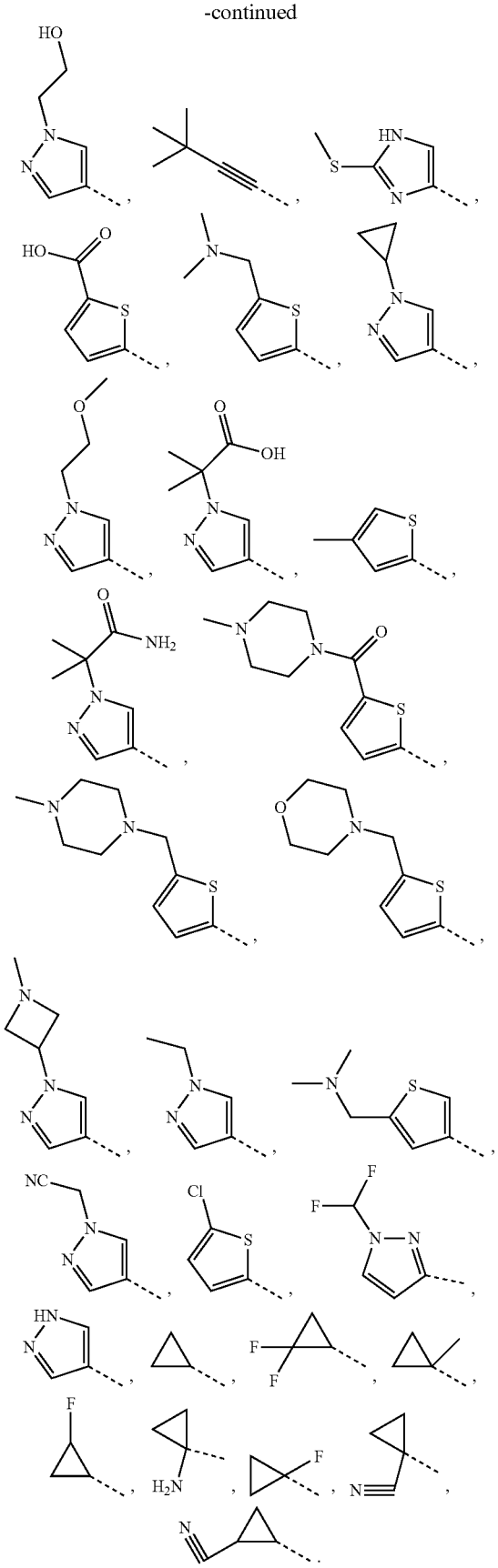

In some embodiments of the present invention, the aforesaid $T_2$ is selected from the group consisting of: N, CH or C(F).

In some embodiments of the present invention, the aforesaid $R_3$ is selected from the group consisting of H, halogen, CN, $NH_2$, OH, or selected from the group consisting of: $C_{1-3}$ alkyl which is optionally substituted with 1, 2 or 3 R or R'.

In some embodiments of the present invention, the aforesaid $R_3$ is selected from the group consisting of H, F, Cl, Br, I, CN, $NH_2$, OH, or selected from the group consisting of: Me, Et which are optionally substituted with 1, 2 or 3 R or R'.

In some embodiments of the present invention, the aforesaid $R_3$ is selected from the group consisting of H, F, Cl, Br, I, CN, $NH_2$, OH, Me, Et, $CF_3$.

In some embodiments of the present invention, the aforesaid structural unit

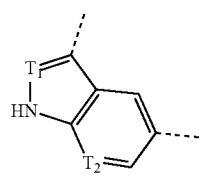

is selected from the group consisting of

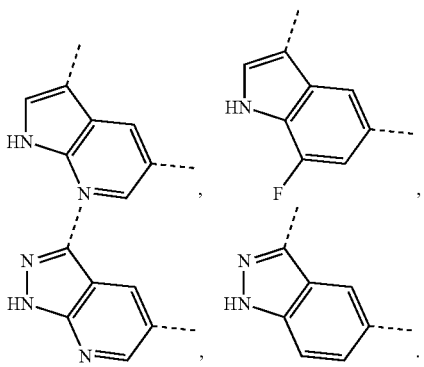

In some embodiments of the present invention, the aforesaid R is selected from the group consisting of: F, Cl, Br, I, OH, $NH_2$, CN, COOH,

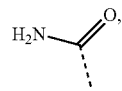

or selected from the group consisting of: $C_{1-3}$ alkyl, $C_{1-3}$ heteroalkyl, $C_{3-6}$ cycloalkyl, 3-6 membered heterocycloalkyl, 3-6 membered heterocycloalkyl-C(=O)—, 3-6 membered heterocycloalkyl-$CH_2$— which are optionally substituted with 1, 2 or 3 R', and other variables are as defined above.

In some embodiments of the present invention, the aforesaid R is selected from the group consisting of: F, Cl, Br, I, OH, $NH_2$, CN, COOH,

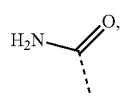

or selected from the group consisting of: Me, Et, C$_{1-3}$ alkylthio, C$_{3-6}$ cycloalkyl, azetidinyl, pyrrolidinyl, piperazinyl, morpholinyl, piperazinyl-C(=O)—, morpholinyl-C(=O)—, pyrrolidinyl-C(=O)—, piperazinyl-CH$_2$—, morpholinyl-CH$_2$—, pyrrolidinyl-CH$_2$— which are optionally substituted with 1, 2 or 3 R', and other variables are as defined above.

In some embodiments of the present invention, the aforesaid R is selected from the group consisting of: F, Cl, Br, I, OH, NH$_2$, CN, COOH,

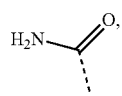

or selected from the group consisting of: Me, Et,

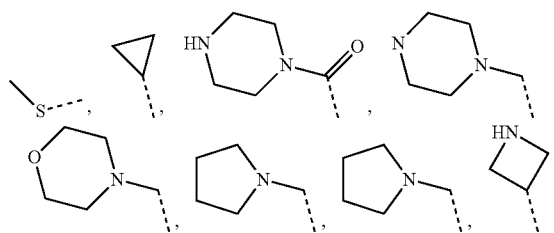

which are optionally substituted with 1, 2 or 3 R', and other variables are as defined above.

In some embodiments of the present invention, the aforesaid R is selected from the group consisting of: F, Cl, Br, I, OH, NH$_2$, Me, Et, CN, COOH,

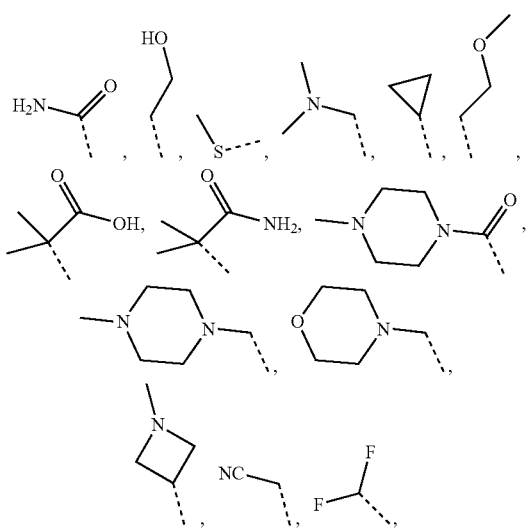

and other variables are as defined above.

In some embodiments of the present invention, the aforesaid R$_1$ is selected from the group consisting of: C$_{1-3}$ alkylthio, C$_{2-4}$ alkynyl, C$_{3-5}$ cycloalkyl which are optionally substituted with 1, 2 or 3 R or R', and other variables are as defined above.

In some embodiments of the resent invention, the aforesaid R$_1$ is selected from the group consisting of:

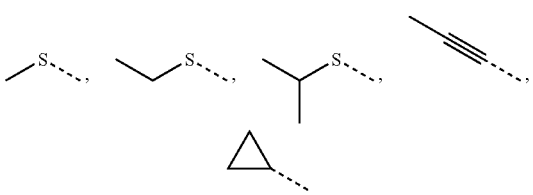

which are optionally substituted with 1, 2 or 3 R or R', and other variables are as defined above.

In some embodiments of the present invention, the aforesaid R$_1$ is selected from the group consisting of:

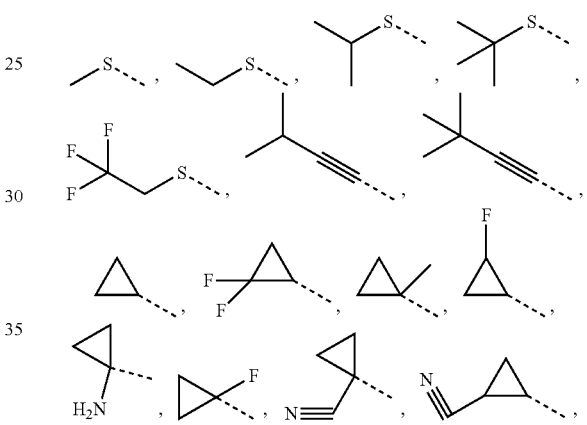

and other variables are as defined above.

In some embodiments of the present invention, the aforesaid R$_1$ is selected from the group consisting of: pyridyl, pyrazolyl, imidazolyl, thienyl, oxazolyl, isoxazolyl which are optionally substituted with 1, 2 or 3 R or R', and other variables are as defined above.

In some embodiments of the present invention, the aforesaid R$_1$ is selected from the group consisting of:

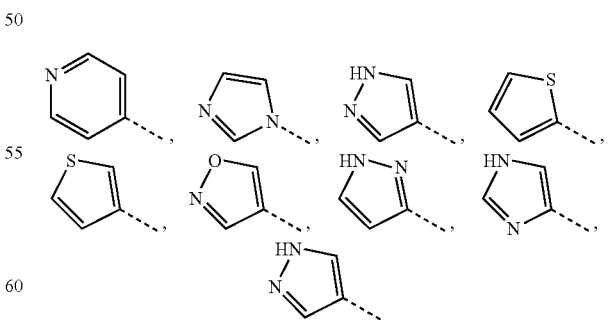

which are optionally substituted with 1, 2 or 3 R or R', and other variables are as defined above.

In some embodiments of the present invention, the aforesaid R$_1$ is selected from the group consisting of:

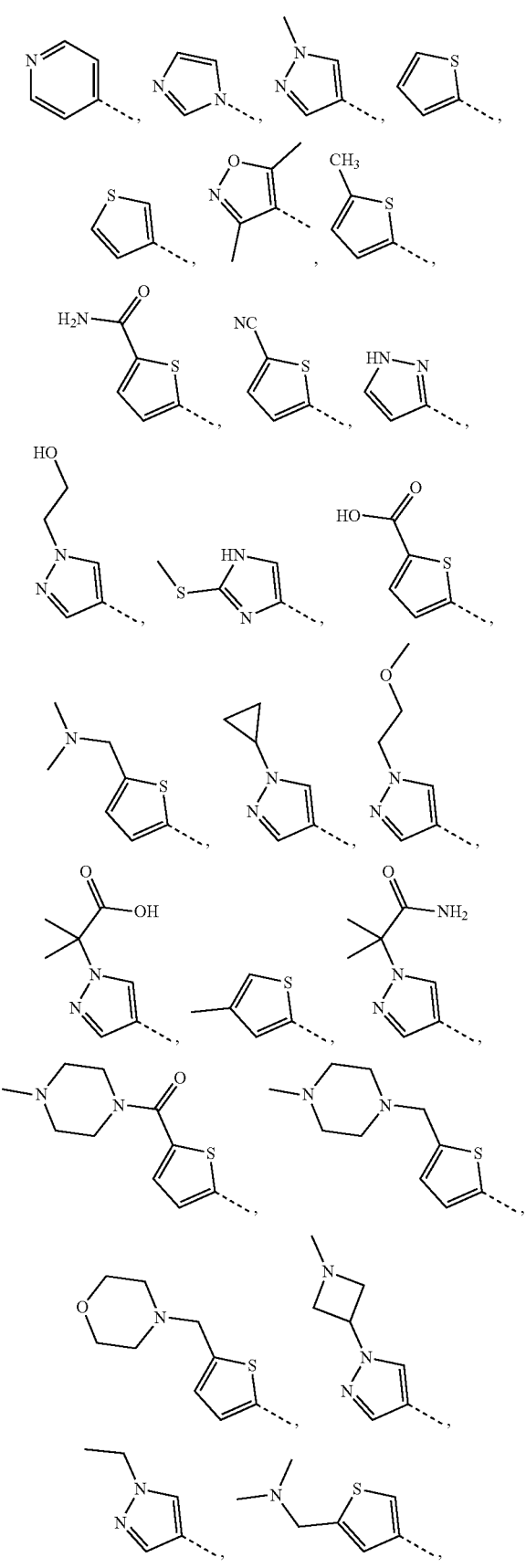
and other variables are as defined above.
In some embodiments of the present invention, the aforesaid $R_1$ is selected from the group consisting of:
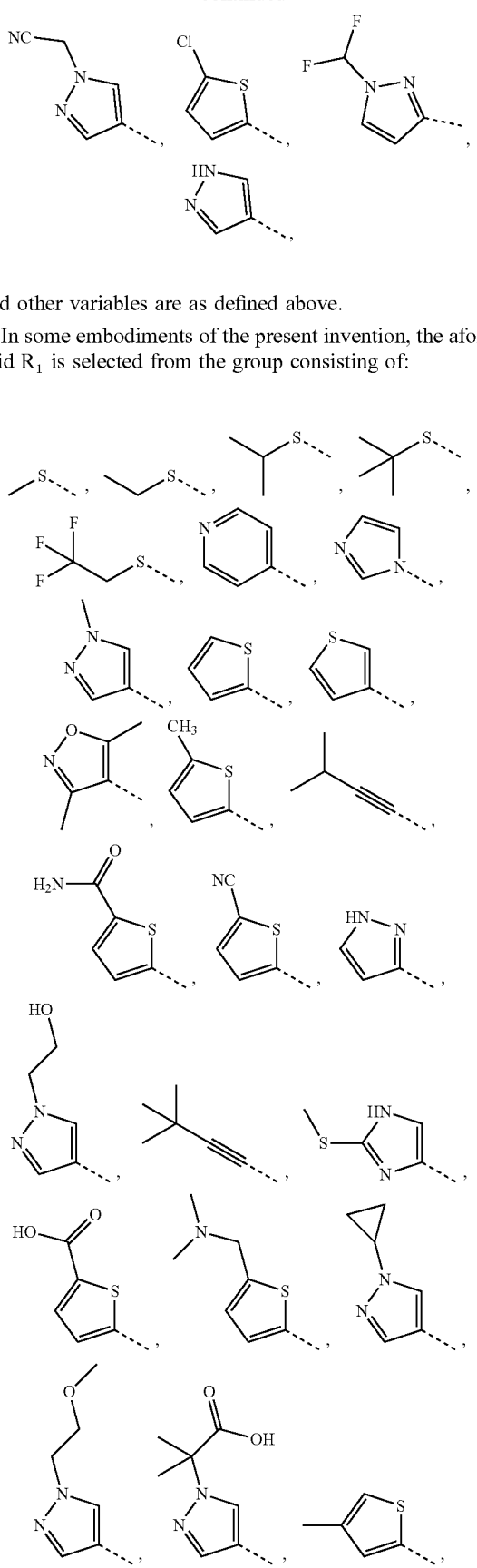

-continued

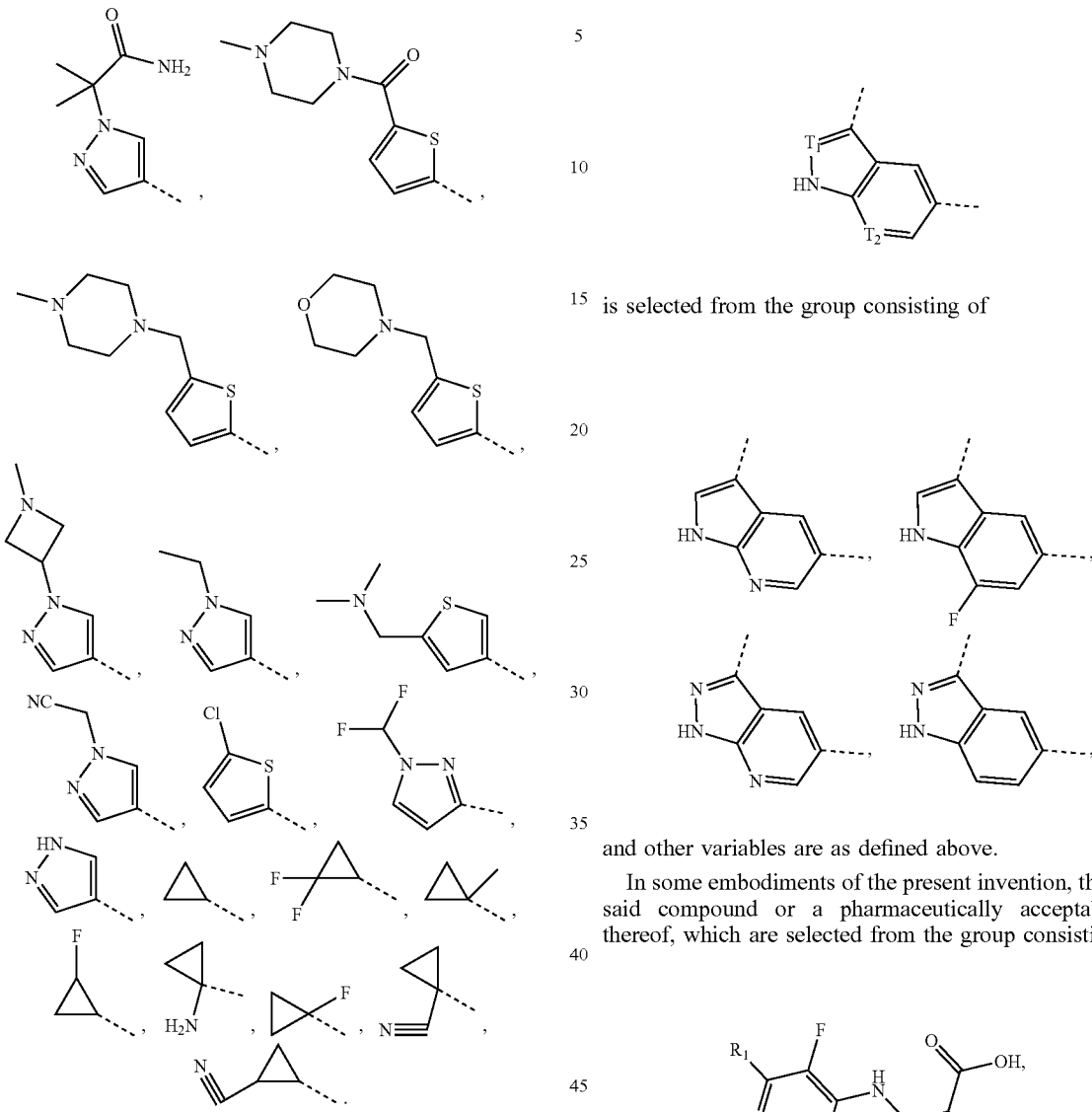

and other variables are as defined above.

In some embodiments of the present invention, the aforesaid $T_2$ is selected from the group consisting of: N, CH or C(F), and other variables are as defined above.

In some embodiments of the present invention, the aforesaid $R_3$ is selected from the group consisting of H, halogen, CN, $NH_2$, OH, or selected from the group consisting of: $C_{1-3}$ alkyl which is optionally substituted with 1, 2 or 3 R or R', and other variables are as defined above.

In some embodiments of the present invention, the aforesaid $R_3$ is selected from the group consisting of H, F, Cl, Br, I, CN, $NH_2$, OH, or selected from the group consisting of: Me, Et which are optionally substituted with 1, 2 or 3 R or R', and other variables are as defined above.

In some embodiments of the present invention, the aforesaid $R_3$ is selected from the group consisting of H, F, Cl, Br, I, CN, $NH_2$, OH, Me, Et, $CF_3$, and other variables are as defined above.

In some embodiments of the present invention, the aforesaid structural unit is selected from the group consisting of and other variables are as defined above.

In some embodiments of the present invention, the aforesaid compound or a pharmaceutically acceptable salt thereof, which are selected from the group consisting of:

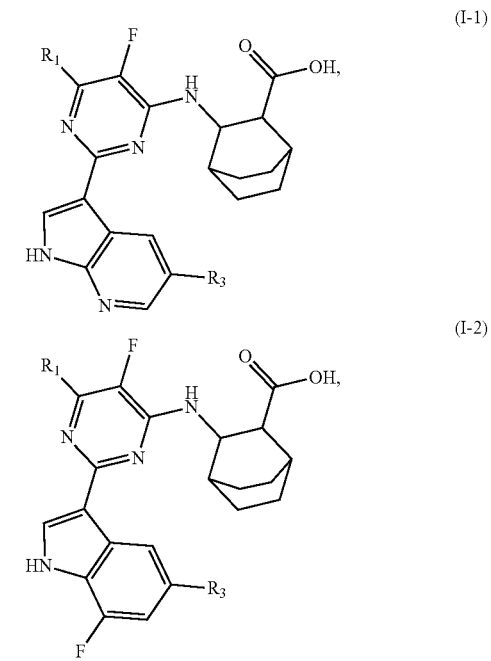

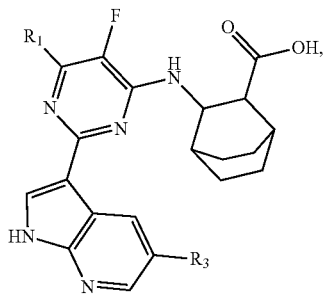 (I-3)
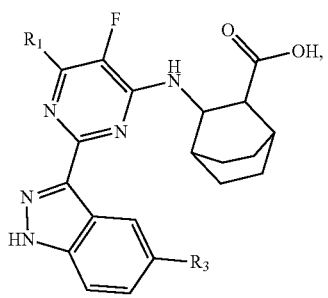 (I-4)
wherein, $R_1$, $R_3$ are as defined above.
The present invention may further comprise some embodiments of any combination of a variety of variables as described above.
The present invention further provides a compound of the following formula or a pharmaceutically acceptable salt thereof, which is selected from the group consisting of:
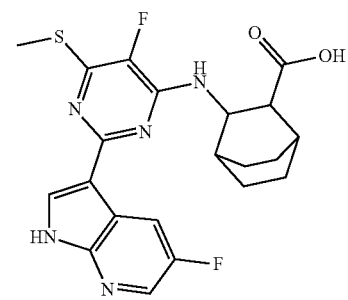
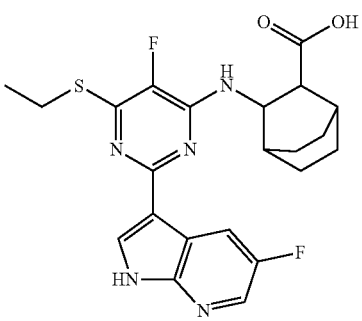
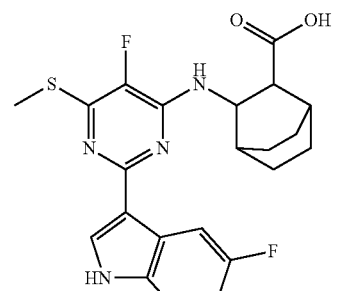
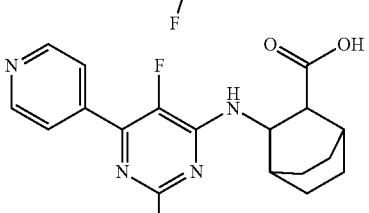
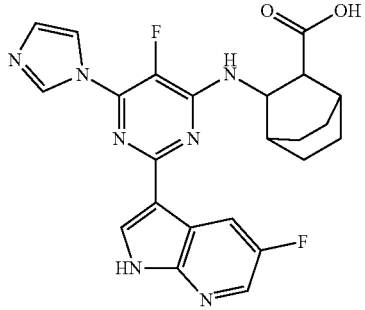
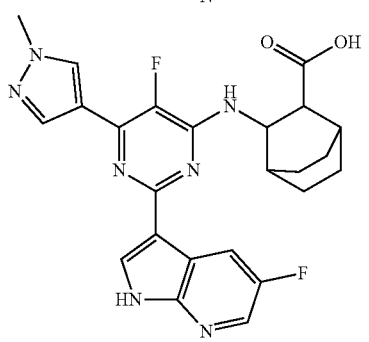
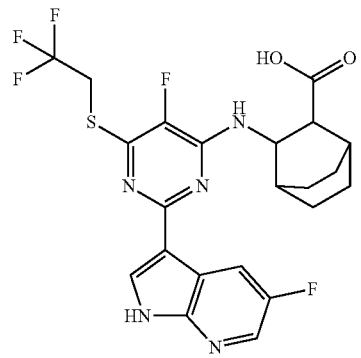

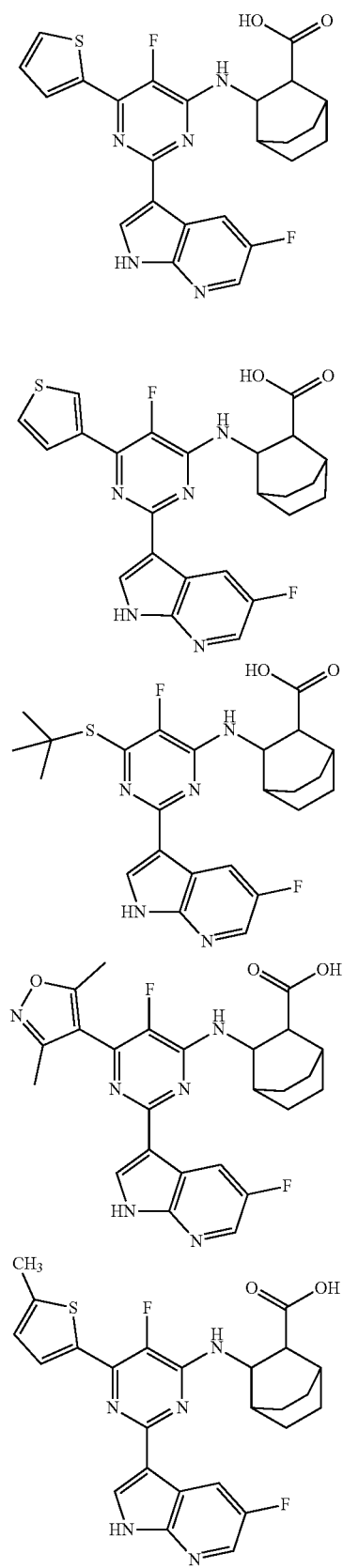
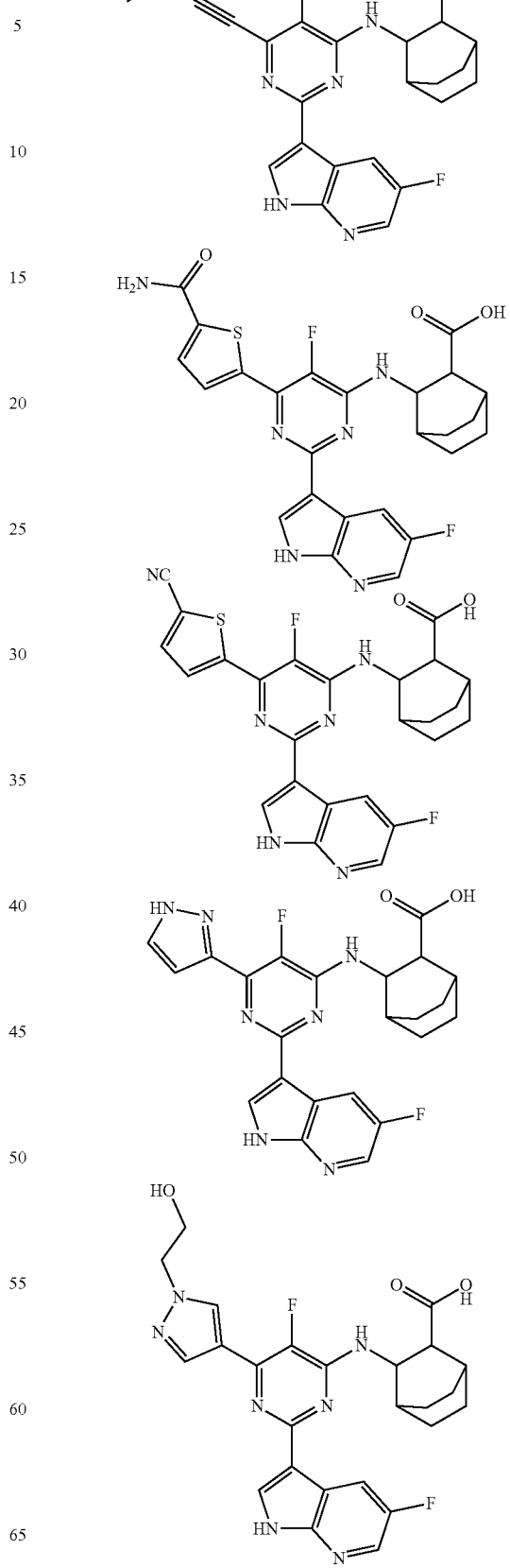

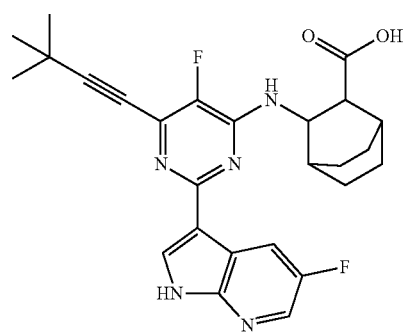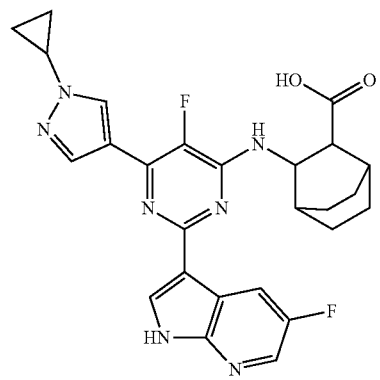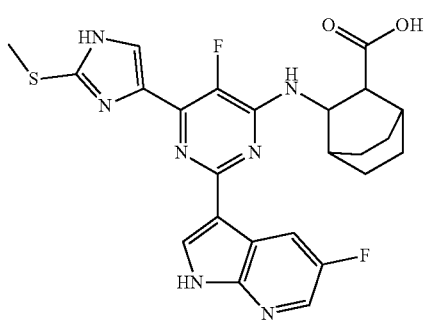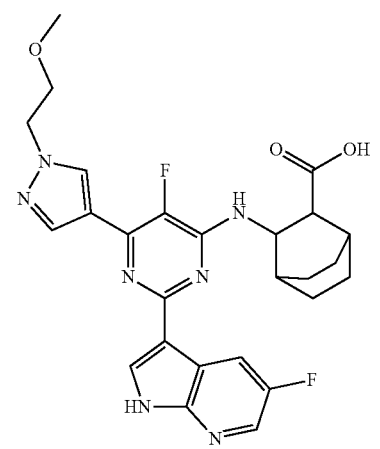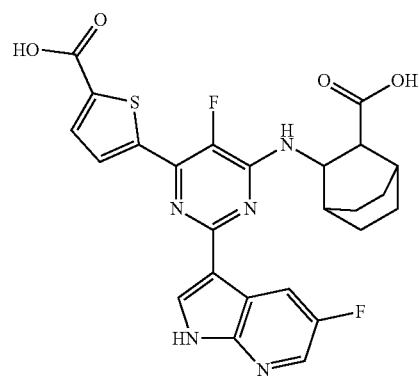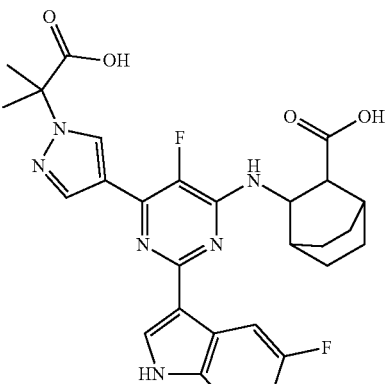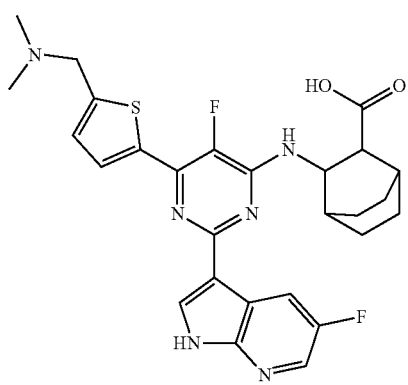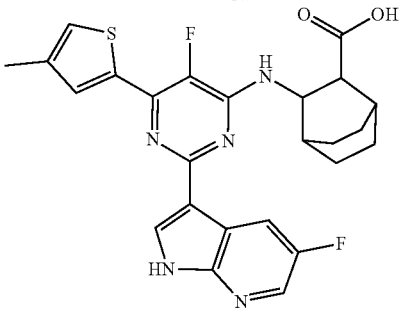

-continued
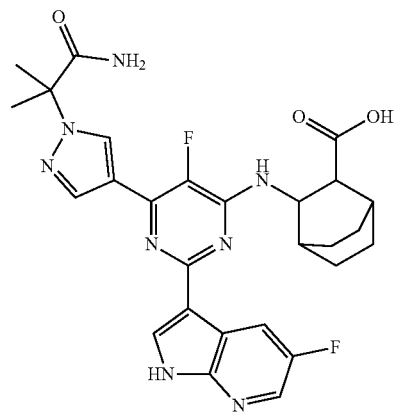
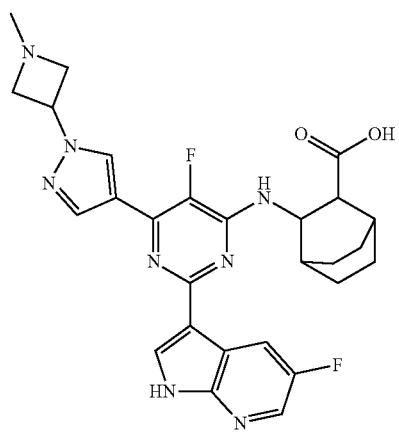
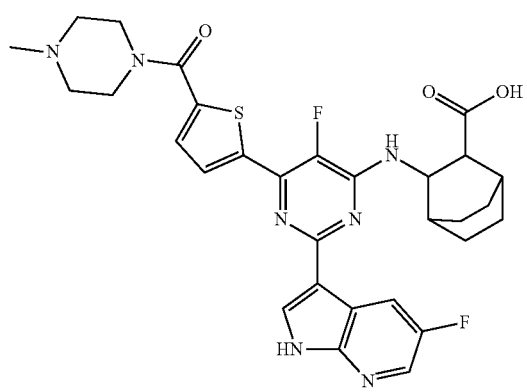
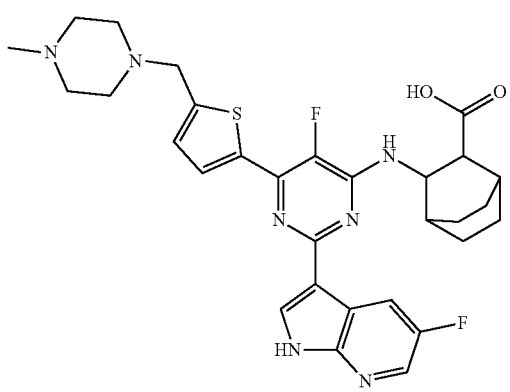
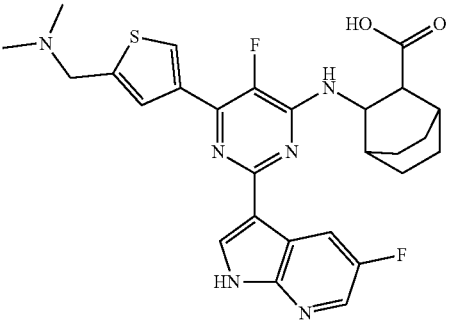
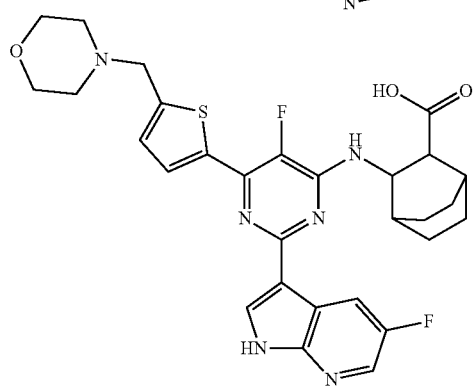
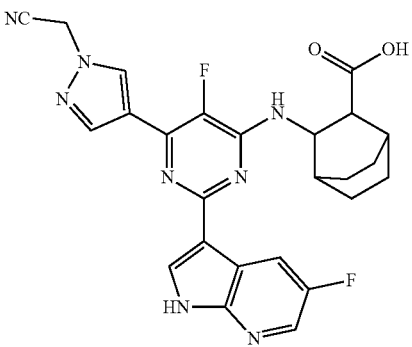

-continued
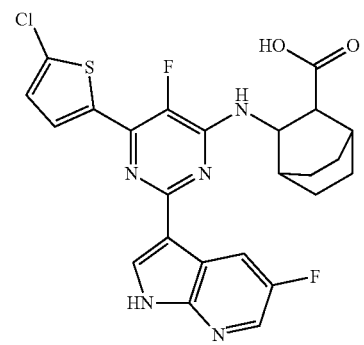
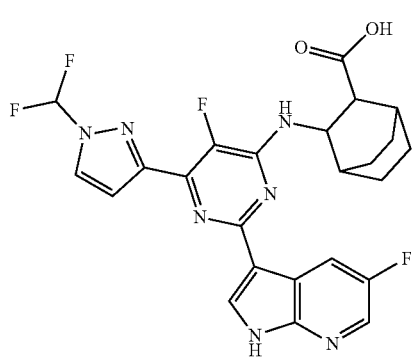
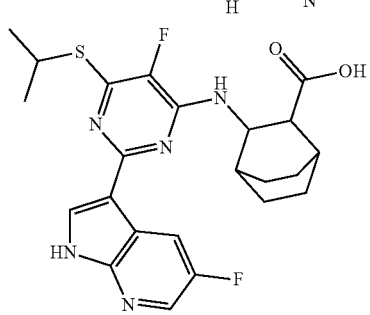
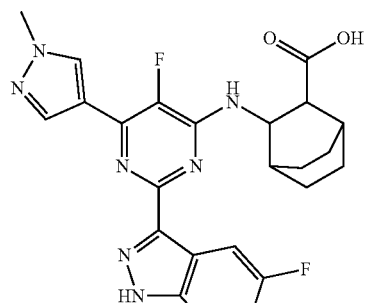
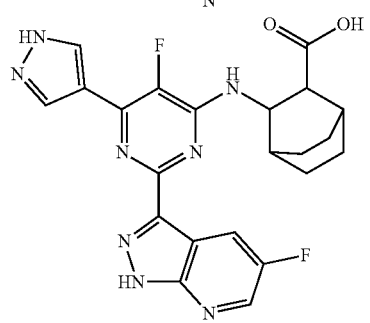
-continued
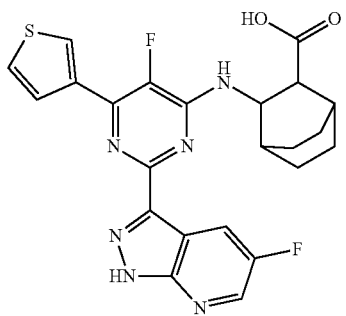
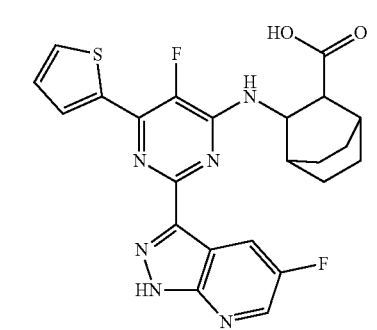
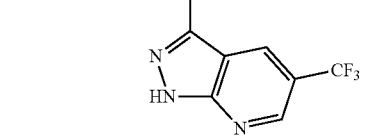
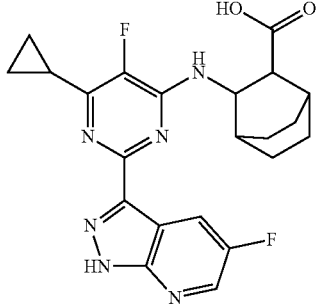
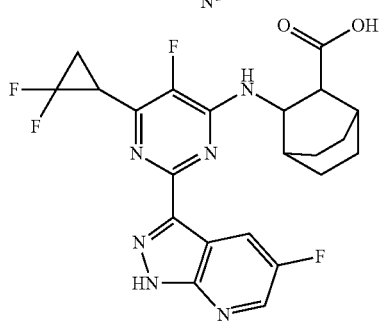

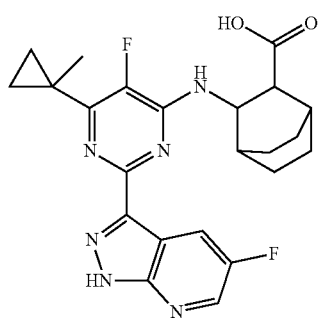
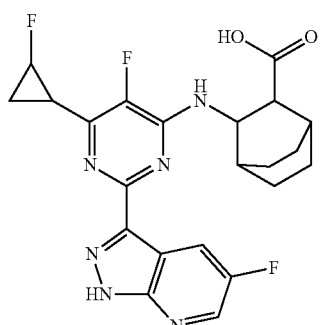
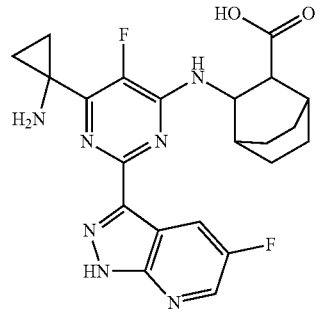
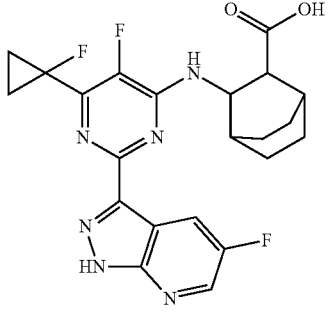
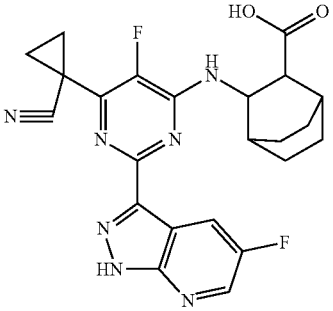
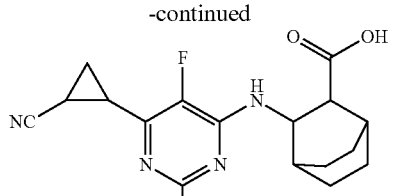
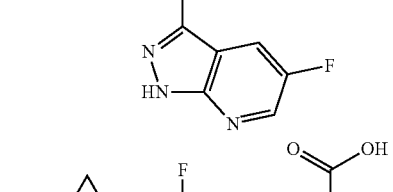
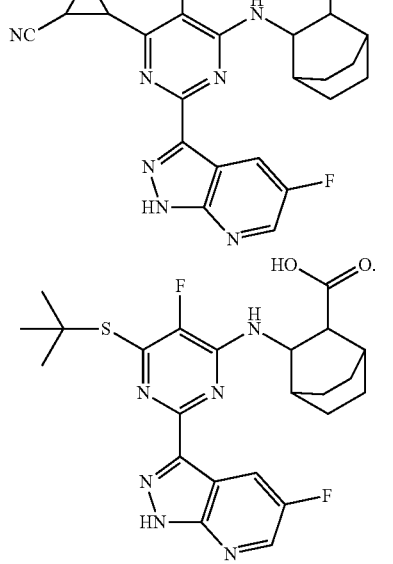
The present invention further provides a compound of the following formula or a pharmaceutically acceptable salt thereof, which is selected from the group consisting of.
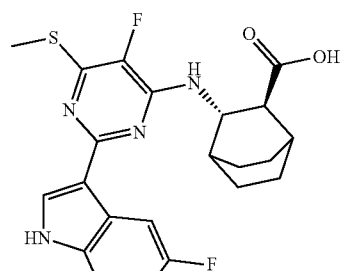
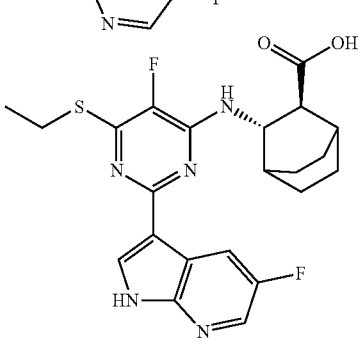

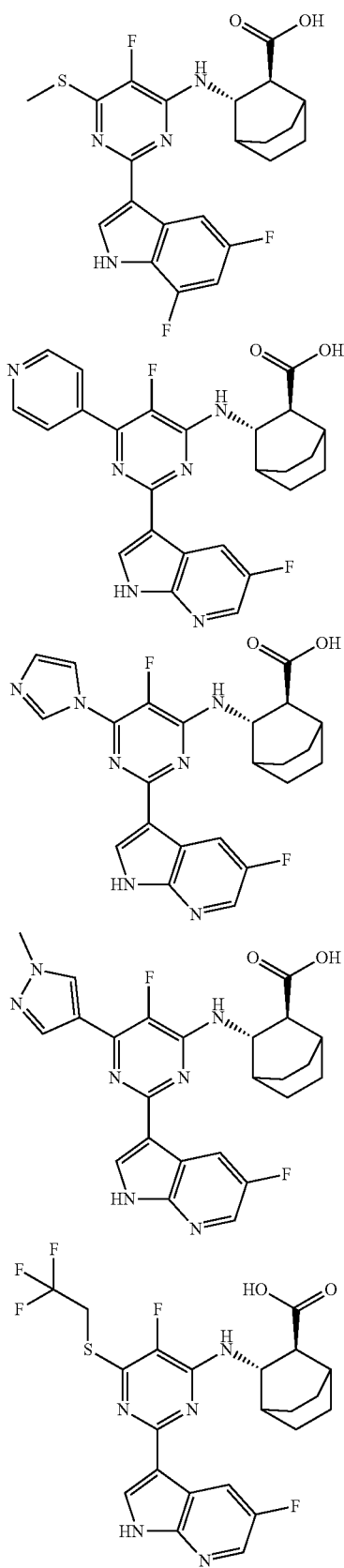
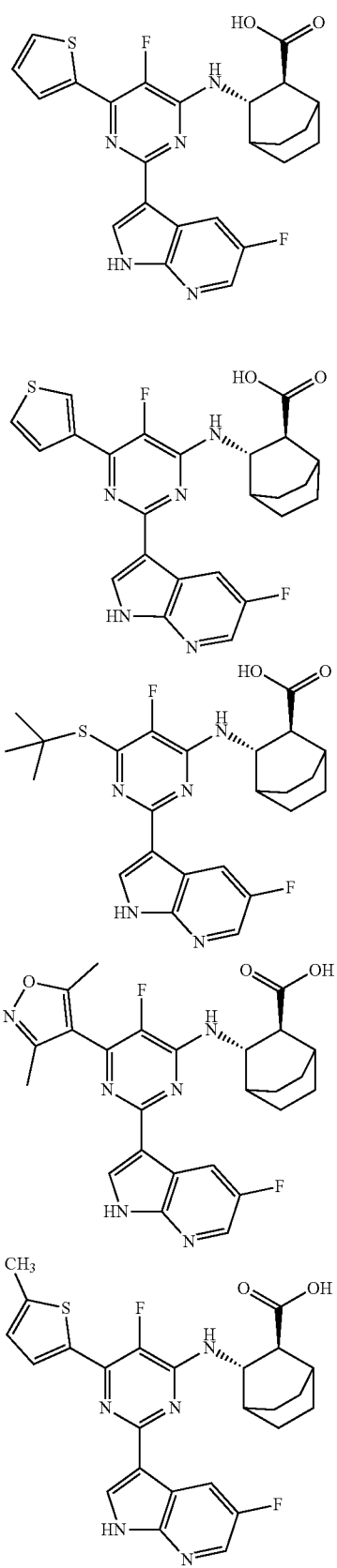

-continued
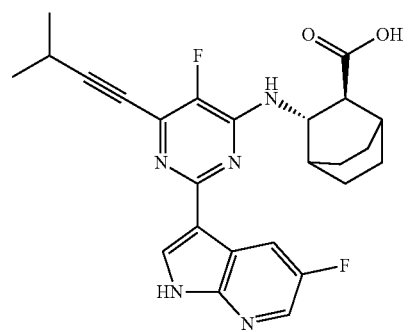
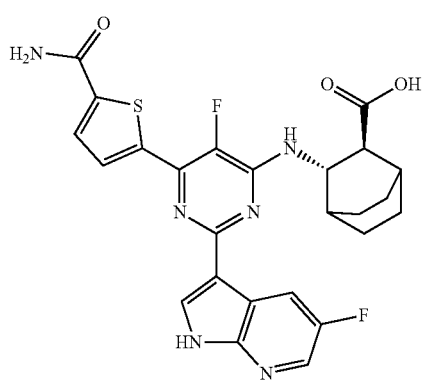
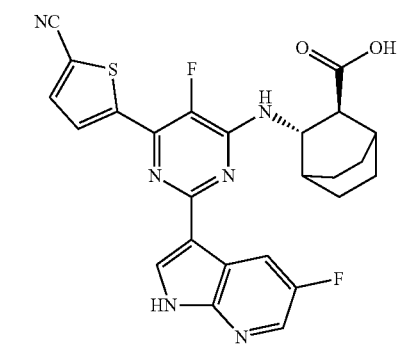
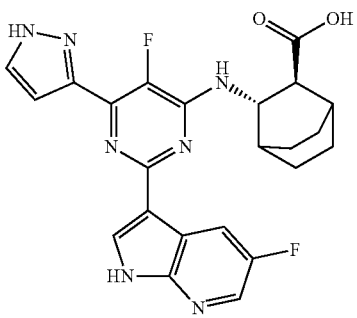
-continued
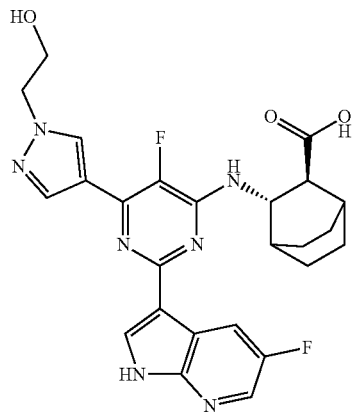
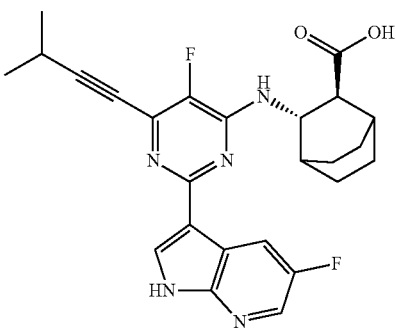
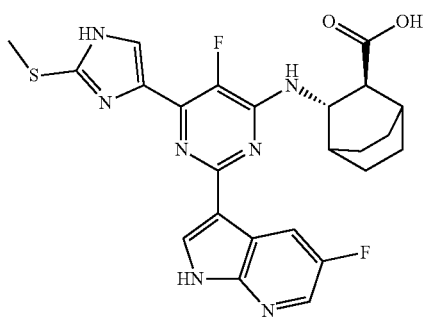
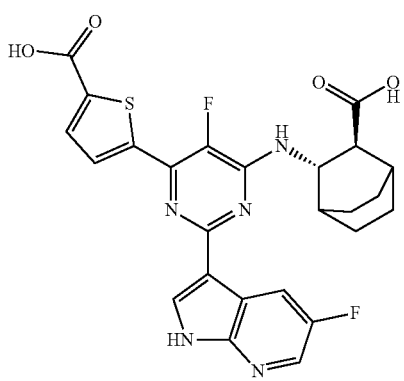

31
-continued
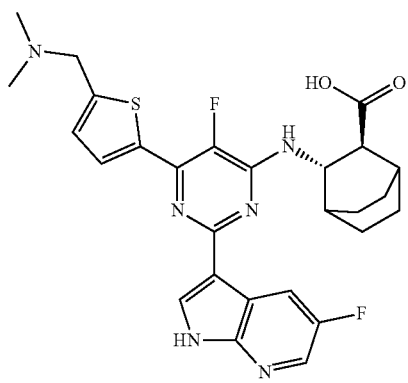
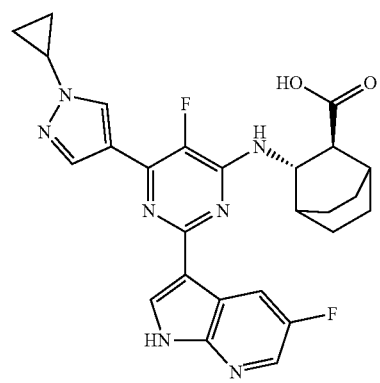
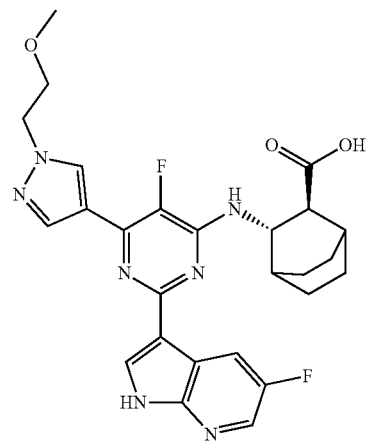
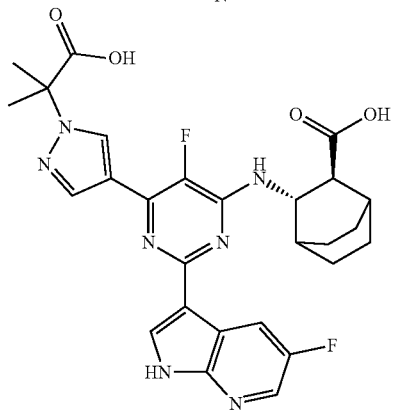
32
-continued
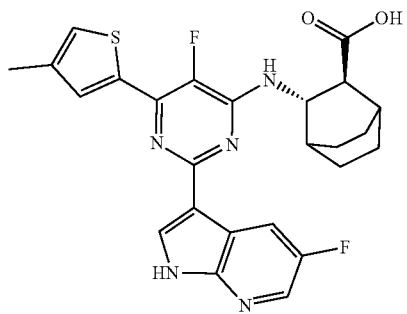
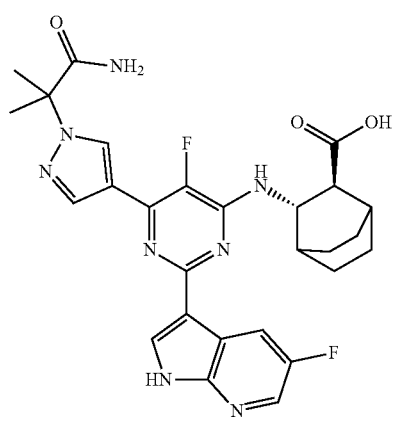
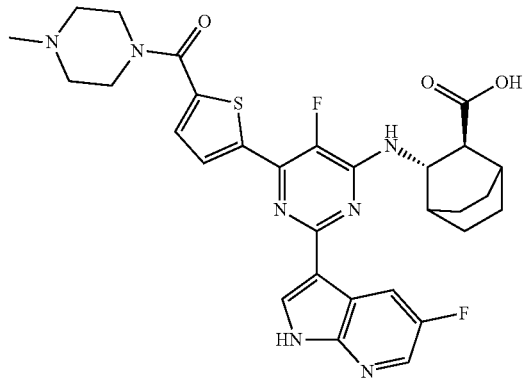
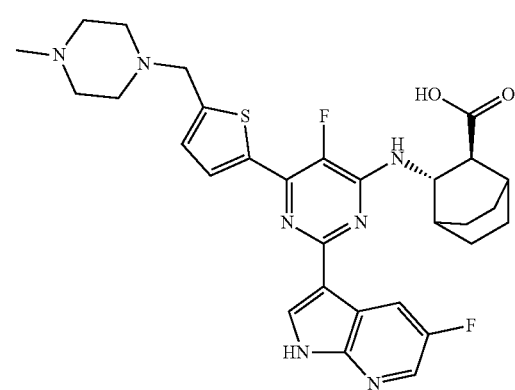

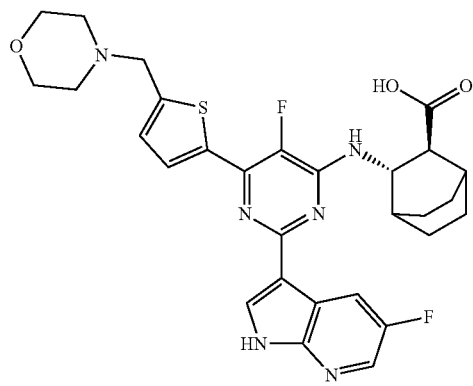
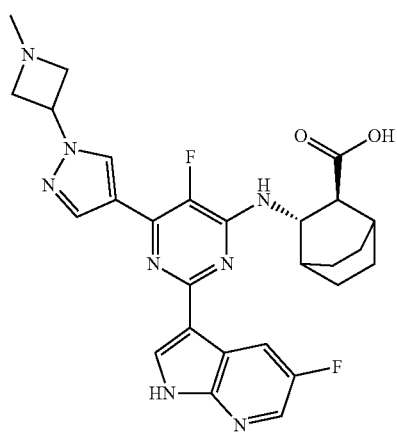
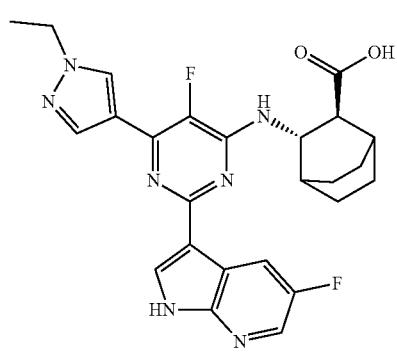
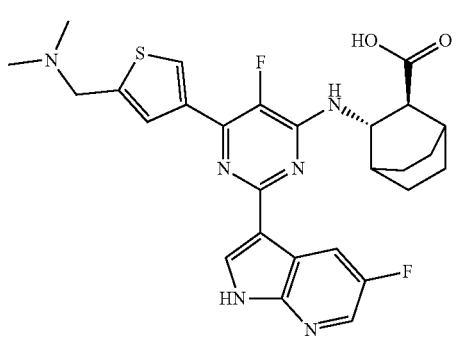
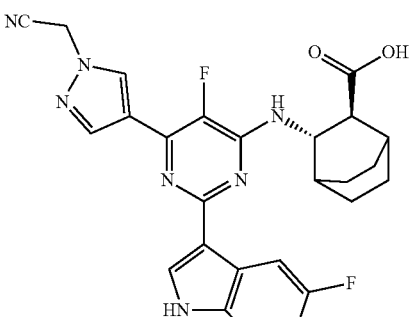
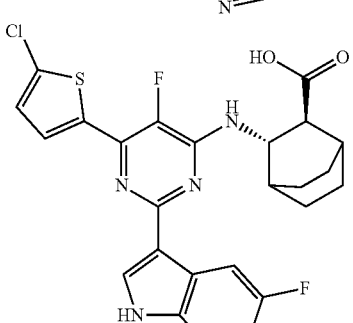
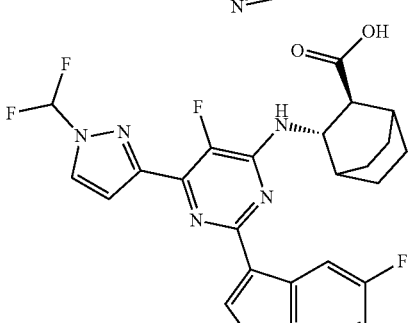
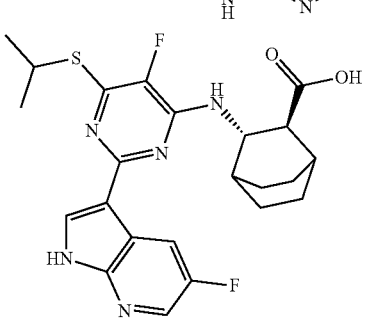
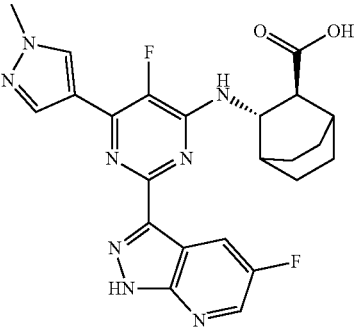

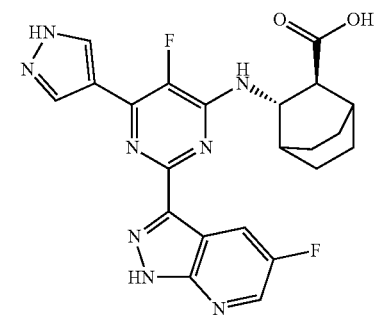
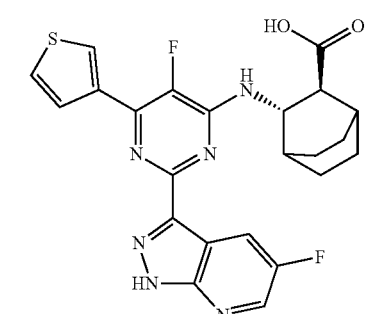
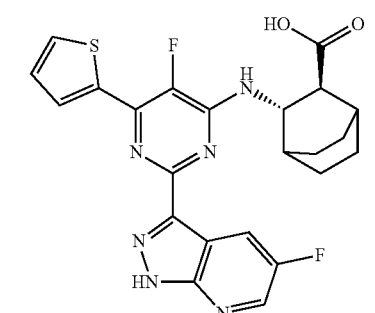
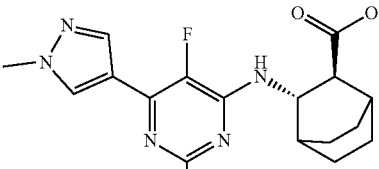
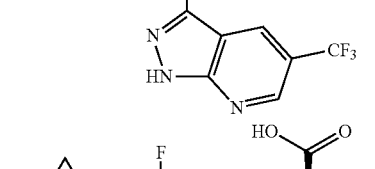
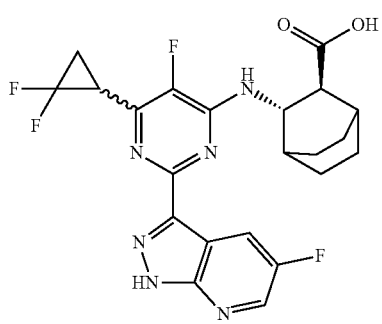
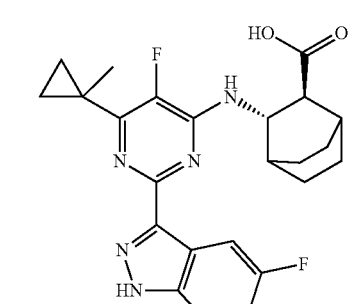
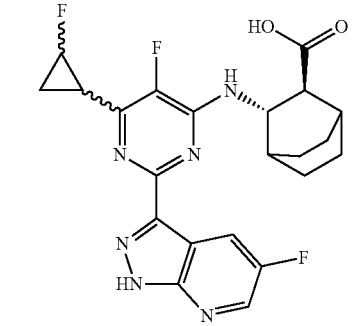
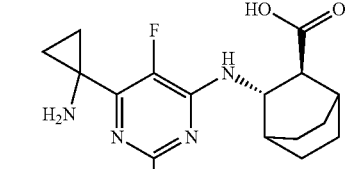
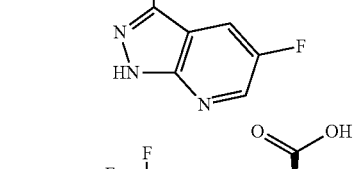
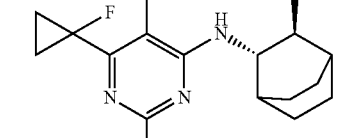
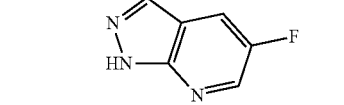

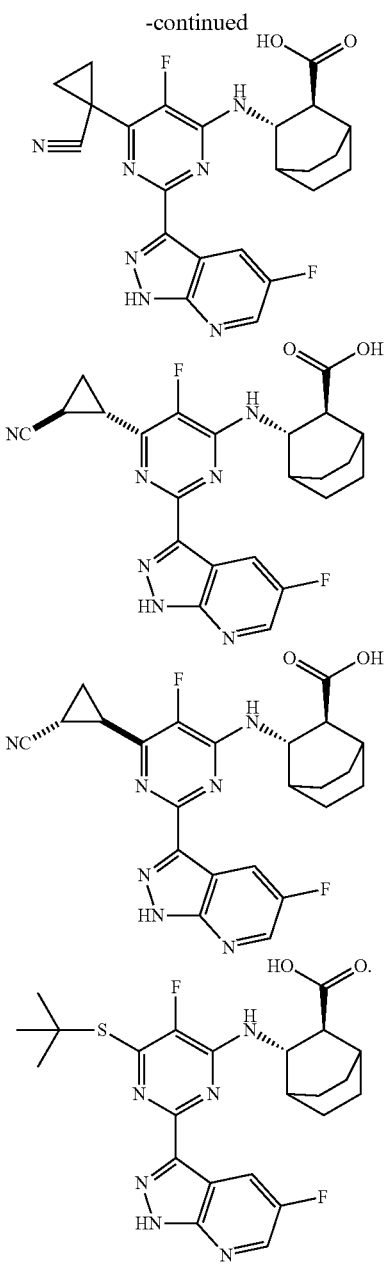

The present invention further provides a use of the aforesaid compounds or a pharmaceutically acceptable salt thereof in the preparation of a drug for treating diseases associated with influenza viruses.

Technical Effect

The compounds of the present invention are primarily used for the prevention and treatment of influenza caused by influenza A virus as well as influenza caused by highly pathogenic avian influenza virus, which, compared with existing clinical medicines, have highly safety, good oral bioavailability, and the potential of still having significant antiviral activity on influenza A virus strains resistant to existing clinical medicines.

Related Definitions

Unless stated otherwise, the following terms and phrases as used herein are intended to have the following meanings.

A particular term or phrase should not be deemed indefinite or unclear without a special definition, but should be understood in the ordinary sense. When a trade name is used herein, it is intended to refer to the corresponding commercially available product thereof or the active ingredients thereof. The term "pharmaceutically acceptable" as used herein means that by clinically reliable judgement, the compounds, materials, compositions and/or dosage forms are suitable for use in contact with human and animal tissues without excessive toxicities, irritations, allergic reactions, or other problems or complications, and are commensurate with a reasonable benefit/rist ratio.

The term "pharmaceutically acceptable salt" refers to salts of the inventive compounds prepared from the inventive compounds having specific substituent(s) with a relatively non-toxic acid or base. When the compounds of the present invention comprise a relatively acidic functional group, it is possible to obtain a base addition salt by means of contacting a sufficient amount of base with a neutral form of such compounds in a pure solution or a suitable inert solvent. The pharmaceutically acceptable base additional salts comprise sodium, potassium, calcium, ammonium, organic amine or magnesium salts, or the like. When the compounds of the present invention comprise relatively basic functional groups, it is possible to obtain an acid additional salt by means of contacting a sufficient amount of acid with a neutral form of such compounds in a pure solution or a suitable inert solvent. Examples of the pharmaceutically acceptable acid addition salts comprise inorganic acid salts, including, e.g., hydrochloride, hydrobromide, nitrate, carbonate, bicarbonate, phosphorate, monohydrogen phosphate, dihydrogen phosphate, sulfate, hydrosulfate, hydroiodate, phosphite, etc.; and organic acid salts including, e.g., acetate, propionate, isobutyrate, maleate, malonate, benzoate, succinate, suberate, fumarate, lactate, mandelate, phthalate, benzenesulfonate, tosilate, citrate, tartarate and methanesulfonate and the like; and salts of amino acids (e.g., arginine or the like), as well as salts of organic acids, e.g., glucuronic acid or the like (see Berge et al., "Pharmaceutical Salts", Journal of Pharmaceutical Science 66: 1-19 (1977)). Some particular compounds of the present invention have basic and acid functional groups, and thus can be converted to any one of base or acid additional salt.

Preferably, the neutral form of the compounds can be regenerated by means of contacting a salt with a base or an acid, followed by isolating the parent compound. The parent form of a compound differs from its various salt forms in certain physical properties, e.g., different solubility in a polar solvent.

The term "pharmaceutically acceptable salt" as used herein belongs to a derivative of the compounds of the present invention, wherein the parent compound is modified by forming a salt with acid or base. Examples of the pharmaceutically acceptable salts comprise, but are not limited to, inorganic or organic acid salts of basic groups, such as amines; basic metal or organic salts of acidic groups, such as, carboxylate. The pharmaceutically acceptable salts comprise conventional non-toxic salts or quandary ammonium salts of parent compounds, such as, salts formed from non-toxic inorganic or organic acids. Conventional non-toxic salts comprise, but are not limited to those derived from inorganic and organic acids selected from the group consisting of 2-acetoxybenzoic acid, 2-hydroxyethanesulfonic acid, acetic acid, ascorbic acid, benzenesulfonic acid, benzoic acid, hydrocarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionate, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalacturon, propionic acid, salicylic acid, stearic acid, folinate, succinic acid, aminosulfonic acid, p-aminobenzenesulfonic acid, sulfuric acid, tannin, tartaric acid and p-toluenesulfonic acid.

The pharmaceutically acceptable salts of the present invention may be chemically synthesized from a parent compound having an acidic or a basic functional group via a conventional chemical method. In general, such salts are prepared by reacting these compounds in a form of free acid or base with a stoichiometric amount of a suitable base or acid in water or an organic solvent or a mixture thereof. Typically, non-aqueous mediums, e.g., ether, ethyl acetate, ethanol, isopropanol, or acetonitrile or the like, are preferred.

In addition to the salt form, the compounds provided in the present invention may be present in a form of prodrug. The prodrug of the compounds as described herein can be easily converted to the compounds of the present invention via chemical transformation under physiological conditions. Moreover, the prodrugs may be converted to the compounds of the present invention via chemical or biochemical process in vivo.

Some compounds of the present invention may be present in a form of non-solvate or solvate, including hydrate. In general, both the non-solvate form and the solvate form are encompassed within the scope of the present invention.

Some compounds of the present invention may have an asymmetric carbon atom (the optical center) or a double bond. Racemates, diastereomers, geometric isomers, and individual isomers are all encompassed within the scope of the present invention.

Unless stated otherwise, the wedge bond and dashed bond ( ◢ ,ⁿˢ ) are used to indicate the absolute configuration of a stereocenter; ◢ ,ⁿˢ is used to indicate the relative configuration of a stereocenter. When the compounds as described herein comprise an olefinic double bond or other geometrically asymmetric centers, unless defined otherwise, they comprise E-, Z-geometrical isomers. Similarly, all the tautomers are encompassed within the scope of the present invention.

The compounds of the present invention may be present in specific geometric or stereoisomeric forms. It is envisioned in that all forms of the compounds as described in the present invention, including cis- and trans-isomers, (−)- and (+)-enantiomers, (R)- and (S)-enantiomers, diastereomers, (D)-isomers, (L)-isomers, as well as racemic mixture thereof and other mixture, such as, enantiomer- or diastereomer-enriched mixture, are encompassed within the scope of the present invention. Substituents, such as, alkyl, etc., may comprise additional asymmetric carbon atoms. All of these isomers and the mixtures thereof are encompassed within the scope of the present invention.

Chiral synthesis or chiral reagents or other conventional technologies may be used to prepare optically active (R)- and (S)-isomers and D- and L-isomers. If one enantiomer of a compound of the present invention is desired, it can be prepared by asymmetric synthesis or derivatization with a chiral auxiliary, in which the produced mixture of diastereometers are isolated, and the auxiliary group is cleaved to provide a pure enantiomer as desired. Alternatively, if the molecule contains a basic functional group (e.g., amino) or an acidic functional group (e.g., carboxyl), it may be reacted with a suitable optically active acid or base to form salts of diastereomers which are in turn subject to diastereoisomers resolution via a conventional method as established in the art, and recovered to give pure enantiomers. Furthermore, the separation of the enantiomers and diastereoisomers is usually accomplished by chromatography, which utilizes a chiral stationary phase, and optionally combined with a chemical derivation method (e.g., producing a carbamate from amine).

The compounds of the present invention may comprise a non-naturally occurring ratio of isotope(s) at the site of one or more atoms constituting the compounds. For instance, the compound may be labelled with radioisotope(s), such as tritium ($^3$H), iodine-125 ($^{125}$I) or C-14 ($^{14}$C). All isotopic variations of the compounds of the present invention, independent of their radioactivity, are encompassed within the scope of the present invention.

The term "pharmaceutically acceptable carrier" refers to any preparation or carrier medium which can deliver an effective amount of active substances of the present invention, does not interfere with the bioactivity of the active substances, and is not toxic to subject or patient. Representative carriers comprise water, oils, vegetables and minerals, cream base, lotion base, ointment base, and the like. These bases comprise suspending agents, thickening agents, transdermal enhancers, and the like. The preparations of these bases are well known by the skilled persons in the cosmetic field or topical drug field. Other information of carriers may be seen in Remington: the Science and Practice of Pharmacy, 21st Ed., Lippincott, Williams & Wilkins (2005), the content of which is incorporated herein by reference.

The term "excipient" generally refers to carriers, diluents, and/or mediums required by the preparation of an effective pharmaceutical composition.

With respect to drugs or pharmaceutically active agents, the term "effective amount" or "therapeutically effective amount of" refers to a sufficient amount of drugs or medicaments which are not toxic but can achieve the desired effect. As for the oral dosage forms of the present invention, the "effective amount" of an active substance in the composition refers to the amount required to achieve the desired effect when used in combination with another active substance in the composition. The determination of the effective amount varies from person to person, depending on the age and general conditions of the subject, and also on the particular active substance. The appropriate effective amount in individual cases may be determined by a person skilled in the art via conventional experiments.

The term "active ingredient", "therapeutic agent", "active substance" or "active agent" refers to a chemical entity which can effectively treat disorders, diseases, or illness.

"Optional" or "optionally" means that the event or condition as described may but does not have to occur, and the description includes both the case that the event or condition occur and the case that the event or condition does not occur.

The term "substituted" means that any one or more hydrogen atom attached to a particular atom are replaced with a substituent, and variants of heavy hydrogen and hydrogen may be included, as long as the valence of the particular atom is normal and the substituted compound is stable. When the substituent is a ketone group (i.e., =O), it means that two hydrogen atoms are replaced. Ketone substitution does not occur on an aromatic group. The term "optionally substituted" means that it is may or may not be substituted, and Unless defined otherwise, the type and number of substituents may vary randomly as long as they are chemically achievable.

When any variable (e.g., R) occur more than once in the composition or structure of a compound, its definition is independent in each case. Thus, as an example, if a group is substituted with 0-2 R, the group may be optionally substituted with at most two R, and the substituent R is independently selected in each case. Moreover, a combination of a substituent and/or the variants thereof is allowable only if such combination leads to a stable compound.

When the number of a linking group, such as —(CRR)$_0$—, it means that the linking group is single bond.

When a variable is selected from the group consisting of single bond, it means that the two groups linked thereby are directly linked, e.g., when L in A-L-Z represents a single bond, this structure is actually A-Z.

When a substituent is absent, it means that the substituent does not exist, for instance, when X in A-X is absent, it means that the structure is actually A. When a substituent may be cross-linked to two atoms in a ring, the substituent may be bonded to any atom in the ring. When a recited substituent does not indicate through which atom it is attached to the compound included but not specifically mentioned in the general formula of the chemical structure, the substituent may be bonded through any atom therein. The combination of a substituent and/or variants thereof is allowable only if such combination leads to a stable compound. For example, the structural unit or

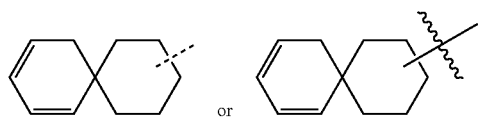

indicates that it may be replaced at any position of cyclohexyl or cyclohexadiene.

Unless defined otherwise, the term "hetero-" means heteroatom or heteroatomic group (i.e., atomic group containing heteroatom), including atoms other than carbon (C) and hydrogen (H) as well as atomic groups containing these heteroatoms, e.g., oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and optionally substituted —C(=O)N(H)—, —N(H)—, —C(=NH)—, —S(=O)$_2$N(H)— or —S(=O)N(H)—.

Unless defined otherwise, "cyclo/ring" means that substituted or unsubstituted cycloalkyl, heterocycloalkyl, cycloalkenyl, heretocycloalkenyl, cycloalkynyl, heretocycloalkynyl, aryl or heteroaryl. The so-called ring comprises mono ring, dual ring, spiro ring, fused ring, or bridge ring. The atomic number in the ring is typically defined as the membered number of the ring, e.g., "5-7 membered ring" refers to there are 5-7 atoms in a cyclized arrangement. Unless defined otherwise, the ring contains optionally 1-3 heteroatoms. Thus, "5-7 membered ring" comprises, e.g., phenyl, pyridinyl and piperidyl; and on the other hand, the term "5-7 membered heterocycloalkyl ring" comprises pyridyl and piperidyl, but does not comprise phenyl. The term "cyclo/ring" further comprises a ring system containing at least a ring, of which each "ring" meets independently the aforesaid definition.

Unless defined otherwise, the term "heterocycle" or "heterocyclyl" is intended to mean stable mono-, bi-, or tri-cycle containing heteroatom or heteroatomic group that may be saturated, partially unsaturated or unsaturated (aromatic), and may comprise carbon atoms and 1, 2, 3 or 4 ring heteroatoms independently selected from the group consisting of N, O and S, wherein any of the aforesaid heterocycles may be fused to a phenyl ring to form a dual ring. Nitrogen and sulfur heteroatoms may be optionally oxidized (i.e., NO and S(O)$_p$, wherein p is 1 or 2). Nitrogen atom may be substituted or unsubstituted (i.e., N or NR, wherein R is H or another substituent as defined herein). The heterocycle may be attached to a pendant group of any heteroatom or carbon atom to form a stable structure. If the resultant compound is stable, the heterocycle as described herein may be substituted at the carbon- or nitrogen-site. Nitrogen atom in the heterocycle is optionally quaternized. A preferred embodiment is that when the total number of S and O atoms in the heterocycle exceeds one, these heteroatoms are not adjacent to each other. Another preferred embodiment is that the total number of S and O atoms in the heterocycle does not exceed 1. As used herein, the term "aromatic heterocyclyl" or "heteroaryl" is intended to mean stable 5-, 6-, 7-membered monocyclic or bicyclic, or 7-, 8-, 9- or 10-membered bicyclic heterocyclyl aromatic ring that comprise carbon atoms and 1, 2, 3 or 4 ring heteroatoms independently selected from the group consisting of N, O and S. Nitrogen atom may be substituted or unsubstituted (i.e., N or NR, wherein R is H or another substituent as defined herein). Nitrogen and sulfur heteroatoms may be optionally oxidized (i.e., NO and S(O)$_p$, wherein p is 1 or 2). It is worth to note that the total number of S and O atoms in the aromatic heretocycle does not exceed 1. Bridge ring is also encompassed within the definition of heterocycle. When one or more atoms (i.e., C, O, N or S) link two non-adjacent carbon atoms or nitrogen atoms, a bridge ring is formed. Preferred bridge ring comprises, but are not limited to: one carbon atom, two carbon atoms, one nitrogen atom, two nitrogen atoms, and one carbon-nitrogen bond. It is worth to note that one bridge always converts a monocycle to a tricycle. In a bridge ring, substituent(s) of the ring may also be attached to the bridge.

Examples of heterocyclic compounds include, but are not limited to: acridinyl, azocinyl, benzimidazolyl, benzofuryl, benzothiofuryl, benzothiophene, benzothiophenyl, benzoxazolyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furyl, furazanyl, imidazolidinyl, imidazolinyl, imidazolyl, 1H-indazolyl, indolenyl, indolinyl, indolizinyl, indolyl, 3H-indolyl, isobenzofuryl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindyl, pyrimidyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Fused ring and spiro ring compounds are also included.

Unless defined otherwise, the term "hydrocarbonyl" or its specific concepts (such as alkyl, alkenyl, alkynyl, aryl, etc.) alone or as a portion of another substituent represent a linear, branched, or cyclic hydrocarbon radical or a combination thereof, that may be completely saturated (such as, alkyl), mono- or poly-unsaturated (such as, alkenyl, alkynyl, aryl); mono- or poly-substituted; monovalent (such as, methyl), divalent (such as, methylene) or polyvalent (such as, methine); and may comprise divalent or polyvalent atomic group, and have a specified number of carbon atoms (such as, $C_1$-$C_{12}$ represents 1-12 carbon atoms, $C_{1-12}$ is selected from the group consisting of $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from the group consisting of $C_3$, $C_4$, $C_5$, $C_6$, $C_7$, $C_8$, $C_9$, $C_{10}$, $C_{11}$ and $C_{12}$). "Hydrocarbonyl" comprises, but are not limited to aliphatic hydrocarbonyl and aromactic hydrocarbonlyl, wherein the aliphatic hydrocarbonyl may be linear or cyclic, and in particular comprises, but are not limited to alkyl, alkenyl, alkynyl, and the aromatic hydrocarbonyl comprises, but are not limited to 6-12 membered aromatic hydrocarbonyls, such as, phenyl, naphthyl, and the like. In some embodiments, the term "hydrocarbonyl" represents linear or branched atomic groups or their combination that may be completely saturated, mono- or poly-unsaturated, and may comprise divalent and polyvalent atomic group. Examples of saturated hydrocarbon atomic group comprise, but are not limited to methyl, ethyl, n-propyl, iso-propyl, n-butyl, tert-butyl, iso-butyl, sec-butyl, iso-butyl, cyclohexyl, (cyclohexyl) methyl, cyclopropylmethyl, and homologs or isomers of n-pentyl, n-hexyl, n-heptyl, n-octyl, and other atomic groups. Unsaturated hydrocarbonyls may have one or more double bonds or triple bonds, and the examples thereof comprise, but are not limited to ethenyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers.

Unless defined otherwise, the term "hetero-hydrocarbonyl" or its specific concepts (such as heteroalkyl, heteroalkenyl, heteroalkynyl, heteroaryl, etc.) alone or in combination with another term represents a stable linear, branched or cyclic hydrocarbon atomic group or a combination thereof, that consists of a number of carbon atoms and at least a heteroatom. In some embodiments, the term "heteroalkyl" alone or in combination with another term represents a stable linear, branched hydrocarbon atomic group or a combination thereof that consists of a number of carbon atoms and at least a heteroatom. In a typical embodiment, heteroatom is selected from the group consisting of B, O, N and S, wherein nitrogen and sulfur atoms are optionally oxidized, and nitrogen heteroatom is optionally quaternized. The heteroatom or heteroatomic group may be located at any internal site of the hetero-hydrocarbonyl, including the site through which the hetero-hydrocarbonyl is attached to the other moiety of the molecule. However, the term "alkoxy", "alkylamino" and "alkylthio" (or thio-alkoxy) belong to routine expressions, and refer to those attached to the other moiety of the molecule via an oxygen atom, amino, or sulfur atom, respectively. Examples comprise, but are not limited to —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —CH$_2$—CH═N—OCH$_3$ and —CH═CH—N(CH$_3$)—CH$_3$. At least two heteroatoms may be linked, e.g., —CH$_2$—NH—OCH$_3$.

Unless defined otherwise, the term "cyclyl", "heterocyclyl" or their specific concepts (such as aryl, heteroaryl, cycloalkyl, heterocycloalkyl, cycloalkenyl, heretocycloalkenyl, cycloalkynyl, heretocycloalkynyl, etc.) alone or in combination with other terms represent cyclized "hydrocarbonyl", "hetero-hydrocarbonyl", respectively. Moreover, for hetero-hydrocarbonyl or heterocyclyl (such as heteroalkyl, heterocycloalkyl), heteroatom(s) may be located at the site through which the heterocyclyl is attached to the other moiety of the molecule. Examples of cyclyl comprise, but are not limited to cyclopentyl, cyclohexyl, 1-cyclohexenyl, 3-cyclohexenyl, cycloheptyl, and the like. Non-limiting examples of heterocyclyl comprise 1-(1,2,5,6-tetrahydropyridyl), 1-piperidyl, 2-piperidyl, 3-piperidyl, 4-morpholinyl, 3-morpholinyl, tetrahydrofuran-2-yl, tetrahydrofuranoindol-3-yl, tetrahydrothien-2-yl, tetrahydrothien-3-yl, 1-piperazinyl and 2-piperazinyl.

Unless defined otherwise, the term "alkyl" is intended to mean a linear or branched saturated hydrocarbonyl, that may be mono-substituted (such as, —CH$_2$F) or poly-substituted (such as, —CF$_3$), and monovalent (such as, methyl), divalent (such as, methylene) or polyvalent (such as, methine). Examples of alkyl comprise methyl (Me), ethyl (Et), propyl (such as, n-propyl and iso-propyl), butyl (such as, n-butyl, iso-butyl, s-butyl, t-butyl), pentyl (such as, n-pentyl, iso-pentyl, neo-pentyl) or the like.

Unless defined otherwise, "alkenyl" refers to an alkyl having one or more carbon-carbon double bond at any site of the chain that may be mono-substituted or poly-substituted, and may be monovalent, divalent or polyvalent. Examples of alkenyl comprise ethenyl, propenyl, butenyl, pentenyl, hexenyl, butadienyl, pentadienyl, hexadienyl, and the like.

Unless defined otherwise, "alkynyl" refers to an alkyl having one or more carbon-carbon triple bond at any site of the chain that may be mono-substituted or poly-substituted, and may be monovalent, divalent or polyvalent. Examples of alkynyl comprise ethynyl, propynyl, butyryl, pentynyl and the like.

Unless defined otherwise, cycloalkyl comprises any stable cyclyl or polycyclyl in which any carbon atom is saturated, that may be mono-substituted or poly-substituted, and may be monovalent, divalent or polyvalent. Examples of these cycloalkyls comprise, but are not limited to, cyclopropyl, norbornanyl, [2.2.2]bicyclooctyl, [4.4.0]bicyclodecanyl, and the like.

Unless defined otherwise, cycloalkenyl comprises any stable cyclyl or polycyclyl comprising one or more unsaturated carbon-carbon double bonds at any site of the ring, which may be mono-substituted or poly-substituted, may be monovalent, divalent or polyvalent. Examples of these cycloalkenyls comprise, but are not limited to, cyclopentenyl, cyclohexenyl, and the like.

Unless defined otherwise, cycloalkynyl comprises any stable cyclyl or polycyclyl having one or more carbon-carbon triple bonds at any site of the ring, which may be mono-substituted or poly-substituted, and may be monovalent, divalent or polyvalent.

Unless defined otherwise, the term "halo" or "halogen" alone or as a part of another substituent represents a fluorine, chlorine, bromine or iodine atom. Moreover, the term "haloalkyl" is intended to comprise monohalo-alkyl and polyhalo-alkyl. e.g., the term "halo($C_1$-$C_4$) alkyl" is intended to comprise, but are not limited to trifluoromethyl, 2,2,2-trifluoroethyl, 4-chlorobutyl and 3-bromopropyl, etc. Unless defined otherwise, examples of haloalkyl comprise, but are not limited to: trifluoromethyl, trichloromethyl, pentafluoroethyl, and pentachloroethyl.

"Alkoxy" represents an alkyl that is attached via an oxygen bridge and has a particular number of carbon atoms. Unless defined otherwise, $C_{1-6}$ alkoxy comprises $C_1$, $C_2$, $C_3$, $C_4$, $C_5$ and $C_6$ alkoxy. Examples of alkoxy comprise, but are not limited to: methoxy, ethoxy, n-propoxy, iso-propoxy, n-butoxy, sec-butoxy, tert-butoxy, n-pentoxy and s-pentoxy.

Unless defined otherwise, the term "aryl" refers to poly-unsaturated aromatic substituent, that may be mono- or poly-substituted, mono-, di-, or poly-valent, and mono- or poly-cyclic (such as 1-3 rings; of which at least one ring is aromatic) fused or covalently bonded to each other. The term "heteroaryl" refers to aryl (or ring) containing 1-4 heteroatoms. In an exemplary example, the heteroatom is selected from the group consisting of B, N, O and S, wherein nitrogen atom and sulfur atom are optionally oxidized, and nitrogen atom is optionally quaternized. Heteroaryl may be attached via heteroatom to another moiety of a molecule. Non-limiting examples of aryl or heteroaryl comprise phenyl, naphthyl, diphenylyl, pyrrolyl, pyrazolyl, imidazolyl, pyrazinyl, oxazolyl, phenyl-oxazolyl, isoxazolyl, thiazolyl, furanyl, thienyl, pyridyl, pyrimidyl, benzothiazolyl, purinyl, benzimidazolyl, indolyl, isoquinnolyl, quinoxalinyl, quinolyl, 1-naphthyl, 2-naphthyl, 4-diphenylyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. Any one of the aforesaid aryl and heteroaryl cyclic substituent is selected from the acceptable substituents as described below.

Unless defined otherwise, aryl in combination with other term (e.g., aryloxy, arylthio, aralkyl) comprises the aryl and heteroaryl ring as defined above. Thus, the term "aralkyl" is intended to comprise those having aryl attached to alkyl (e.g., benzyl, phenylethyl, pyridylmethyl, etc.), including those in which carbon atom(s) (such as, methylene) have been replaced with oxygen atom, such as, phenoxymethyl, 2-pyridyloxymethyl3-(1-naphthyloxy) propyl and the like.

The term "leaving group" refers to a functional group or atom that may be replaced with another functional group or atom via a substitution reaction (e.g., a nucleophilic substitution reaction). For instance, representative leaving groups comprise trifluoromethanesulfonate; chloride, bromide, iodide; sulfonate, e.g., methanesulfonate, tosylate, p-bromobenzenesulfonate, p-toluenesulfonate, and the like; acyloxy, such as, acetoxy, trifluoroacetoxy, etc.

The term "protective group" comprises, but is not limited to "amino protective group", "hydroxyl protective group" or "mercapto protective group". The term "amino protective group" refers to the protective group adapted to prevent side reaction at the site of amino nitrogen. Representative amino protective groups comprise, but are not limited to: formyl; acyl, e.g., alkanoyl (such as, acetyl, trichloroacetyl or trifluoroacetyl); alkoxycarbonyl, such as, tert-butoxycarbonyl (Boc); arylmethoxycarbonyl, such as, carbobenzoxy (Cbz) and 9-fluorenylmethoxycarbonyl (Fmoc); aryl methyl, such as, benzyl (Bn), trityl (Tr), 1,1-di-(4'-methoxy phenyl) methyl; silyl, such as, trimethylsilyl (TMS) and tert-butyl dimethylsilyl (TBS), etc. The term "hydroxyl protective group" refers to protective groups adapted to prevent side reaction of hydroxyl group. Representative hydroxyl protective groups comprise, but are not limited to: alkyl, such as, methyl, ethyl and tert-butyl; acyl, such as, alkanoyl (such as, acetyl); aryl methyl, such as, benzyl (Bn), p-methoxybenzyl (PMB), 9-fluorenylmethyl (Fm) and benzhydryl (diphenylmethyl, DPM); silyl, such as, trimethylsilyl (TMS) and tert-butyl dimethylsilyl (TBS), etc.

The compounds of the present invention may be prepared by a variety of synthetic methods well known by persons skilled in the art, including the embodiments as listed below, embodiments of these embodiments in combination with other chemical synthetic methods, as well as equivalence(s) well known by persons skilled in the art. Preferred embodiments comprise, but are not limited to the examples of the present invention.

The solvents as used in the present invention may be commercially available. The following abbreviations are used in the present invention: aq represents aqueous; HATU represents O-(7-azabenzotriazol-1-yl)-N,N,N',N'-tetramethylureahexafluorophosphate; EDC represents N-(3-dimethylaminopropyl)-N'-ethylcarbodiimide hydrochloride; m-CPBA represents 3-chloroperoxybenzoic acid; eq represents equivalent; CDI represents carbonyldiimidazole; DCM represents dichloromethane; PE represents petroleum ether; DIAD represents di-iso-propyl azodicarboxylate; DMF represents N,N-dimethylformamide; DMSO represents dimethylsulfoxide; EtOAc represents ethyl acetate; EtOH represents ethanol; MeOH represents methanol; CBz represents benzyloxycarbonyl, an amino protective group; BOC represents tert-butyloxycarbonyl, an amino protective group; HOAc represents acetic acid; $NaCNBH_3$ represents sodium cyanoborohydride; r.t. represents room temperature; O/N represents overnight; THF represents tetrahydrofuran; $Boc_2O$ represents di-tert-butyloxycarbonyl dicarbonate; TFA represents trifluoroacetic acid; DIPEA represents di-iso-propylethylamine; $SOCl_2$ represents sulfoxide chloride; $CS_2$ represents carbon disulfide; TsOH represents p-toluenesulfonic acid; NFSI represents N-fluoro-N-(benzenesulfonyl)benzenesulfonamide; NCS represents 1-chloro pyrrolidin-2,5-dione; $n-Bu_4NF$ represents tetrabutylammonium fluoride; iPrOH represents 2-propanol; mp represents melting point; LDA represents lithium di-iso-propylamide.

The compounds are named manually or by ChemDraw® software, and the commercially available compounds are named based on the supplier's catalog name.

DETAILED DESCRIPTION

The present invention will be described in detail through the following embodiments, but it is not meant to limit the invention in any undesirable way. The present invention has been described in detail herein, in which the particular embodiments thereof have also been disclosed. It will be apparent to those skilled in the art of various modifications and improvements on the detailed description of the present invention without deviating from the spirit and scope of the present invention.

Reference Example 1: Fragment BB-1

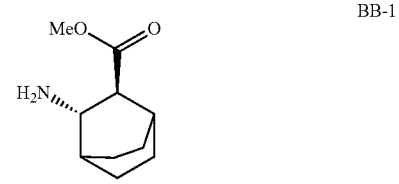 [SMILES: CCOC(=O)[C@H]1C2CCC(CC2)[C@@H]1N]

BB-1

Synthetic Route:

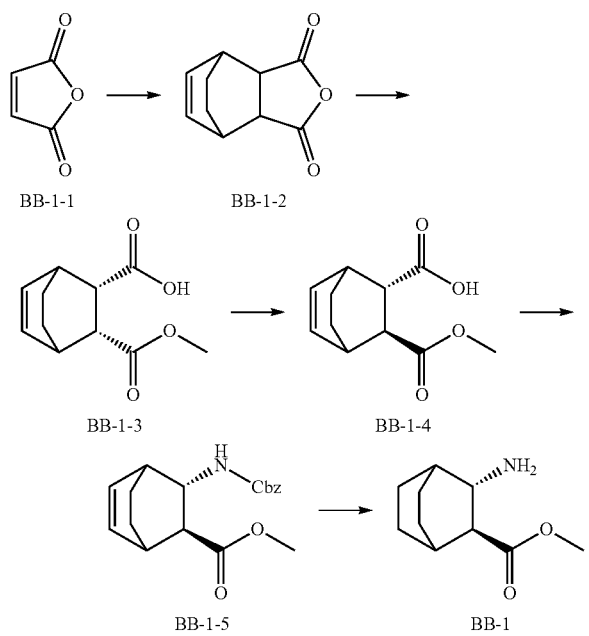

Step 1: Synthesis of Compound BB-1-2

At 0° C., the compound BB-1-1 (100 g, 1 mol) was dissolved in chloroform (1 L), into which was added 1,4-cyclohexadiene (4.32 g, 134.7 mmol) dropwise, the reaction was stirred at room temperature overnight. The reaction was then concentrated at reduced pressure, the resulting solid was stirred with methanol (300 mL), filtered, the filter cake was washed with methanol (100 mL), dried in vacuum to give the compound BB-1-2 (148 g, 0.83 mol, yield 83%).

Step 2: Synthesis of Compound BB-1-3

At −20° C., the compound BB-1-2 (20 g, 112.3 mmol) and quinine (43.7 g, 134.7 mmol) were dissolved in toluene (300 mL), into which was added a solution of anhydrous methanol (4.32 g, 134.7 mmol) in toluene (10 mL) dropwise, the mixture was stirred at −15° C. for 2 hours, the reaction liquid was then reacted at room temperature overnight, with a substantial amount of white solid separated out. To the reaction liquid was added water (100 mL), extracted with ethyl acetate (150 mL×3). The organic phases were combined, washed once with water (100 mL×2) and saturated brine (100 mL), respectively. The organic phases were dried over anhydrous sodium sulfate, filtered, concentrated to give a crude product BB-1-3 (24 g).

Step 3: Synthesis of Compound BB-1-4

At −15° C., potassium tert-pentyloxide (20.2 g, 34 mmol) was dissolved in toluene (320 mL), into which was added a solution of the compound BB-1-3 (24 g, 159.8 mmol) in toluene (20 mL) dropwise, the reaction liquid was stirred at −20° C. for 3 hours. To the reaction liquid was added an aqueous sulphuric acid solution (3 M, 80 mL), extracted with ethyl acetate (300 mL×3). The organic phases were combined, washed with water (100 mL×3), saturated brine (100 mL), respectively. The organic phases were dried over anhydrous sodium sulfate, filtered, and concentrated at reduced pressure. The resultants were purified over a silica gel column (dichloromethane:methanol:acetic acid=200:10:1)) to give BB-1-4 (16 g, 76.11 mmol, yield 66.7%).

Step 4: Synthesis of Compound BB-1-5

At room temperature, to a solution of the compound BB-1-4 (16 g, 76.11 mmol) in toluene (250.00 mL) were added triethylamine (11.55 g, 114.17 mmol, 15.82 mL), diphenyl azidophosphate (25.13 g, 91.3 mmol, 19.8 mL). The mixture was stirred at room temperature for 1 hour, and then reacted at 90° C. for 1 hour. Benzyl alcohol (16.46 g, 152.22 mmol, 15.83 mL) was added into the reaction liquid, stirred at 90° C. for 2 hours. The reaction liquid was diluted with ethyl acetate (500 mL), washed with saturated aqueous solution of sodium carbonate (100 mL×3), saturated brine (100 mL), respectively. The organic phases were dried over anhydrous sodium sulfate, filtered, and concentrated at reduced pressure. The resultants were purified over a silica gel column (petroleum ether:ethyl acetate at 10:1 to 5:1). The resultants were prepared and isolated to give a racemic compound (15 g), which was recrystallized over (n-hexane:dichloromethane=15:1) for 2 times to give the compound BB-1-5 (4 g). MS (ESI) m/z=316.1 [M+1].

Step 5: Synthesis of Compound BB-1

At room temperature, to a solution of the compound BB-1-5 (2 g, 6.34 mmol) in methanol (20.00 mL) and tetrahydrofuran (20 mL) was added palladium on carbon (10%, 0.2 g). The mixture was stirred under hydrogen (50 psi) at 40° C. for 12 hours. The reaction liquid was filtered, and the filtrate was spun to dry to give a crude compound BB-1 (1.1 g). $^1$H NMR (400 MHz, CHLOROFORM-d) δ 3.71 (s, 3H), 3.30-3.35 (m, 1H), 2.75-2.77 (m, 1H), 1.38-1.92 (m, 10H).

Reference Example 2: Fragment BB-2

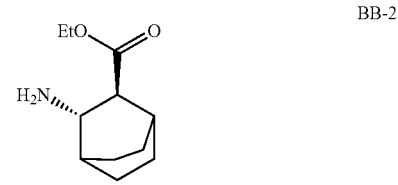

Synthetic Route:

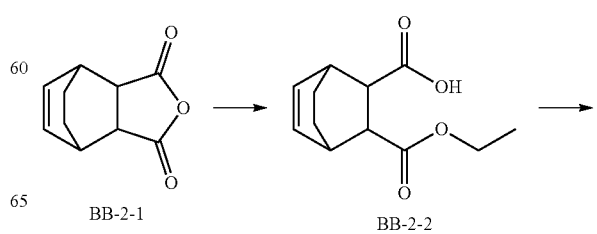

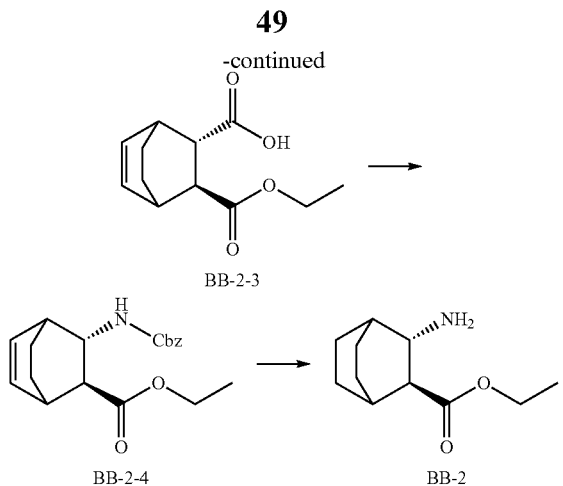

Step 1: Synthesis of Compound BB-2-2

At −16° C. to −12° C., under nitrogen, to a solution of the compound BB-2-1 (92.10 g, 516.89 mmol) and quinine (184.46 g, 568.58 mmol) in toluene (3.4 L) was added anhydrous ethanol (53 mL) dropwise. The mixture was stirred at −16° C. to −12° C. for 12 hours, with a substantial amount of white solid separated out; the reaction liquid was filtered, and the filter cake was dried to give the compound BB-2-2 (160.00 g, 291.61 mmol, yield 56.42%).

Step 2: Synthesis of Compound BB-2-3

At room temperature, to a solution of the compound BB-2-2 (160.00 g, 291.61 mmol) in toluene (900.00 mL) was added hydrochloric acid (97.2 mL, 6 M). The mixture was stirred at room temperature for 30 minutes, the reaction liquid was left to separate, the water phase was extracted with toluene (550.00 mL) once again, and the organic phases were combined. At −20° C., potassium tert-pentyloxide (42.3 g) was dissolved in toluene (400 mL), which was added into the organic phase dropwise for 30 minutes; a second batch of potassium tert-pentyloxide (9.8 g) was dissolved in toluene (100 mL), which was added into the organic phase dropwise. The mixed liquid was stirred at −20° C. under nitrogen for 3 hours. The reaction was quenched with hydrochloric acid (100 mL, 6 M) while keeping the temperature at −20° C., and into which was added acetic acid (8 g). The reaction was heated to −5° C., into which was added hydrochloric acid (60 mL, 2M). It was stirred at about −5° C. for 45 minutes, and then heated to about 20° C. with stirring for 15 minutes. The mixed liquid was left, the water phase was removed, into the organic phase was added water (35 mL) with stirring for 15 minutes, after which it was left for 15 minutes, removing the water phase. A buffer solution (135 mL) (22.05 g sodium dihydrogen phosphate, 3.6 g disodium hydrogen phosphate dissolved in 405 mL water) was added into the organic phase, which was stirred for 15 minutes, left for 15 minutes, removing the water phase, and being washed for three times. The organic phases were spun to dry, into which was added n-heptane (50 mL) while keeping at 40° C. for 30 minutes, cooled to 0-5° C. with stirring for 1.5 hours. The mixture was filtered. The filter cake was dried, crystallized for three times repeatedly, to give the compound BB-2-3 (28.00 g, 124.86 mmol, yield 43.08%).

Step 3: Synthesis of Compound BB-2-4

At room temperature, to a solution of the compound BB-2-3 (25.00 g, 111.48 mmol) in toluene (300.00 mL) was added triethylamine (27.07 g, 267.55 mmol, 37.08 mL). The reaction liquid was heated to 95° C. and into which was added diphenyl azidophosphate (30.37 g, 110.37 mmol, 23.91 mL). The mixture was stirred at 95° C. for 1 hour, benzyl alcohol (12.06 g, 111.48 mmol, 11.60 mL) was added into the reaction liquid and stirred at 95° C. under nitrogen for 12 hours. The reaction liquid was cooled to room temperature, and concentrated at reduced pressure to give a crude product, which was purified over a silica gel chromatographic column (petroleum ether:ethyl acetate=6:1) to give the compound BB-2-4 (32.00 g, 72.08 mmol, yield 64.66%). MS (ESI) m/z=330.0 [M+1]. $^1$H NMR (400 MHz, CHLOROFORM-d) δ 7.28-7.42 (m, 5H), 6.47 (t, J=7.40 Hz, 1H), 6.19 (t, J=7.15 Hz, 1H), 5.01-5.17 (m, 2H), 4.07-4.39 (m, 4H), 2.69-2.94 (m, 2H), 2.12 (br s, 1H), 1.46-1.78 (m, 2H), 0.99-1.35 (m, 7H).

Step 4: Synthesis of Compound BB-2

At room temperature and under nitrogen, to a solution of the compound BB-2-4 (31.00 g, 94.11 mmol) in ethanol (300.00 mL) and tetrahydrofuran (200 mL) was added palladium on carbon (10%, 5 g). After hydrogen replacement for 3 times, the mixture was then stirred under hydrogen (50 psi) for 12 hours. The reaction liquid was filtered, and the filtrate was spun to dry to give the crude compound BB-2 (18.30 g).

$^1$H NMR (400 MHz, DMSO-$d_6$) δ 7.28-7.34 (m, 1H), 3.97-4.17 (m, 2H), 3.40-3.52 (m, 1H), 3.44 (q, J=6.86 Hz, 1H), 2.09 (br d, J=6.27 Hz, 1H), 1.75-1.87 (m, 2H), 1.24-1.61 (m, 8H), 1.18 (t, J=7.15 Hz, 3H), 1.06 (t, J=7.03 Hz, 1H).

Reference Example 3: Fragment BB-3

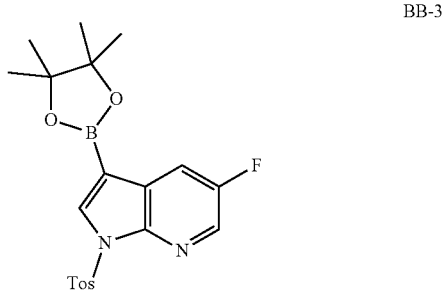

Synthetic Route:

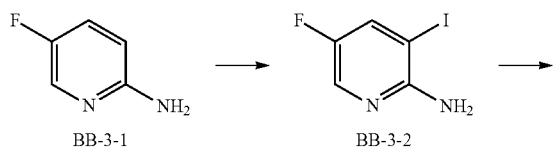

-continued

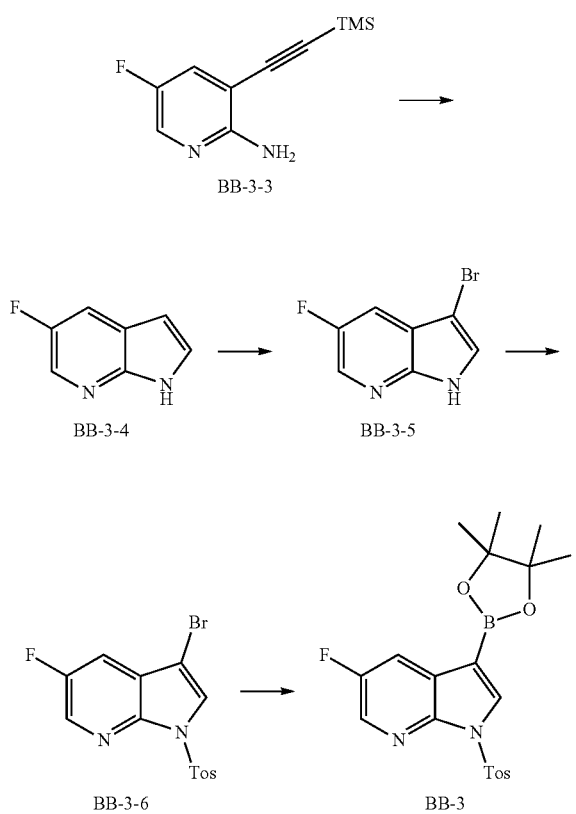

Step 1: Synthesis of Compound BB-3-2

To a sulfuric acid solution (100.00 mL, 2 mol) of compound BB-3-1 (18.00 g, 160.57 mmol, 1.00 eq) was added potassium iodate (17.18 g, 80.29 mmol, 17.18 mL). The mixture was heated to 100° C. with stirring, into which was added potassium iodide (14.66 g, 88.31 mmol) in water (40.00 mL) dropwise and stirred at 100° C. for additional one hour. The reaction liquid was cooled to room temperature and adjusted to neutral with saturated sodium carbonate solution, extracted with ethyl acetate (200 mL) for three times. The organic phases were dried over anhydrous sodium sulfate, filtered, and concentrated to give a crude product, which was purified by silica gel column chromatography (petroleum ether:ethyl acetate=20:1 to 10:1) to give the compound BB-3-2 (18.00 g, 75.18 mmol, yield 46.82%). MS (ESI) m/z: 239.0 [M+1].

Step 2: Synthesis of Compound BB-3-3

At room temperature, to a solution of the compound BB-3-2 (18.00 g, 75.63 mmol) and trimethyl silyl acetylene (14.86 g, 151.26 mmol, 20.93 mL) in tetrahydrofuran (250.00 mL) were added cuprous iodide (696.18 mg, 3.66 mmol), dichlorobis(triphenylphosphine)palladium (II) (1.59 g, 2.27 mmol), triethylamine (22.96 g, 226.89 mmol, 31.45 mL). The reaction liquid was stirred at room temperature for 3 hours. The reaction liquid was filtered, and the filtrate was spun to dry to give the crude product, which was purified by silica gel column chromatography (petroleum ether:ethyl acetate=20:1 to 10:1) to give the crude compound BB-3-3 (17.00 g, 81.20 mmol). MS (ESI) m/z: 209.00 [M+1].

Step 3: Synthesis of Compound BB-3-4

At room temperature, to a solution of the compound BB-3-3 (17.00 g, 81.61 mmol) in 1-methyl-2-pyrrolidone (200.00 mL) was added sodium-hydrogen (3.92 g, 97.93 mmol, 60%) slowly. The mixture was stirred at 80° C. for 1 hour. The reaction liquid was cooled to room temperature, into which was added water (100 mL) slowly, and extracted with ethyl acetate (100 mL) for three times. The organic phases were combined, washed with saturated brine (100 mL) for three times, dried over anhydrous sodium sulfate, filtered, and concentrated at reduced pressure. The resulting crude product was purified by silica gel column chromatography (petroleum ether:ethyl acetate=10:1 to 5:1) to give the compound BB-3-4 (9.30 g, 58.48 mmol, yield 71.66%). MS (ESI) m/z=136.8 [M+1].

Step 4: Synthesis of Compound BB-3-5

At −10° C., to a solution of the compound BB-3-4 (7.40 g, 54.36 mmol) in DMF (100.00 mL) was added N-bromosuccinimide (9.67 g, 54.36 mmol). The mixture was stirred at −10° C. for one hour. Water (100 mL) was added dropwise into the reaction liquid, the mixture was filtered, and the solid was spun to dry to give the compound BB-3-5 (11.50 g, 44.34 mmol, yield 81.56%). MS (ESI) m/z=217.0 [M+1].

Step 5: Synthesis of Compound BB-3-6

At 0° C., to a solution of the compound BB-3-5 (9.80 g, 45.58 mmol) in tetrahydrofuran (150.00 mL) was added sodium-hydrogen (2.19 g, 54.69 mmol, 60%). The reaction liquid was stirred at 15° C. for 30 minutes. P-toluene sulfonyl chloride (10.43 g, 54.69 mmol) was added into the reaction liquid, which was stirred at 15° C. for 12 hours. To the reaction liquid was added water (100 mL) dropwise, extracted with ethyl acetate (150 mL) for three times. The organic phases were combined, dried over anhydrous sodium sulfate, filtered, and concentrated at reduced pressure. The resulting crude product was purified over a silica gel chromatographic column (petroleum ether:ethyl acetate=50:1 to 20:1) to give the compound BB-3-6 (15.00 g, 40.63 mmol, yield 89.13%). MS (ESI) m/z=370.7 [M+1].

Step 6: Synthesis of Compound BB-3

At room temperature, to a solution of the compound BB-3-6 (15.00 g, 40.63 mmol) and bis(pinacolato)diboron (12.38 g, 48.75 mmol) in 1,4-dioxane (80.00 mL) were added the compound potassium acetate (5.98 g, 60.94 mmol) and palladium 1′-bis(di-tert-butylphosphine) ferrocene dichloride (1.32 g, 2.03 mmol). The mixture was stirred at 40° C. under nitrogen for 12 hours. The crude product was filtered, and the filtrate was diluted with ethyl acetate (150 mL), the organic phases were washed with brine (50 mL) for two times, combined, dried over anhydrous sodium sulfate, filtered, and concentrated at reduced pressure. The resulting crude product was purified over a silica gel chromatographic column (petroleum ether:ethyl acetate=1:0 to 20:1) to give the compound BB-3 (4.80 g, 6.71 mmol, yield 16.52%). $^1$H NMR (400 MHz, DMSO-$d_6$) δ 8.42 (d, J=1.2 Hz, 1H), 8.15 (s, 1H), 7.97-8.07 (m, 2H), 7.84-7.87 (m, 1H), 7.43 (d, J=8.4 Hz, 1H), 2.35 (s, 1H), 1.32 (s, 1H). MS (ESI) m/z: 417.0 [M+1].

Reference Example 4: Fragment BB-4

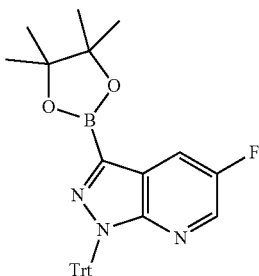

Synthetic Route:

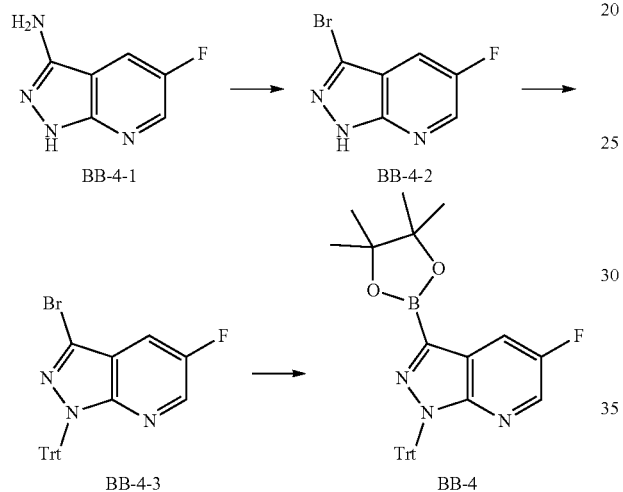

Step 1: Synthesis of Compound BB-4-2

To a solution of the compound BB-4-1 (300 mg, 1.97 mmol) in bromoform (5 mL) was added tert-butyl nitrite (406 mg, 3.94 mmol). The mixture was stirred at 60° C. for 1 hour, and then stirred at 90° C. for 1 hour. The reaction liquid was cooled to room temperature, and then concentrated to give a crude product, which was purified over a flash silica gel chromatographic column (5-20% ethyl acetate/petroleum ether) to give the compound BB-4-2 (300.00 mg, yield 70.50%). $^1$H NMR (400 MHz, CHLOROFORM-d) δ: 11.25 (br s, 1H), 8.54 (dd, J=1.88, 2.64 Hz, 1H), 7.69 (dd, J=2.51, 7.28 Hz, 1H). MS (ESI) m/z: 215.9 (M+H$^+$).

Step 2: Synthesis of Compound BB-4-3

To a solution of the compound BB-4-2 (300 mg, 1.39 mmol) in N,N-dimethyl formamide (5 mL) was added triphenyl chloromethane (426 mg, 1.53 mmol) and potassium carbonate (576 mg, 4.17 mmol). The mixture was stirred at 25° C. for 12 hours. The reaction liquid was diluted with ethyl acetate (50 mL), and washed with saturated brine (15 mL×3). The organic phases were dried over anhydrous sodium sulfate, and concentrated to give a crude product, which was purified over a flash silica gel chromatographic column (0~10% ethyl acetate/petroleum ether) to give the compound BB-4-3 (350 mg, yield 54.94%). $^1$H NMR (400 MHz, CHLOROFORM-d) δ: 8.16 (dd, J=1.25, 2.76 Hz, 1H), 7.53 (dd, J=3.01, 7.53 Hz, 1H), 7.25 (s, 15H). MS (ESI) m/z: 458.2 (M+H$^+$).

Step 3: Synthesis of Compound BB-4

To a solution of the compound BB-4-3 (350 mg, 763.66 umol) and bis(pinacolato)diboron (291 mg, 1.15 mmol) in N,N-dimethyl formamide (7 mL) were added potassium acetate (225 mg, 2.29 mmol) and palladium 1'-bis(di-tert-butylphosphine)ferrocene dichloride (28 mg, 38.18 umol). The mixture was stirred at 100° C. under nitrogen for 2 hours. The reaction liquid was cooled to room temperature, and then filtered. The filtrate was diluted with ethyl acetate (50 mL), washed with saturated brine (20 mL×3). The organic phases were dried over anhydrous sodium sulfate, and concentrated to give a crude product, which was purified over a flash silica gel chromatographic column (0~10% ethyl acetate/petroleum ether) to give BB-4 (300 mg, yield 77.73%). MS (ESI) m/z: 733.2 (M+Na$^+$).

Reference Example 5: Fragment BB-5

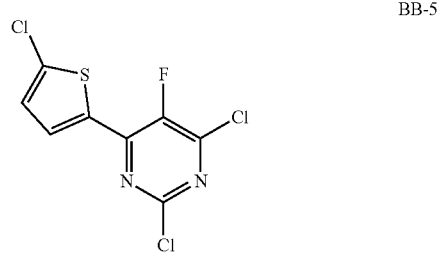 [SMILES: Fc1c(Cl)nc(Cl)nc1-c1ccc(Cl)s1]

Synthetic Route:

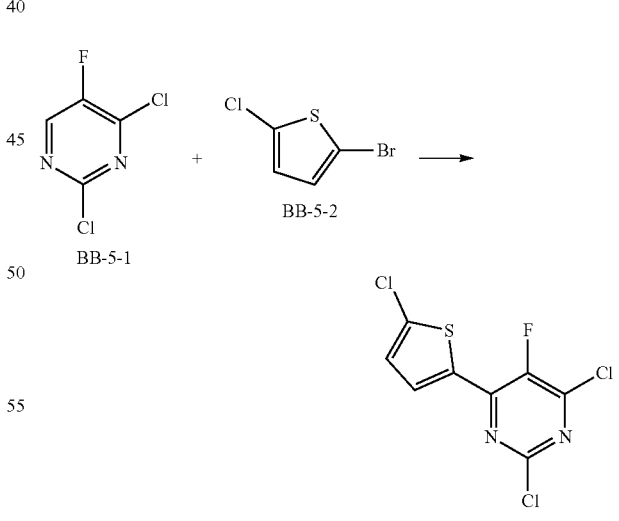

Step 1: Synthesis of Compound BB-5

At −70° C., the compound BB-5-2 (201.06 mg, 1.02 mmol) was dissolved in a tetrahydrofuran solution (3.00 mL), into which was added n-butyllithium (2.5 M, 409.65 uL) under nitrogen, and the reaction liquid was stirred under nitrogen for 15 minutes, into which was then added a solution of 2,4-dichloro-5-fluoropyrimidine (100.00 mg, 598.91 umol) in ethylene glycol dimethyl ether (1.00 mL) dropwise, and stirred for 3 hours. The reaction liquid was quenched with an aqueous solution of ammonium chloride, and extracted with ethyl acetate (20 mL×2). The organic phases were concentrated at reduced pressure. The crude product was dissolved in tetrahydrofuran (2 mL), into which was added a solution of 2,3-dichloro-5,6-dicyano-1,4-benzoquinone (149.55 mg, 658.80 umol) in tetrahydrofuran (1 mL), and reacted at 20° C. for 5 hours. The reaction liquid was concentrated at reduced pressure, and the crude product was purified over a silica gel column (petroleum ether:ethyl acetate=10:1) to give BB-5 (80.00 mg, yield 47.11%). $^1$H NMR (400 MHz, CHLOROFORM-d) δ 7.72 (dd, J=1.38, 4.14 Hz, 1H), 6.98 (d, J=4.27 Hz, 1H).

Reference Example 6: Fragment BB-6

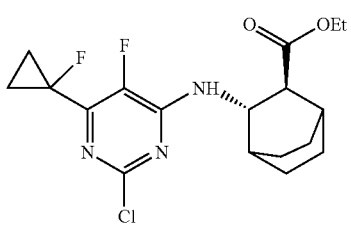

Synthetic Route:

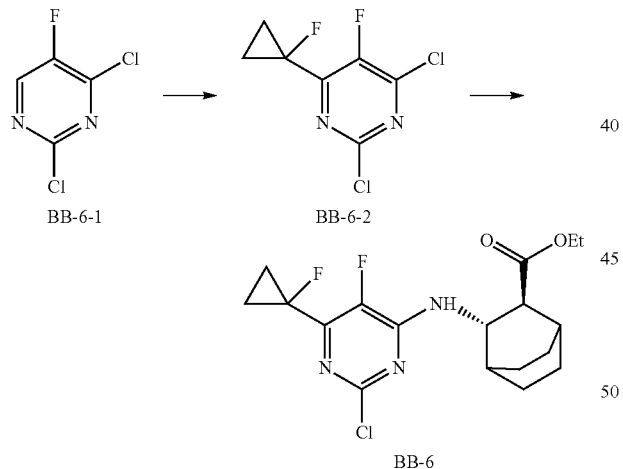

Step 1: Synthesis of Compound BB-6-2

At room temperature, the compound 2,4-dichloro-5-fluoropyrimidine (350.00 mg, 2.10 mmol) was dissolved in acetonitrile (5.00 mL) and water (5.00 mL), into which was added silver nitrate (713.45 mg, 4.20 mmol), 1-fluorocyclopropyl carboxylic acid (649.15 mg, 6.24 mmol), respectively. The reaction liquid was heated to 80° C., into which was then added a solution of ammonium persulfate (958.44 mg, 4.20 mmol) in water (1 mL) dropwise, and the reaction liquid was reacted at 80° C. overnight. The reaction liquid was cooled to room temperature, into which were added ethyl acetate (100 mL) and brine (100 mL). The floccules was filtered, and the organic layer was washed with water (30 mL×3) and brine (30 mL) respectively, dried over sodium sulfate, filtered, and concentrated at reduced pressure. The crude product was purified over a silica gel column (petroleum ether:ethyl acetate 1:0 to 10:1) to give the compound BB-6-2 (260 mg, yield 55%). $^1$H NMR (400 MHz, CHLOROFORM-d) δ 1.48-1.60 (m, 4H).

Step 2: Synthesis of Compound BB-6

At room temperature, the compound BB-6-2 (100.00 mg, 444.40 umol) was dissolved in tetrahydrofuran (5 mL), into which were added BB-2 (92.05 mg, 466.63 umol) and N,N-diisopropyl ethylamine (172.30 mg, 1.33 mmol), respectively. The reaction liquid was heated to 50° C. overnight. The reaction liquid was concentrated at reduced pressure. The crude product was purified over a silica gel column (petroleum ether:ethyl acetate 10:1 to 3:1) to give the compound BB-6 (149.00 mg, yield 79.08%). MS (ESI) m/z: 386.0 (M+1$^+$).

Following the synthetic process in steps 1~2 of Reference example 6, each reference example in the table below was synthesized.

| Reference example No. | Structure | MS + 1 |
|---|---|---|
| BB-7 | 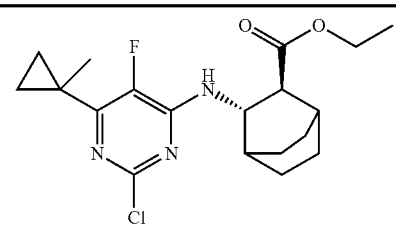 | 382.1 |
| BB-8 | 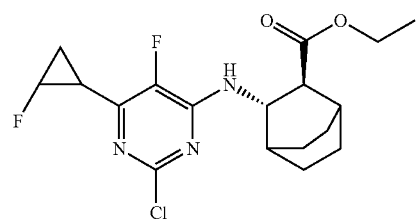 [SMILES: CCOC(=O)[C@H]1C2CCC(CC2)[C@@H]1Nc1nc(Cl)nc(C2CC2F)c1F] | 386.1 |
| BB-9 | 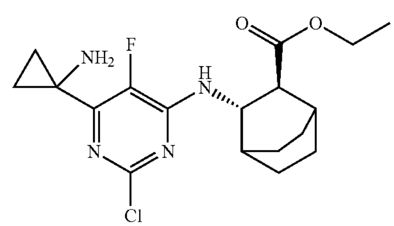 [SMILES: CCOC(=O)[C@H]1C2CCC(CC2)[C@@H]1Nc1nc(Cl)nc(C2(N)CC2)c1F] | 383.1 |
| BB-10 | 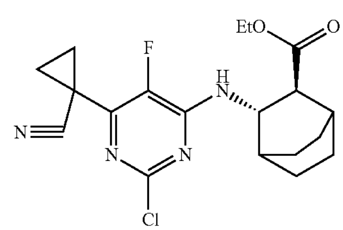 [SMILES: CCOC(=O)[C@H]1C2CCC(CC2)[C@@H]1Nc1nc(Cl)nc(C2(C#N)CC2)c1F] | 393.1 |

Example 1

WX-230

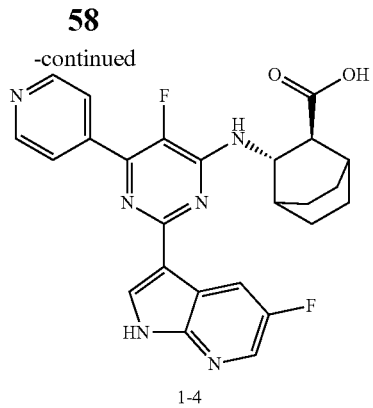

Synthetic Route:

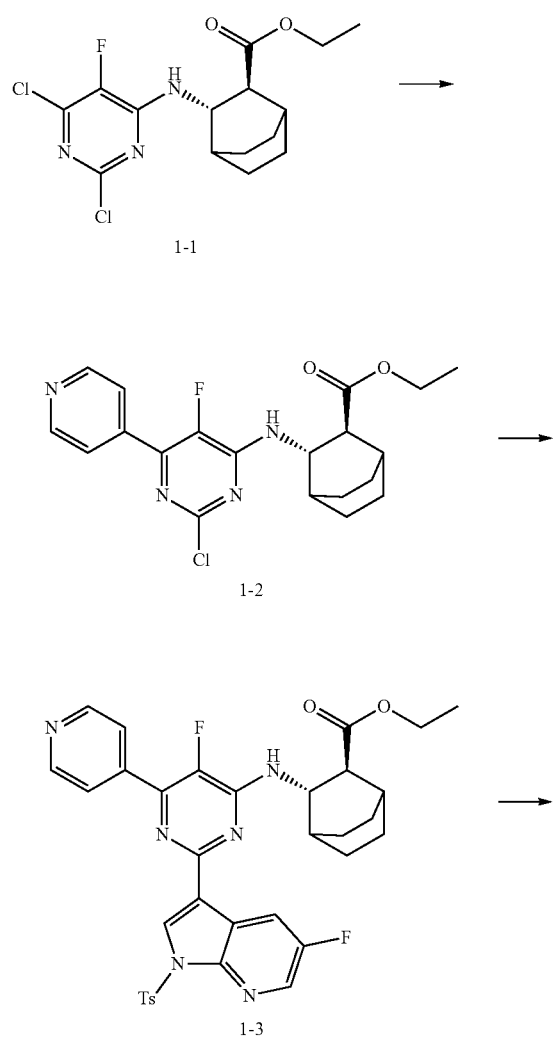

Step 1: Synthesis of Compound 1-2

To a solution of the compound 1-1 (100 mg, 276 umol) and 4-boronic acid pyridine (41 mg, 331 umol) in tetrahydrofuran (2 mL) and water (0.5 mL) were added potassium phosphate (117.20 mg, 552.14 umol), Pd(dtbpf)Cl$_2$ (9 mg, 14 umol). The mixture was stirred at 25° C. for 12 hours, and then stirred at 50° C. for 2 hours. The reaction liquid was cooled to room temperature, and then was filtered. To the filtrate was added water (30 mL), extracted with ethyl acetate (10 mL) for three times. The organic phases were combined, dried over anhydrous sodium sulfate, and concentrated at reduced pressure to give a crude product, which was purified over a flash silica gel chromatographic column (10-30% ethyl acetate/petroleum ether) to give the compound 1-2 (30.00 mg, yield 26.84%). MS (ESI) m/z: 405.1 (M+H$^+$).

Step 2: Synthesis of Compound 1-3

To a solution of the compound 1-2 (30 mg, 74 umol) and the compound BB-3 (37 mg, 89 umol) in 2-methyl tetrahydrofuran (2.00 mL) and water (0.2 mL) were added potassium phosphate (31.46 mg, 148 umol), tri(dibenzylidene acetone)dipalladium (3 mg, 4 umol) and 2-dicyclohexylphosphine-2',4',6'-triisopropyl biphenyl (7 mg, 15 umol). The mixture was stirred at 80° C. and under nitrogen for 12 hours. The reaction liquid was cooled to room temperature, and then was filtered. To the filtrate was added water (20 mL), extracted with ethyl acetate (8 mL×3). The organic phases were combined, dried over anhydrous sodium sulfate, and concentrated to give a crude product. It was purified over a flash silica gel chromatographic column (10-30% ethyl acetate/petroleum ether) to give the compound 1-3 as a yellow solid (20 mg, yield 40.97%). MS (ESI) m/z: 659.2 (M+H$^+$).

Step 3: Synthesis of Compound WX-230

To a solution of the compound 1-3 (20.00 mg, 30.36 umol) in tetrahydrofuran (1.00 mL) and water (0.25 mL) was added NaOH (6.07 mg, 151.80 umol). The mixture was stirred at 50° C. for 12 hours. Tetrahydrofuran was removed by concentration, into which was added 1 M HCl (0.5 mL), the crude product was prepared and purified to give the compound WX-230 (10 mg, yield 64.21%). $^1$H NMR (400 MHz, METHANOL-d$_4$) δ 9.04 (br d, J=6.52 Hz, 2H), 8.77 (br d, J=6.53 Hz, 3H), 8.48 (s, 1H), 8.31 (br s, 1H), 4.81 (br s, 1H), 2.84 (br d, J=6.53 Hz, 1H), 2.14 (br s, 1H), 2.06 (br s, 1H), 1.81-2.00 (m, 3H), 1.64-1.80 (m, 3H), 1.56 (br d, J=12.05 Hz, 3H). MS (ESI) m/z: 477.1 (M+H$^+$).

Following the synthetic process in steps 1-3 of Example 1, each example in the table below was synthesized.

| Compound No. | Compound Structure | MS + 1 | 1HNMR (Resolution) |
|---|---|---|---|
| WX-231 | 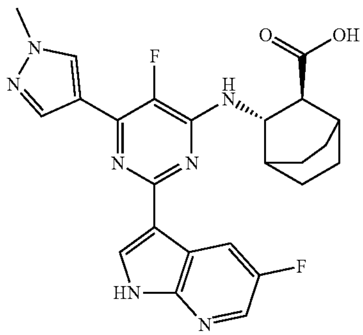 [SMILES: Cn1cc(-c2nc(-c3c[nH]c4ncc(F)cc34)nc(N[C@H]3C4CCC(CC4)[C@@H]3C(=O)O)c2F)cn1] | 480.2 | $^1$H NMR (400 MHz, METHANOL-d$_4$) δ 8.73 (s, 1H), 8.57 (br d, J = 9.29 Hz, 1H), 8.49 (br s, 1H), 8.24 (s, 1H), 5.15 (br d, J = 7.03 Hz, 1H), 4.05 (s, 3H), 2.94 (br d, J = 6.78 Hz, 1H), 2.20 (br s, 1H), 2.04 (br s, 1H), 1.52-2.00 (m, 8H) |
| WX-236 | 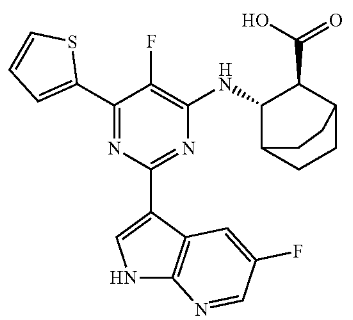 [SMILES: O=C(O)[C@H]1C2CCC(CC2)[C@@H]1Nc1nc(-c2c[nH]c3ncc(F)cc23)nc(-c2cccs2)c1F] | 482.1 | $^1$H NMR (400 MHz, DMSO-d6) δ 12.30 (br d, J = 2.26 Hz, 1H), 8.59 (dd, J = 2.76, 10.04 Hz, 1H), 8.14-8.35 (m, 2H), 7.80-7.94 (m, 2H), 7.67 (br d, J = 6.53 Hz, 1H), 7.30 (dd, J = 3.89, 4.89 Hz, 1H), 4.56-4.78 (m, 1H), 2.85 (br d, J = 6.78 Hz, 1H), 1.98 (br d, J = 14.56 Hz, 2H), 1.37-1.84 (m, 8H). |
| WX-240 | 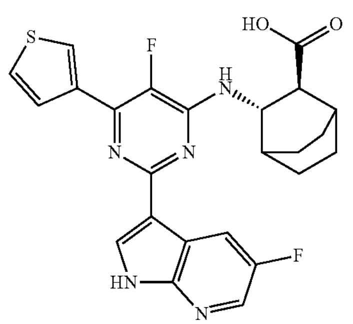 [SMILES: O=C(O)[C@H]1C2CCC(CC2)[C@@H]1Nc1nc(-c2c[nH]c3ncc(F)cc23)nc(-c2ccsc2)c1F] | 482.1 | $^1$H NMR (400 MHz, DMSO-d6) δ 12.33 (br s, 1H), 8.55 (dd, J = 2.76, 9.79 Hz, 1H), 8.15-8.35 (m, 3H), 7.66-7.86 (m, 2H), 7.34 (br d, J = 5.77 Hz, 1H), 4.64-4.85 (m, 1H), 1.99 (br s, 2H), 1.51-1.83 (m, 7H), 1.23-1.48 (m, 4H). |
| WX-245 | 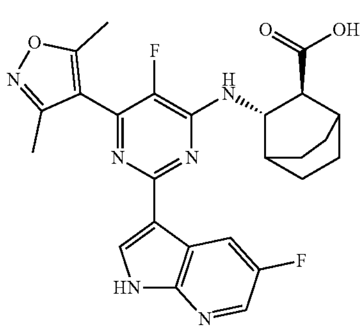 [SMILES: Cc1noc(C)c1-c1nc(-c2c[nH]c3ncc(F)cc23)nc(N[C@H]2C3CCC(CC3)[C@@H]2C(=O)O)c1F] | 495.2 | $^1$H NMR (400 MHz, METHANOL-d$_4$) δ 8.62 (dd, J = 2.89, 9.41 Hz, 1H), 8.27 (s, 1H), 8.16-8.21 (m, 1H), 4.94 (br d, J = 7.03 Hz, 1H), 2.80 (br d, J = 6.78 Hz, 1H), 2.52 (d, J = 1.25 Hz, 3H), 2.39 (s, 3H), 2.12 (br s, 1H), 2.07 (br s, 1H), 1.80-2.02 (m, 3H), 1.62-1.79 (m, 3H), 1.55 (br d, J = 11.29 Hz, 2H) |

-continued

| Compound No. | Compound Structure | MS + 1 | 1HNMR (Resolution) |
|---|---|---|---|
| WX-247 | 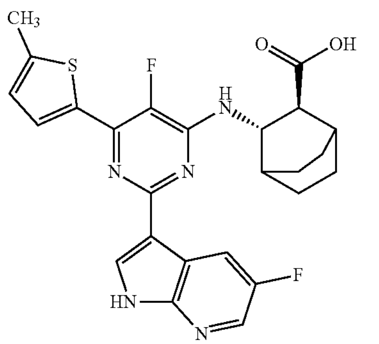 [SMILES: Cc1ccc(-c2nc(-c3c[nH]c4ncc(F)cc34)nc(N[C@H]3C4CCC(CC4)[C@@H]3C(=O)O)c2F)s1] | 496.1 | ¹H NMR (400 MHz, METHANOL-d4) δ 8.80-8.82 (m, 1 H), 8.18 (s, 1 H), 8.10-8.11 (m, 1 H), 7.63-7.64 (m, 1 H), 6.78-6.79 (m, 1 H), 4.67 (d, J = 6.4 Hz, 1 H), 2.71 (d, J = 6.4 Hz, 1 H), 2.54 (s, 3 H), 1.36-2.05 (m, 10 H). |
| WX-249 | 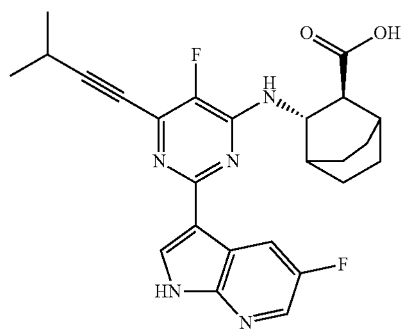 [SMILES: CC(C)C#Cc1nc(-c2c[nH]c3ncc(F)cc23)nc(N[C@H]2C3CCC(CC3)[C@@H]2C(=O)O)c1F] | 466.2 | ¹H NMR (400 MHz, METHANOL-d4) δ 8.61 (dd, J = 2.76, 9.54 Hz, 1H), 8.33 (s, 1H), 8.20 (s, 1H), 4.95 (br d, J = 6.78 Hz, 1H), 2.95 (td, J = 6.71, 13.68 Hz, 1H), 2.82 (br d, J = 7.03 Hz, 1H), 2.13 (br s, 1H), 2.02 (br s, 1H), 1.90-2.00 (m, 1H), 1.80-1.88 (m, 2H), 1.62-1.78 (m, 3H), 1.48-1.61 (m, 2H), 1.34 (d, J = 6.78 Hz, 6H). |
| WX-254 | 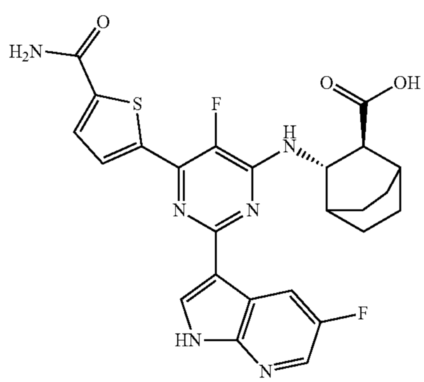 [SMILES: NC(=O)c1ccc(-c2nc(-c3c[nH]c4ncc(F)cc34)nc(N[C@H]3C4CCC(CC4)[C@@H]3C(=O)O)c2F)s1] | 507.1 | ¹H NMR (400 MHz, METHANOL-d4) δ 8.39-8.43 (m, 1 H), 8.03-8.10 (m, 2 H), 7.70-7.71 (m, 1 H), 7.60-7.61 (m, 1 H), 4.74-4.76 (m, 1 H), 2.76-2.77 (m, 1 H), 1.29-2.10 (m, 10 H). |
| WX-258 | 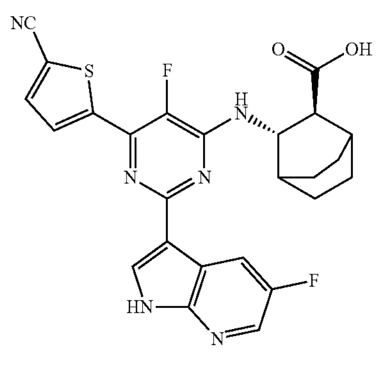 [SMILES: N#Cc1ccc(-c2nc(-c3c[nH]c4ncc(F)cc34)nc(N[C@H]3C4CCC(CC4)[C@@H]3C(=O)O)c2F)s1] | 525.1 | ¹H NMR (400 MHz, METHANOL-d4) δ 8.63-8.66 (m, 1 H), 8.24 (s, 1 H), 8.13-8.14 (m, 1 H), 7.74-7.78 (m, 2 H), 4.80-4.82 (m, 1 H), 2.76-2.78 (m, 1 H), 1.29-2.09 (m, 10 H). |

| Compound No. | Compound Structure | MS + 1 | 1HNMR (Resolution) |
|---|---|---|---|
| WX-260 | 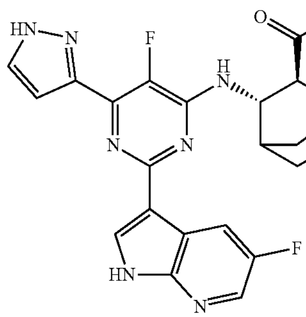 | 466.2 | ¹H NMR (400 MHz, METHANOL-d4) δ 8.50 (dd, J = 2.51, 9.29 Hz, 1H), 8.42 (s, 1H), 8.33 (s, 1H), 7.00 (d, J = 6.78 Hz, 1H), 5.60 (d, J = 6.78 Hz, 1H), 5.07 (br d, J = 6.53 Hz, 1H), 4.11 (s, 3H), 2.88 (br d, J = 6.78 Hz, 1H), 2.17 (br s, 1H), 2.01 (br s, 1H), 1.50-1.98 (m, 8H). |
| WX-263 | 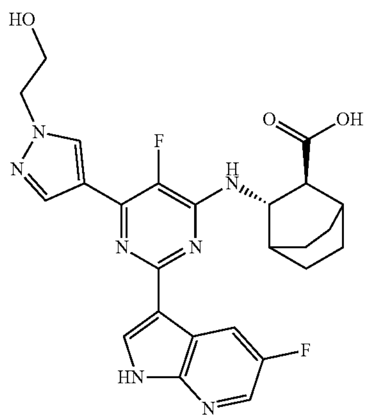 [SMILES: O=C(O)[C@H]1C2CCC(CC2)[C@@H]1Nc1nc(-c2c[nH]c3ncc(F)cc23)nc(-c2cnn(CCO)c2)c1F] | 510.1 | ¹H NMR (400 MHz, METHANOL-d4) δ 8.60-8.57 (m, 1 H), 8.26 (s, 1 H), 8.21-8.20 (m, 1 H), 8.10-8.09 (m, 2 H), 4.83-4.81 (m, 1 H), 4.32 (t, J = 4.8 Hz, 2 H), 3.95 (t, J = 5.2 Hz, 2 H), 2.75-2.73 (m, 1 H), 2.10-1.50 (m, 10 H). |
| WX-275 | 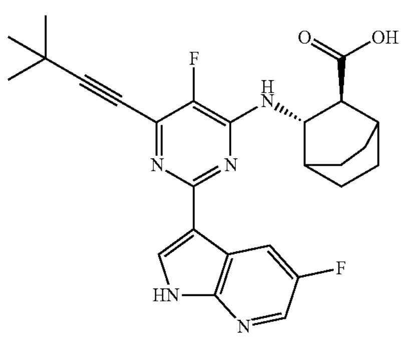 [SMILES: CC(C)(C)C#Cc1nc(-c2c[nH]c3ncc(F)cc23)nc(N[C@H]2C3CCC(CC3)[C@@H]2C(=O)O)c1F] | 480.2 | ¹H NMR (400 MHz, METHANOL-d4) δ 8.63 (dd, J = 2.64, 9.41 Hz, 1H), 8.28 (s, 1H), 8.17 (s, 1H), 4.90-4.93 (m, 1H), 2.79 (br d, J = 6.53 Hz, 1H), 2.12 (br s, 1H), 2.02 (br s, 1H), 1.89-2.00 (m, 1H), 1.78-1.89 (m, 2H), 1.61-1.77 (m, 3H), 1.53 (br d, J = 13.30 Hz, 2H), 1.39 (s, 9H). |
| WX-276 | 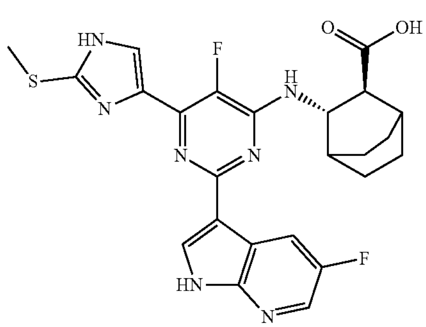 [SMILES: CSc1nc(-c2nc(-c3c[nH]c4ncc(F)cc34)nc(N[C@H]3C4CCC(CC4)[C@@H]3C(=O)O)c2F)c[nH]1] | 512.1 | N/A |

| Compound No. | Compound Structure | MS + 1 | 1HNMR (Resolution) |
|---|---|---|---|
| WX-278 | 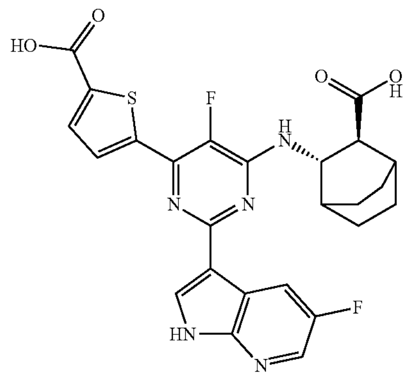 [SMILES: O=C(O)c1ccc(-c2nc(-c3c[nH]c4ncc(F)cc34)nc(N[C@H]3C4CCC(CC4)[C@@H]3C(=O)O)c2F)s1] | 526.1 | $^1$H NMR (400 MHz, METHANOL-d4) δ 8.67 (s, 1 H), 8.16-8.27 (m, 2 H), 7.82 (s, 2 H), 5.34 (s, 1 H), 2.76 (s, 1 H), 1.53-2.11 (m, 10 H). |
| WX-279 | 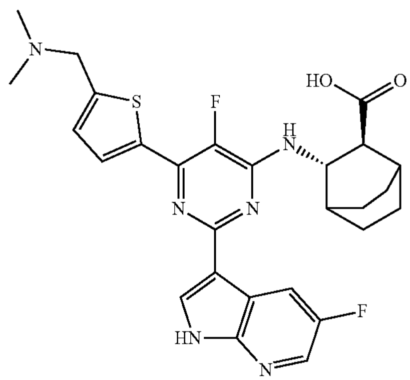 [SMILES: CN(C)Cc1ccc(-c2nc(-c3c[nH]c4ncc(F)cc34)nc(N[C@H]3C4CCC(CC4)[C@@H]3C(=O)O)c2F)s1] | 539.1 | $^1$H NMR (400 MHz, DMSO-d6) δ 12.36 (br d, J = 2.51 Hz, 1H), 9.92 (br s, 1H), 8.56 (dd, J = 2.89, 9.66 Hz, 1H), 8.15-8.38 (m, 2H), 7.69-7.94 (m, 2H), 7.46 (d, J = 3.76 Hz, 1H), 4.53-4.81 (m, 3H), 2.75-2.95 (m, 7H), 1.99 (br d, J = 18.32 Hz, 2H), 1.34-1.84 (m, 8H). |
| WX-281 | 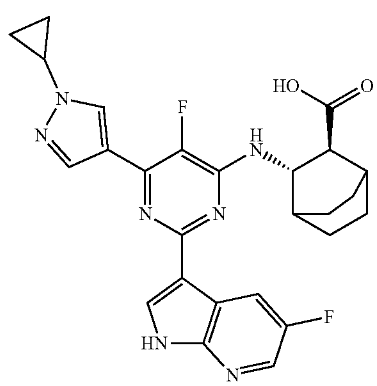 [SMILES: O=C(O)[C@H]1C2CCC(CC2)[C@@H]1Nc1nc(-c2c[nH]c3ncc(F)cc23)nc(-c2cnn(C3CC3)c2)c1F] | 506.1 | $^1$H NMR (400 MHz, DMSO-d6) δ 12.36 (br d, J = 2.51 Hz, 1H), 9.92 (br s, 1H), 8.56 (dd, J = 2.89, 9.66 Hz, 1H), 8.15-8.38 (m, 2H), 7.69-7.94 (m, 2H), 7.46 (d, J = 3.76 Hz, 1H), 4.53-4.81 (m, 3H), 2.75-2.95 (m, 7H), 1.99 (br d, J = 18.32 Hz, 2H), 1.34-1.84 (m, 8H). |
| WX-283 | 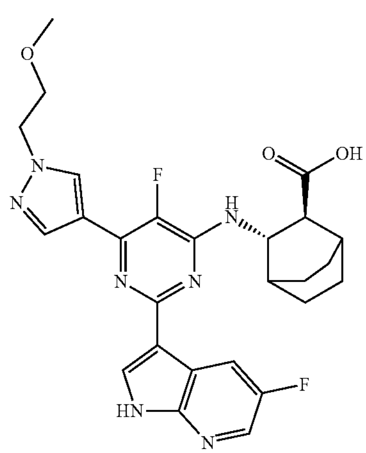 [SMILES: COCCn1cc(-c2nc(-c3c[nH]c4ncc(F)cc34)nc(N[C@H]3C4CCC(CC4)[C@@H]3C(=O)O)c2F)cn1] | 524.2 | $^1$H NMR (400 MHz, METHANOL-d4) δ 8.40- 8.41(m, 2 H), 8.29 (s, 1 H), 8.13 (s, 1 H), 8.08 (s, 1 H), 4.94-4.96 (m, 1 H), 4.40 (t, J = 5.2 Hz, 2 H), 3.81 (t, J = 5.2 Hz, 2 H), 3.31 (s, 3 H), 2.86-2.88 (m, 1 H), 1.57-2.18 (m, 10 H). |

| Compound No. | Compound Structure | MS + 1 | 1HNMR (Resolution) |
|---|---|---|---|
| WX-284 | 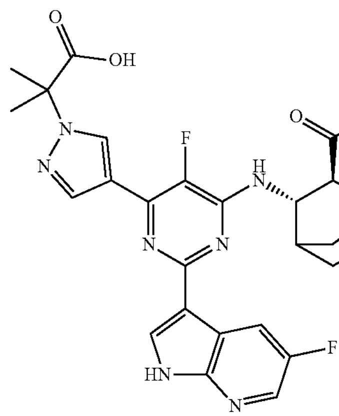 | 552.1 | $^1$H NMR (400 MHz, METHANOL-d4) δ 8.65 (dd, J = 2.76, 9.54 Hz, 1H), 8.47 (s, 1H), 8.38 (s, 1H), 8.18 (s, 2H), 4.92 (br s, 1H), 2.80 (br d, J = 7.03 Hz, 1H), 2.12 (br s, 1H), 2.05 (br s, 1H), 1.80-2.01 (m, 9H), 1.63-1.79 (m, 3H), 1.56 (br s, 2H). |
| WX-285 | 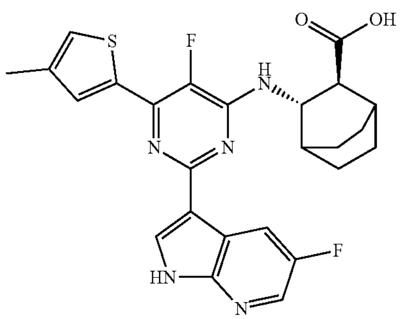 [SMILES: Cc1csc(-c2nc(-c3c[nH]c4ncc(F)cc34)nc(N[C@H]3C4CCC(CC4)[C@@H]3C(=O)O)c2F)c1] | 496.2 | $^1$H NMR (400 MHz, METHANOL-d4) δ 8.85 (dd, J = 2.64, 9.66 Hz, 1H), 8.24 (s, 1H), 8.19 (s, 1H), 7.71 (s, 1H), 7.13 (s, 1H), 4.73 (br d, J = 6.78 Hz, 1H), 2.74 (br d, J = 6.02 Hz, 1H), 2.35 (s, 3H), 2.09 (br s, 1H), 2.03 (br s, 1H), 1.63-1.95 (m, 7H), 1.48-1.60 (m, 2H), 1.28-1.41 (m, 1H). |
| WX-286 | 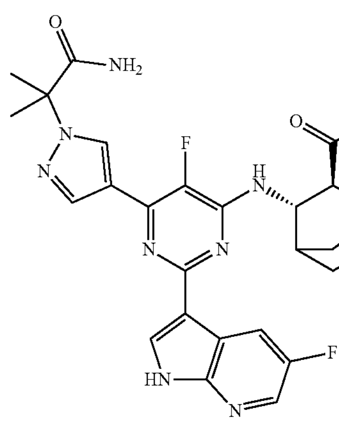 | 551.3 | $^1$H NMR (400 MHz, METHANOL-d4) δ 8.63 (br d, J = 6.53 Hz, 1H), 8.56 (s, 1H), 8.50 (s, 1H), 8.24 (s, 2H), 5.00 (br s, 1H), 2.86 (br s, 1H), 2.15 (br s, 1H), 2.05 (br s, 1H), 1.82-2.01 (m, 9H), 1.74 (br s, 3H), 1.57 (br s, 2H). |
| WX-288 | 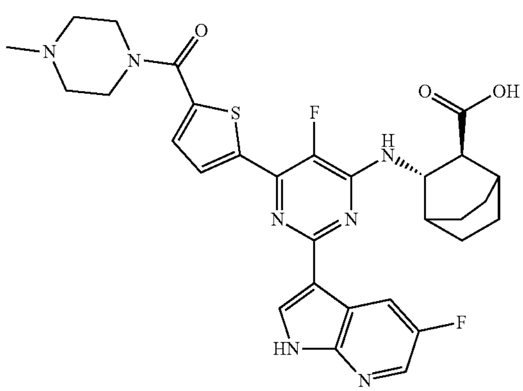 [SMILES: CN1CCN(C(=O)c2ccc(-c3nc(-c4c[nH]c5ncc(F)cc45)nc(N[C@H]4C5CCC(CC5)[C@@H]4C(=O)O)c3F)s2)CC1] | 608.4 | $^1$H NMR (400 MHz, METHANOL-d4) δ 8.81 (dd, J = 2.76, 9.79 Hz, 1H), 8.23 (s, 1H), 8.20 (s, 1H), 7.88 (d, J = 4.02 Hz, 1H), 7.50 (d, J = 3.51 Hz, 1H), 4.69 (br d, J = 7.03 Hz, 1H), 3.48 (br s, 5H), 2.99 (s, 3H), 2.73 (br d, J = 7.53 Hz, 1H), 2.06 (br s, 1H), 1.99 (br s, 1H), 1.83 (br d, J = 16.56 Hz, 3H), 1.70 (br s, 3H), 1.54 (br d, J = 10.54 Hz, 2H). |

| Compound No. | Compound Structure | MS + 1 | 1HNMR (Resolution) |
|---|---|---|---|
| WX-289 | 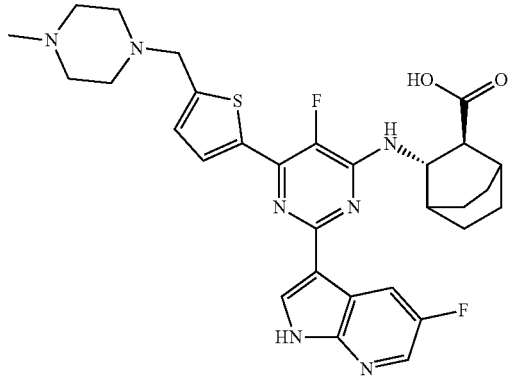 [SMILES: CN1CCN(Cc2ccc(-c3nc(-c4c[nH]c5ncc(F)cc45)nc(N[C@H]4C5CCC(CC5)[C@@H]4C(=O)O)c3F)s2)CC1] | 594.1 | ¹H NMR (400 MHz, METHANOL-d4) δ 8.75 (dd, J = 2.89, 9.66 Hz, 1H), 8.28 (s, 1H), 8.20 (s, 1H), 7.74 (dd, J = 1.63, 3.64 Hz, 1H), 7.16 (d, J = 3.76 Hz, 1H), 4.81 (br d, J = 6.27 Hz, 1H), 4.00 (s, 2H), 3.33-3.49 (m, 9H), 2.93 (s, 3H), 2.76 (br d, J = 6.27 Hz, 1H), 2.09 (br s, 1H), 2.04 (br s, 1H), 1.66-1.97 (m, 7H), 1.51-1.61 (m, 2H) |
| WX-290 | 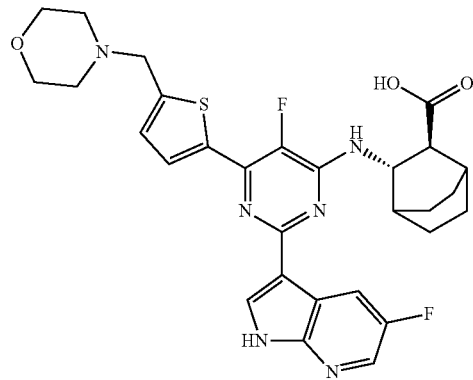 [SMILES: O=C(O)[C@H]1C2CCC(CC2)[C@@H]1Nc1nc(-c2c[nH]c3ncc(F)cc23)nc(-c2ccc(CN3CCOCC3)s2)c1F] | 581.2 | ¹H NMR (400 MHz, METHANOL-d4) δ 8.75 (s, 1H), 8.72 (s, 1H), 8.28 (s, 1H), 7.85 (d, J = 2.51 Hz, 1H), 7.46 (d, J = 3.76 Hz, 1H), 4.81 (br d, J = 6.53 Hz, 1H), 4.73 (s, 2H), 3.37-4.18 (m, 8H), 2.76 (br d, J = 6.53 Hz, 1H), 2.10 (br s, 1H), 2.03 (s, 1H), 1.65-1.97 (m, 7H), 1.51-1.61 (m, 2H) |
| WX-293 | 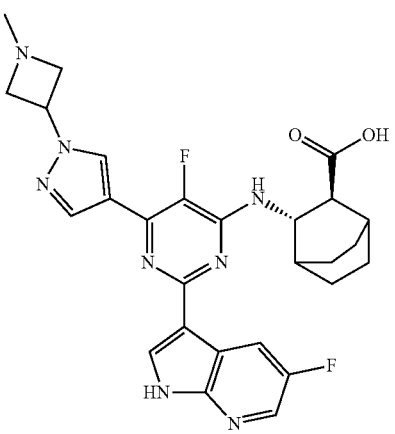 [SMILES: CN1CC(n2cc(-c3nc(-c4c[nH]c5ncc(F)cc45)nc(N[C@H]4C5CCC(CC5)[C@@H]4C(=O)O)c3F)cn2)C1] | 535.2 | ¹H NMR (400 MHz, METHANOL-d4) δ 8.66 (dd, J = 2.76, 9.54 Hz, 1H), 8.43 (s, 1H), 8.38 (s, 2H), 8.21 (br s, 1H), 5.48-5.59 (m, 1H), 4.74 (br s, 1H), 4.55 (br s, 2H), 3.03-3.25 (m, 3H), 2.79 (br d, J = 6.27 Hz, 1H), 2.12 (br s, 1H), 2.04 (br s, 1H), 1.80-1.99 (m, 4H), 1.63-1.79 (m, 3H), 1.55 (br d, J = 10.04 Hz, 2H) |
| WX-294 | 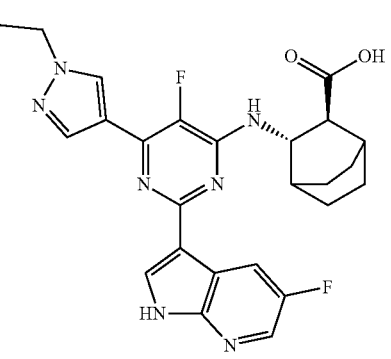 [SMILES: CCn1cc(-c2nc(-c3c[nH]c4ncc(F)cc34)nc(N[C@H]3C4CCC(CC4)[C@@H]3C(=O)O)c2F)cn1] | 494.2 | ¹H NMR (400 MHz, METHANOL-d4) δ 8.77 (s, 1H), 8.56 (s, 1H), 8.54 (d, J = 2.51 Hz, 1H), 8.52-8.59 (m, 1H), 8.32 (s, 1H), 8.24 (s, 1H), 7.68 (d, J = 8.28 Hz, 1H), 7.21 (d, J = 8.03 Hz, 1H), 5.16 (br d, J = 6.53 Hz, 1H), 4.36 (q, J = 7.28 Hz, 2H), 2.97 (br d, J = 6.78 Hz, 1H), 2.22 (br s, 1H), 2.05 (br s, 1H), 1.60-1.99 (m, 8H), 1.56 (t, J = 7.28 Hz, 3H), 1.22 (s, 1H). |

-continued

| Compound No. | Compound Structure | MS + 1 | 1HNMR (Resolution) |
|---|---|---|---|
| WX-295 | 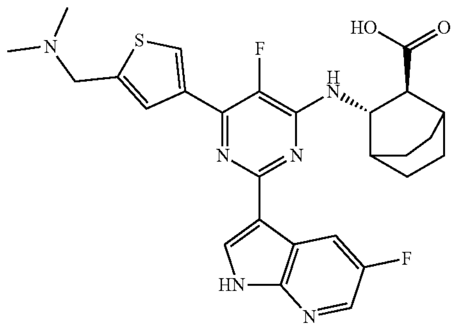 [SMILES: CN(C)Cc1cc(-c2nc(-c3c[nH]c4ncc(F)cc34)nc(N[C@H]3C4CCC(CC4)[C@@H]3C(=O)O)c2F)cs1] | 539.1 | ¹H NMR (400 MHz, DMSO-d6) δ 12.36 (br s, 1H), 9.95 (br s, 1H), 8.41-8.65 (m, 2H), 8.31 (d, J = 2.26 Hz, 2H), 8.04 (s, 1H), 7.67 (br d, J = 6.53 Hz, 1H), 4.58-4.78 (m, 3H), 2.76-2.98 (m, 7H), 2.01 (br d, J = 15.06 Hz, 2H), 1.27-1.74 (m, 6H) |
| WX-296 | 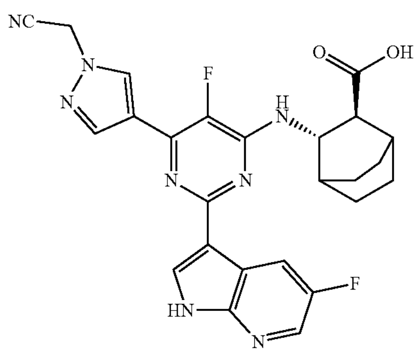 [SMILES: N#CCn1cc(-c2nc(-c3c[nH]c4ncc(F)cc34)nc(N[C@H]3C4CCC(CC4)[C@@H]3C(=O)O)c2F)cn1] | 505.2 | ¹H NMR (400 MHz, METHANOL-d4) δ 8.47 (s, 1H), 8.45-8.49 (m, 1H), 8.32 (s, 1H), 8.30-8.35 (m, 1H), 8.26-8.29 (m, 1H), 8.26 (s, 1H), 8.17 (br s, 1H), 8.15-8.21 (m, 1H), 7.37 (s, 1H), 2.78 (s, 1H), 2.38 (br s, 1H), 2.36-2.39 (m, 1H), 2.17-2.23 (m, 1H), 2.19 (br t, J = 8.03 Hz, 2H), 1.97-2.13 (m, 8H), 1.94 (s, 4H) |
| WX-298 | 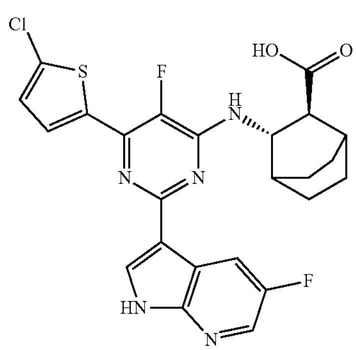 [SMILES: O=C(O)[C@H]1C2CCC(CC2)[C@@H]1Nc1nc(-c2c[nH]c3ncc(F)cc23)nc(-c2ccc(Cl)s2)c1F] | 516.1 | ¹H NMR (400 MHz, DMSO-d6) δ 12.36 (br s, 2H), 8.33 (s, 1H), 8.08-8.24 (m, 3H), 7.77 (d, J = 2.76 Hz, 1H), 7.60 (d, J = 3.76 Hz, 1H), 4.45 (br t, J = 6.53 Hz, 1H), 2.84 (br d, J = 6.02 Hz, 1H), 1.98 (br s, 1H), 1.68-1.81 (m, 3H), 1.28-1.62 (m, 6H). |
| WX-352 | 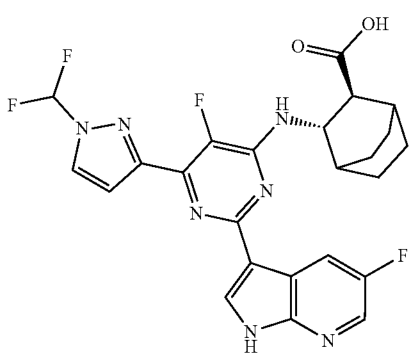 [SMILES: O=C(O)[C@H]1C2CCC(CC2)[C@@H]1Nc1nc(-c2c[nH]c3ncc(F)cc23)nc(-c2ccn(C(F)F)n2)c1F] | 516.1 | ¹H NMR (400 MHz, METHANOL-d4) δ 8.93 (s, 1H), 8.69 (s, 1H), 8.56-8.60 (m, 1H), 8.39 (s, 1H), 8.31 (br s, 1H), 2.94 (br d, J = 6.53 Hz, 1H), 2.20 (br s, 1H), 2.05 (br s, 1H), 1.84-2.01 (m, 3H), 1.67-1.82 (m, 3H), 1.53-1.66 (m, 2H), 1.27-1.40 (m, 2H) |

Example 2

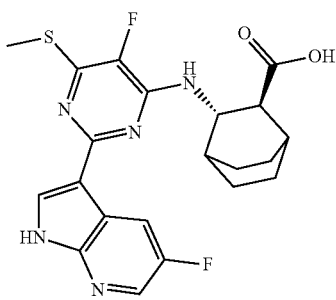

Synthetic Route:

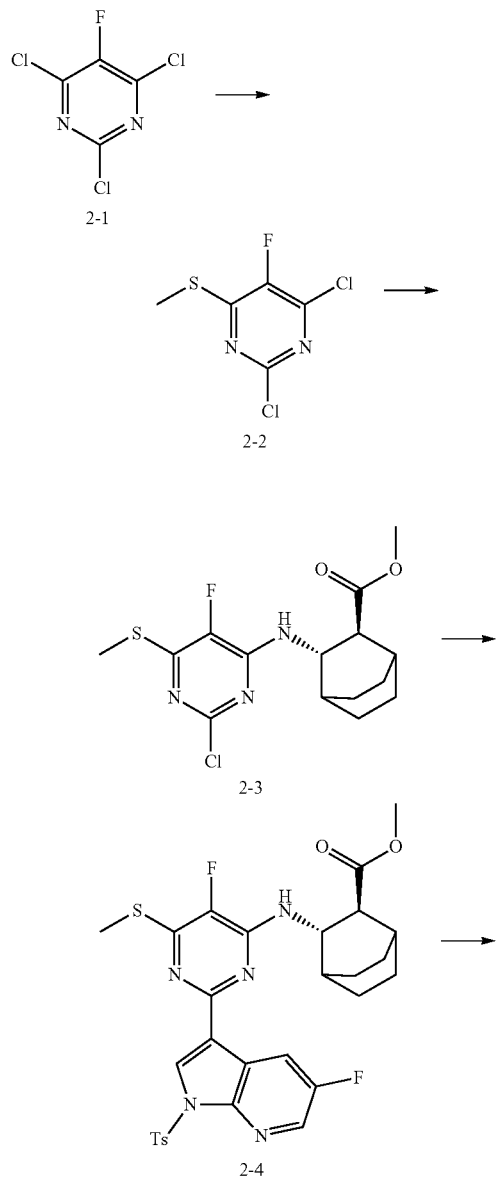

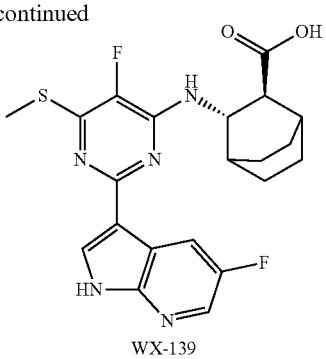

WX-139

Step 1: Synthesis of Compound 2-2

At room temperature, the compound 2-1 (500.00 mg, 2.48 mmol) was dissolved in tetrahydrofuran (8.00 mL), into which was added a solution of sodium thiomethoxide (173.82 mg, 2.48 mmol, 158.02 uL) in methanol (2 mL) dropwise at −40° C. The reaction liquid was stirred at −40° C. for 1 hour, and then heated to room temperature and stirred overnight. The reaction liquid was diluted with ethyl acetate (60 mL), washed with water (15 mL), saturated brine (15 mL), respectively. The organic phases were dried over anhydrous sodium sulfate, filtered, and concentrated at reduced pressure to give the crude compound 2-2 (490.00 mg, 2.30 mmol). 1H NMR (400 MHz, CHLOROFORM-d) δ 2.65 (s, 3H).

Step 2: Synthesis of Compound 2-3

In an ice bath, the compound BB-1 (400.00 mg, 2.18 mmol) and the compound 2-2 (464.47 mg, 2.18 mmol, 1.00 eq) were dissolved in tetrahydrofuran (6.00 mL), into which was added diisopropyl ethylamine (1.41 g, 10.90 mmol, 1.91 mL, 5.00 eq), the reaction liquid was stirred at 55° C. for 72 hours. The reaction liquid was diluted with ethyl acetate (30 mL), washed with water (10 mL) and saturated brine (10 mL), respectively. The organic phases were dried over anhydrous sodium sulfate, filtered, and concentrated at reduced pressure. The resultants were purified by flash silica gel column chromatography (petroleum ether:ethyl acetate=100:1 to 5:1) to give the compound 2-3 (500.00 mg, 1.35 mmol, yield 61.93%). MS (ESI) m/z: 359.9 (M+H$^+$).

Step 3: Synthesis of Compound 2-4

The compound 2-3 (40.00 mg, 111.16 umol, 1.00 eq), BB-3 (46.27 mg, 111.16 umol, 1.00 eq) were dissolved in 2-methyl tetrahydrofuran (3.00 mL) and water (800.00 uL), into which were added tri(dibenzylidene acetone) dipalladium (10.18 mg, 11.12 umol, 0.10 eq), 2-dicyclohexyl phosphine-2',4',6'-triisopropyl biphenyl (10.60 mg, 22.23 umol, 0.20 eq) and potassium phosphate (47.19 mg, 222.32 umol, 2.00 eq), the mixture was stirred at 80° C. under nitrogen for 10 hours. The reaction liquid was diluted with ethyl acetate (40 mL), washed with water (15 mL) and saturated brine (15 mL), respectively. The organic phases were dried over anhydrous sodium sulfate, filtered, and concentrated at reduced pressure. The resultants were purified over a thin layer chromatographic plate (petroleum ether:ethyl acetate=1:1) to give the compound 2-4 (40.00 mg, 39.76 umol, yield 35.77%).

Step 4: Synthesis of Compound WX-139

To a solution of the compound 2-4 (40.00 mg, 65.18 umol) in methanol (1 mL), tetrahydrofuran (1.00 mL) and water (0.5 mL) was added lithium hydroxide monohydrate (13.67 mg, 325.90 umol). The mixture was stirred at 50° C. for 12 hours. Tetrahydrofuran was removed by concentration, into which was added HCl (1M) to adjust to pH=5, extracted with ethyl acetate (20 mL). The organic phases were concentrated at reduced pressure, the resultants were prepared and purified to give the compound WX-139 (16.00 mg, 28.17 umol, yield 43.22%). $^1$H NMR (400 MHz, METHANOL-$d_4$) δ 8.59-8.68 (m, 1H), 8.25 (s, 1H), 8.13-8.20 (m, 1H), 4.78-4.83 (in 1H), 2.71-2.75 (m, 1H), 2.69 (s, 3H), 2.06-2.11 (m, 1H), 1.98-2.04 (m, 1H), 1.79-1.97 (in 3H), 1.59-1.78 (m, 3H), 1.45-1.59 (in, 2H). MS (ESI) m/z: 446.1 [M+1].

Following the synthetic process in steps 1~4 of Example 2, each example in the table below was synthesized.

| Compound No. | Compound Structure | MS + 1 | 1HNMR (Resolution) |
|---|---|---|---|
| WX-156 | [structure] | 460.1 | $^1$H NMR (400 MHz, METHANOL-$d_4$) δ 8.66-8.57 (m, 1H), 8.26-8.20 (m, 1H), 8.19-8.13 (m, 1H), 4.83-4.77 (m, 1H), 3.39-3.34 (m, 2H), 2.76-2.69 (m, 1H), 2.11-2.06 (m, 1H), 2.04-1.99 (m, 1H), 1.97-1.81 (m, 3H), 1.78-1.63 (m, 3H), 1.59-1.51 (m, 2H), 1.50-1.44 (m, 3H) |
| WX-160 | [structure] | 463.1 | $^1$H NMR (400 MHz, METHANOL-$d_4$) δ 8.15 (s, 1H), 8.14-8.08 (m, 1H), 6.86-6.76 (m, 1H), 4.84-4.78 (m, 1H), 2.76-2.71 (m, 1H), 2.69 (s, 3H), 2.12-2.07 (m, 1H), 2.05-2.01 (m, 1H), 2.00-1.92 (m, 1H), 1.90-1.81 (m, 2H), 1.76-1.63 (m, 3H), 1.57-1.46 (m, 2H) |
| WX-186 | [structure] | 466.2 | $^1$H NMR (400 MHz, DMSO-$d_6$) δ 12.45 (s, 1 H), 9.33 (s, 1 H), 8.49-8.46 (m, 2 H), 8.31-8.22 (m, 1 H), 8.12-8.10 (m, 1 H), 7.65 (s, 1 H), 7.48-7.10 (M, 1 H), 4.77 (s, 1 H), 3.50-3.49 (m, 1 H), 2.94-1.48 (m, 10 H). |
| WX-234 | [structure] | 514.1 | $^1$H NMR (400 MHz, METHANOL-$d_4$) δ 8.55 (dd, J = 2.76, 9.54 Hz, 1H), 8.23 (s, 1H), 8.16 (br s, 1H), 4.90 (br s, 1H), 4.18-4.33 (m, 2H), 2.73 (br d, J = 6.53 Hz, 1H), 2.09 (br s, 1H), 2.02 (br d, J = 10.79 Hz, 1H), 1.92 (br d, J = 13.80 Hz, 1H), 1.77-1.88 (m, 2H), 1.60-1.77 (m, 3H), 1.46-1.58 (m, 2H) |

| Compound No. | Compound Structure | MS + 1 | 1HNMR (Resolution) |
|---|---|---|---|
| WX-241 | 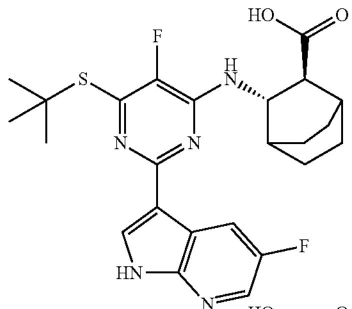 [SMILES: CC(C)(C)Sc1nc(-c2c[nH]c3ncc(F)cc23)nc(N[C@H]2C3CCC(CC3)[C@@H]2C(=O)O)c1F] | 488.1 | $^1$H NMR (400 MHz, DMSO-d$_6$) δ 12.29 (br s, 1H), 8.48 (dd, J = 2.89, 9.91 Hz, 1H), 8.28 (d, J = 1.25 Hz, 1H), 8.08 (d, J = 2.76 Hz, 1H), 7.43 (br d, J = 7.03 Hz, 1H), 4.66 (br t, J = 6.78 Hz, 1H), 4.05 (s, 3H), 2.82 (br d, J = 7.03 Hz, 1H), 2.23-2.23 (m, 1H), 1.99 (br s, 1H), 1.92 (br s, 1H), 1.73 (br d, J = 6.78 Hz, 3H), 1.64 (s, 9H), 1.48 (br d, J = 9.29 Hz, 3H). |
| WX-261 | 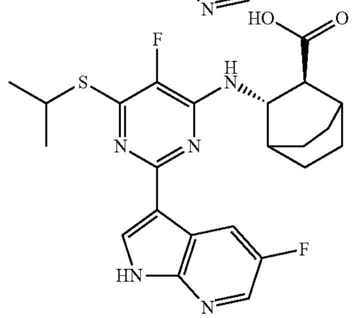 | 474.1 | $^1$H NMR (400 MHz, DMSO-d6) δ 12.30 (br s, 2H), 8.43 (dd, J = 2.76, 9.79 Hz, 1H), 8.28 (s, 1H), 8.20 (d, J = 2.76 Hz, 1H), 7.39 (br d, J = 6.53 Hz, 1H), 4.63 (br t, J = 6.78 Hz, 1H), 4.16 (td, J = 6.78, 13.55 Hz, 1H), 2.80 (br d, J = 6.78 Hz, 1H), 1.98 (br s, 1H), 1.91 (br s, 1H), 1.46-1.83 (m, 7H), 1.42 (dd, J = 1.51, 6.78 Hz, 7H), 1.35 (br d, J = 10.29 Hz, 1H) |
Example 3
WX-264
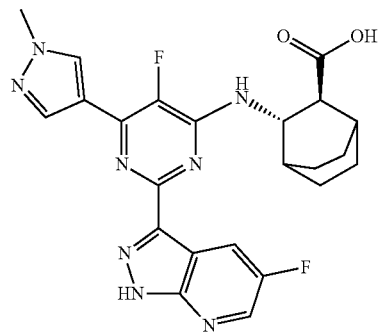
Synthetic Route:
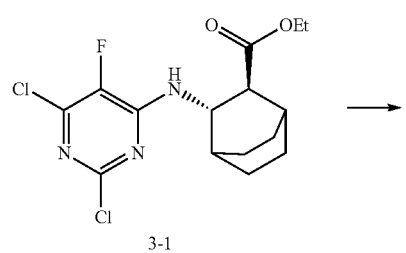
3-1
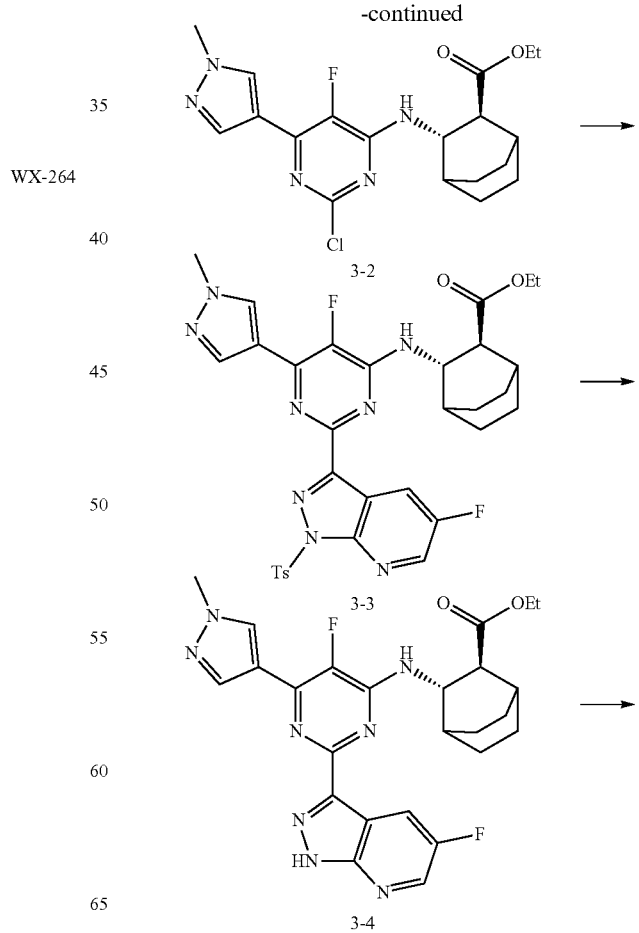

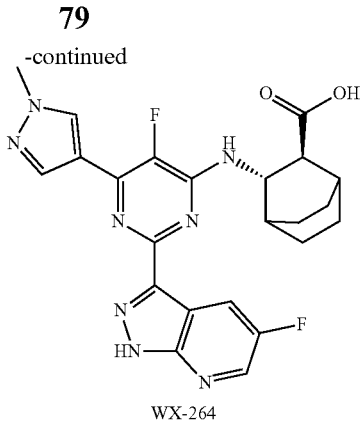

WX-264

Step 1: Synthesis of Compound 3-2

At room temperature, the compound 3-1 (300.00 mg, 828.20 umol) and 1-methyl-4-pinacol borate parazole (206.78 mg, 993.84 umol) were dissolved in tetrahydrofuran (4.00 mL) and water (1.00 mL), into which were added potassium phosphate (351.61 mg, 1.66 mmol) and palladium 1'-bis(di-tert-butylphosphine)ferrocene dichloride (26.99 mg, 41.41 umol), respectively. The reaction liquid was reacted at 40° C. overnight. The reaction liquid was cooled to room temperature, into which was added water (30 mL), then filtered. The filtrate was with extracted ethyl acetate (10 mL×3). The organic phases were combined, dried over anhydrous sodium sulfate, filtered, and concentrated at reduced pressure. The resulting crude product was purified over a flash silica gel column (10-30% ethyl acetate/petroleum ether) to give the compound 3-2 (150 mg, yield 44.4%). $^1$H NMR (400 MHz, CHLOROFORM-d) δ 8.05 (d, J=2.01 Hz, 1H), 8.02 (s, 1H), 5.23 (br d, J=5.02 Hz, 1H), 4.51 (br t, J=5.52 Hz, 1H), 4.23 (q, J=7.03 Hz, 2H), 3.97 (s, 3H), 2.39 (br d, J=6.02 Hz, 1H), 2.02 (br d, J=2.51 Hz, 1H), 1.90 (br d, J=2.51 Hz, 1H), 1.77-1.87 (m, 1H), 1.52-1.76 (m, 11H), 1.44 (br t, J=11.29 Hz, 1H), 1.27 (t, J=7.28 Hz, 4H). MS (ESI) m/z: 408.1 (M+H$^+$).

Step 2: Synthesis of Compound 3-3

At room temperature, the compound 3-2 (150.00 mg, 367.76 umol) and BB-4 (223.03 mg, 441.31 umol) were dissolved in 2-methyl tetrahydrofuran (4.00 mL) and water (1.00 mL), into which were added potassium phosphate (156.13 mg, 735.52 umol), tri(dibenzylidene acetone) dipalladium (16.84 mg, 18.39 umol) and 2-dicyclohexylphosphine-2',4',6'-triisopropyl biphenyl (35.06 mg, 73.55 umol), respectively. The reaction liquid was reacted at 80° C. overnight. The reaction liquid was cooled to room temperature, into which was added water (30 mL), then filtered. The filtrate was extracted with ethyl acetate (10 mL×3). The organic phases were combined, dried over anhydrous sodium sulfate, filtered, and concentrated at reduced pressure. The resulting crude product was purified over a flash silica gel column (15~30% ethyl acetate/petroleum ether) to give the compound 3-3 (160.00 mg, 213.09 umol, yield 57.94%). MS (ESI) m/z: 773.4 (M+H$^+$).

Step 3: Synthesis of Compound 3-4

At room temperature, the compound 3-3 (160.00 mg, 213.09 umol) was dissolved in dichloromethane (3.00 mL), into which was added trifluoroacetic acid (485.93 mg, 4.26 mmol). The reaction liquid was reacted at 25° C. overnight. The reaction liquid was concentrated at reduced pressure, into the residues of which was added a saturated aqueous solution of sodium bicarbonate (20 mL), and extracted with ethyl acetate (8 mL×3). The organic phases were combined, dried over anhydrous sodium sulfate, filtered, and concentrated at reduced pressure. The resulting crude product was purified over a flash silica gel column (20-90% ethyl acetate/petroleum ether) to give the compound 3-4 (60.00 mg, yield 55.4%). MS (ESI) m/z: 509.3 (M+H$^+$).

Step 4: Synthesis of Compound WX-264

At room temperature, the compound 3-4 (60.00 mg, 117.99 umol) was dissolved in tetrahydrofuran (2.00 mL) and water (500.00 uL), into which was added sodium hydroxide (23.60 mg, 589.95 umol). The reaction liquid was reacted at 60° C. overnight. The reaction liquid was concentrated at reduced pressure, into which was then added 1 M HCl to adjust to pH=6, to give the compound WX-264 (50.00 mg, yield 88.20%). $^1$H NMR (400 MHz, CHLOROFORM-d) δ 8.65 (dd, J=2.89, 8.41 Hz, 1H), 8.54-8.58 (m, 1H), 8.42 (s, 1H), 8.23 (s, 1H), 5.01 (br d, J=6.78 Hz, 1H), 4.00 (s, 3H), 2.85 (d, J=6.78 Hz, 1H), 2.15 (br s, 1H), 2.04 (br s, 1H), 1.82-2.00 (m, 3H), 1.63-1.80 (m, 3H), 1.55 (br d, J=12.80 Hz, 2H). MS (ESI) m/z: 481.2 (M+H$^+$).

Following the synthetic process in steps 1-3 of Example 3, each example in the table below was synthesized.

| Compound No. | Compound Structure | MS + 1 | 1HNMR (Resolution) |
| --- | --- | --- | --- |
| WX-265 | 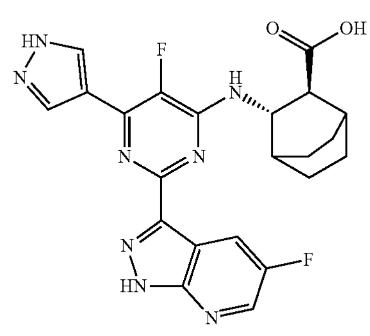 [SMILES: O=C(O)[C@H]1C2CCC(CC2)[C@@H]1Nc1nc(-c2n[nH]c3ncc(F)cc23)nc(-c2cn[nH]c2)c1F] | 467.2 | $^1$H NMR (400 MHz, METHANOL-d$_4$) δ 8.69 (dd, J = 2.76, 8.28 Hz, 1H), 8.54-8.58 (m, 1H), 8.43 (d, J = 1.51 Hz, 2H), 5.01 (br d, J = 7.03 Hz, 1H), 2.85 (br d, J = 7.03 Hz, 1H), 2.15 (br s, 1H), 2.05 (br s, 1H), 1.82-2.00 (m, 3H), 1.63-1.80 (m, 3H), 1.55 (br d, J = 13.05 Hz, 2H). |

-continued
| Compound No. | Compound Structure | MS + 1 | 1HNMR (Resolution) |
|---|---|---|---|
| WX-269 | 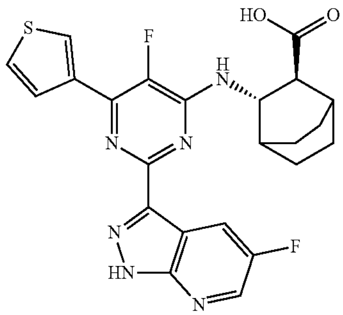 [SMILES: O=C(O)[C@H]1C2CCC(CC2)[C@@H]1Nc1nc(-c2n[nH]c3ncc(F)cc23)nc(-c2ccsc2)c1F] | 483.2 | ¹HNMR (400 MHz, METHANOL-d₄) δ 8.66 (dd, J = 2.89, 8.41 Hz, 1H), 8.54-8.57 (m, 1H), 8.39 (d, J = 2.76 Hz, 1H), 7.92 (d, J = 5.02 Hz, 1H), 7.58 (dd, J = 3.01, 5.27 Hz, 1H), 5.01 (br d, J = 7.03 Hz, 1H), 2.86 (br d, J = 6.78 Hz, 1H), 2.16 (br s, 1H), 2.06 (br s, 1H), 1.81-2.02 (m, 4H), 1.50-1.80 (m, 6H) |
| WX-271 | 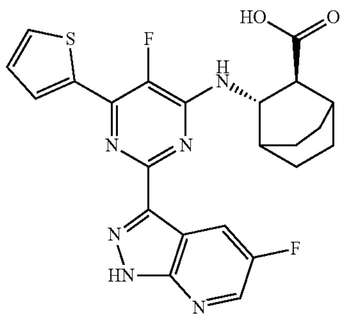 [SMILES: O=C(O)[C@H]1C2CCC(CC2)[C@@H]1Nc1nc(-c2n[nH]c3ncc(F)cc23)nc(-c2cccs2)c1F] | 483.1 | ¹H NMR (400 MHz, DMSO-d₆) δ 8.52-8.69 (m, 2H), 7.74-7.92 (m, 3H), 7.30 (t, J = 4.27 Hz, 1H), 4.78 (br s, 1H), 2.73 (br s, 1H), 1.92-2.06 (m, 2H), 1.21-1.84 (m, 10H). |
| WX-280 | 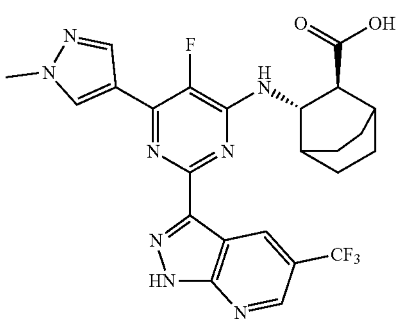 [SMILES: Cn1cc(-c2nc(-c3n[nH]c4ncc(C(F)(F)F)cc34)nc(N[C@H]3C4CCC(CC4)[C@@H]3C(=O)O)c2F)cn1] | 531.2 | ¹H NMR (400 MHz, METHANOL-d₄) δ 9.32 (s, 1H), 8.84 (br d, J = 1.60 Hz, 1H), 8.37 (s, 1H), 8.22 (s, 1H), 5.03 (br d, J = 7.22 Hz, 1H), 3.98 (s, 3H), 2.78 (br d, J = 6.82 Hz, 1H), 2.13 (br s, 1H), 1.74-1.94 (m, 4H), 1.62-1.69 (m, 3H), 1.50-1.56 (m, 2H). |
Example 4
WX-216
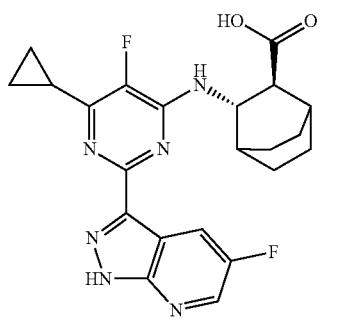
Synthetic Route:
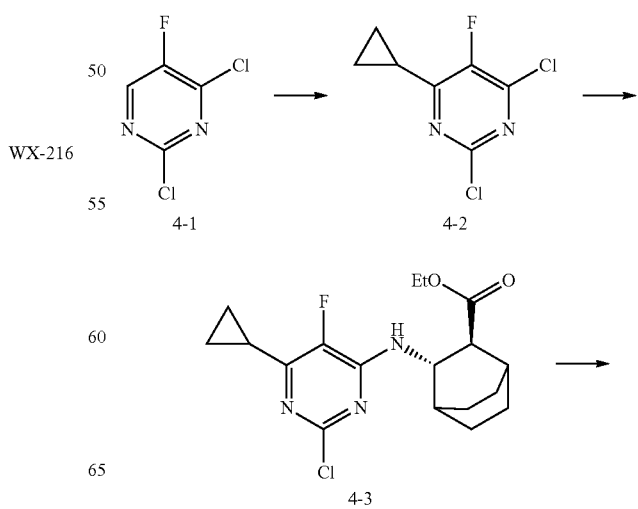

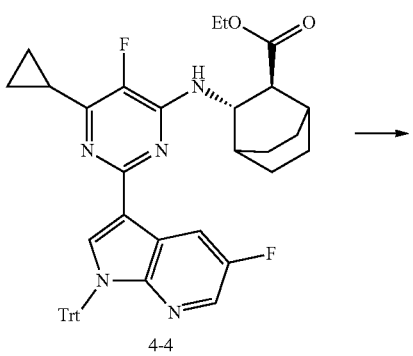

4-4

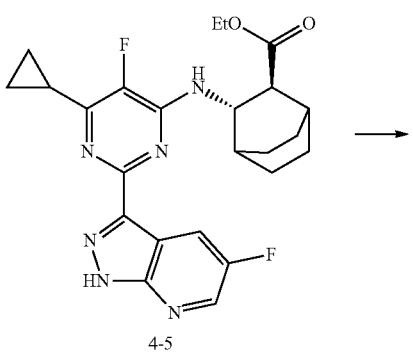

4-5

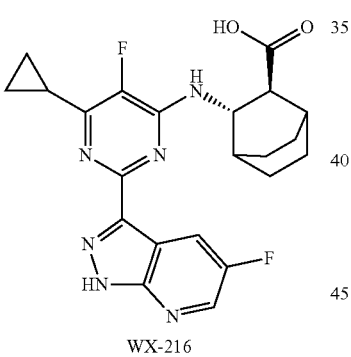

WX-216

Step 1: Synthesis of Compound 4-2

At 0° C., the compound 4-1 (25.00 g, 149.73 mmol) was dissolved in ethylene glycol dimethyl ether (80 mL), into which was added cyclopropyl magnesium bromide (0.5 M, 500.10 mL) dropwise. The reaction liquid was stirred at room temperature overnight. The reaction was then cooled to 0° C., into which was added a solution of triethylamine (15.15 g, 149.73 mmol, 20.75 mL) in tetrahydrofuran (30 mL) and a solution of iodine (38.00 g, 149.73 mmol) in tetrahydrofuran (30 mL), respectively. The reaction liquid was stirred at room temperature for 3 hours. To the reaction liquid was added ethyl acetate (1 L), washed with water (300 mL×3) and saturated brine (300 mL) respectively, dried over anhydrous sodium sulfate, filtered, and concentrated at reduced pressure. The resulting crude product was purified over a silica gel column (petroleum ether) to give the compound 4-2 (8 g, yield 25.8%).

Step 2: Synthesis of Compound 4-3

The compound BB-2 (450 mg, 2.28 mmol) and the compound 4-2 (450 mg, 2.17 mmol) were dissolved in tetrahydrofuran (5.00 mL), into which was added diisopropyl ethylamine (841.35 mg, 6.51 mmol). The reaction liquid was stirred at 55° C. for 3 hours. The reaction liquid was concentrated at reduced pressure, the resulting crude product was purified by flash silica gel column chromatography (petroleum ether:ethyl acetate=10:1 to 5:1) to give the compound 4-3 (460.00 mg, yield 57.6%).

Step 3: Synthesis of Compound 4-4

At room temperature, the compound 4-3 (460.00 mg, 1.25 mmol) and BB-4 (1.05 g, 1.25 mmol) were dissolved in 2-methyl tetrahydrofuran (8.00 mL) and water (2.00 mL), into which were added potassium phosphate (796.34 mg, 3.75 mmol), tri(dibenzylidene acetone) dipalladium (114.51 mg, 125.05 umol) and 2-dicyclohexylphosphine-2',4',6'-triisopropyl biphenyl (119 mg, 250 umol), respectively. The reaction liquid was reacted at 80° C. overnight. The reaction liquid was cooled to room temperature, into which was added water (30 mL), then filtered. The filtrate was extracted with ethyl acetate (10 mL×3). The organic phases were combined, dried over anhydrous sodium sulfate, filtered, and concentrated at reduced pressure. The resulting crude product was purified over a flash silica gel column (petroleum ether:ethyl acetate=20:1 to 3:1) to give the compound 4-4 (600 mg, yield 61%). MS (ESI) m/z: 773.4 (M+H$^+$).

Step 4: Synthesis of Compound 4-5

At room temperature, the compound 4-4 (600.00 mg, 844.11 umol) was dissolved in dichloromethane (6.00 mL), into which were added trifluoroacetic acid (962.45 mg, 8.44 mmol) and triethyl hydrosilane (981.53 mg, 8.44 mmol). The reaction liquid was reacted at room temperature for 4 hours. The reaction liquid was concentrated at reduced pressure, the resulting crude product was purified over a flash silica gel column (petroleum ether:ethyl acetate=10:1 to 2:1) to give the compound 4-5 (350.00 mg, yield 87.6%). MS (ESI) m/z: 469.2 (M+H$^+$).

Step 5: Synthesis of Compound WX-216

At room temperature, the compound 4-5 (160.00 mg, 341.52 umol) was dissolved in dioxane (3.00 mL) and water (500.00 uL), into which was added sodium hydroxide (136.61 mg, 3.42 mmol). The reaction liquid was reacted at 80° C. for 1 hour. The reaction liquid was concentrated at reduced pressure, into which was then added 1 M HCl to adjust to pH=5. A solid was separated out, filtered, and the filter cake was washed with water (10 mL), and dried to give WX-216 (55.4 mg, yield 36.5%). $^1$H NMR (400 MHz, METHANOL-$d_4$) δ 8.49-8.58 (m, 2H), 4.92 (br s, 1H), 2.78 (br d, J=6.78 Hz, 1H), 2.22-2.31 (m, 1H), 2.11 (br s, 1H), 1.80-2.02 (m, 4H), 1.61-1.77 (m, 3H), 1.44-1.59 (m, 2H), 1.25-1.34 (m, 3H), 1.03-1.11 (m, 2H). MS m/z: 441.1 [M+1]+.

Following the synthetic process in steps 3-5 of Example 4, each example in the table below was synthesized using BB-6 to BB-10.

| Compound No. | Compound Structure | MS + 1 | 1HNMR (Resolution) |
|---|---|---|---|
| WX-351 | 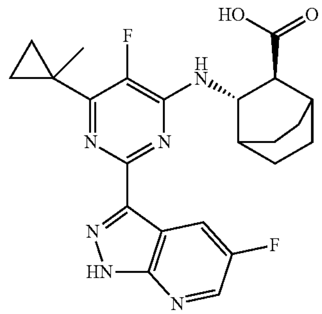 [SMILES: CC1(c2nc(-c3n[nH]c4ncc(F)cc34)nc(N[C@H]3C4CCC(CC4)[C@@H]3C(=O)O)c2F)CC1] | 455.1 | $^1$H NMR (400 MHz, DMSO-d$_6$) δ 8.63 (br s, 1H), 8.47 (br d, J = 8.78 Hz, 1H), 7.51 (br d, J = 6.78 Hz, 1H), 4.70 (br s, 1H), 1.85-2.06 (m, 2H), 1.74 (br s, 3H), 1.29-1.64 (m, 9H), 1.21 (br s, 2H), 0.79 (br s, 2H). |
| WX-353 | 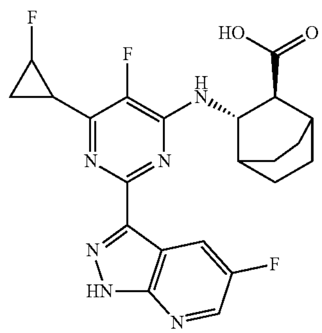 [SMILES: O=C(O)[C@H]1C2CCC(CC2)[C@@H]1Nc1nc(-c2n[nH]c3ncc(F)cc23)nc(C2CC2F)c1F] | 459.1 | $^1$H NMR (400 MHz, DMSO-d$_6$) δ 8.64 (dd, J = 1.38, 2.64 Hz, 1H), 8.41 (dd, J = 2.51, 8.53 Hz, 1H), 7.73 (br d, J = 6.53 Hz, 1H), 5.03-5.29 (m, 1H), 4.71 (br t, J = 6.90 Hz, 1H), 2.90 (br d, J = 7.28 Hz, 1H), 2.65-2.80 (m, 2H), 2.31-2.38 (m, 1H), 1.88-2.07 (m, 2H), 1.35-1.78 (m, 10H). |
| WX-354 | 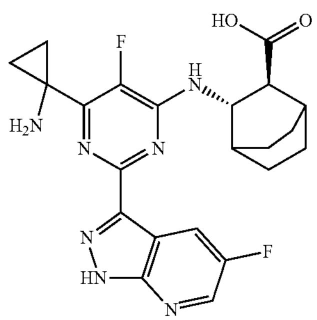 [SMILES: NC1(c2nc(-c3n[nH]c4ncc(F)cc34)nc(N[C@H]3C4CCC(CC4)[C@@H]3C(=O)O)c2F)CC1] | 456.2 | $^1$H NMR (400 MHz, METHANOL-d$_4$) δ 8.65-8.68 (m, 1 H), 8.58-8.59 (m, 1 H), 5.30-5.35 (m, 1 H), 2.80-2.81 (m, 1 H), 1.30-2.14 (m, 14 H). |
| WX-355 | 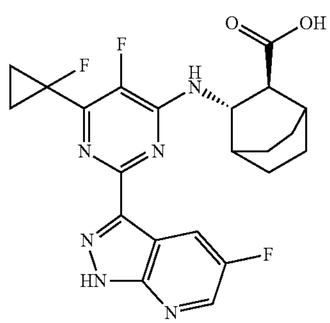 [SMILES: O=C(O)[C@H]1C2CCC(CC2)[C@@H]1Nc1nc(-c2n[nH]c3ncc(F)cc23)nc(C2(F)CC2)c1F] | 459.1 | $^1$H NMR (400 MHz, METHANOL-d$_4$) δ 8.60 (br d, J = 8.53 Hz, 1H), 8.53 (s, 1H), 4.95 (br d, J = 6.53 Hz, 1H), 2.82 (br d, J = 7.03 Hz, 1H), 2.13 (br s, 1H), 2.01 (s, 1H), 1.80-1.97 (m, 3H), 1.40-1.79 (m, 9H). |
| WX-358 | 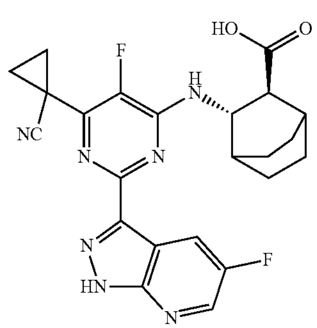 [SMILES: N#CC1(c2nc(-c3n[nH]c4ncc(F)cc34)nc(N[C@H]3C4CCC(CC4)[C@@H]3C(=O)O)c2F)CC1] | 466.2 | $^1$H NMR (400 MHz, METHANOL-d4) δ 8.54-8.64 (m, 2 H), 4.90-4.94 (m, 1 H), 2.81-2.83 (m, 1 H), 0.90-2.21 (m, 14 H). |

-continued
| Compound No. | Compound Structure | MS + 1 | 1HNMR (Resolution) |
|---|---|---|---|
| WX-274 | 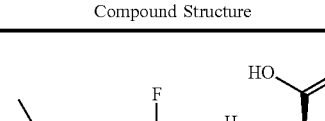 | 489.2 | ¹H NMR (400 MHz, DMSO-d$_6$) δ 14.19 (br s, 1H), 12.35 (br s, 1H), 8.64 (d, J = 1.25 Hz, 1H), 8.49 (dd, J = 2.64, 8.66 Hz, 1H), 7.64 (br d, J = 6.78 Hz, 1H), 4.71 (br t, J = 6.65 Hz, 1H), 3.56 (s, 1H), 2.86 (br d, J = 6.78 Hz, 1H), 1.87-2.05 (m, 2H), 1.75 (br d, J = 5.77 Hz, 3H), 1.67 (s, 9H), 1.33-1.57 (m, 5H). |
Example 5
WX-359
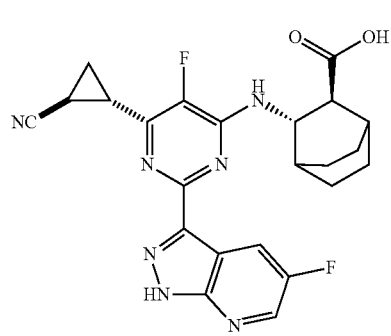
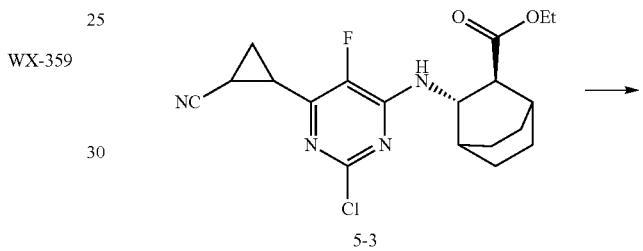
5-3
WX-360
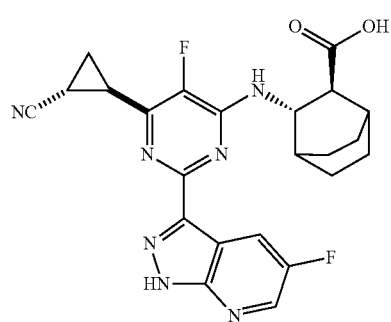
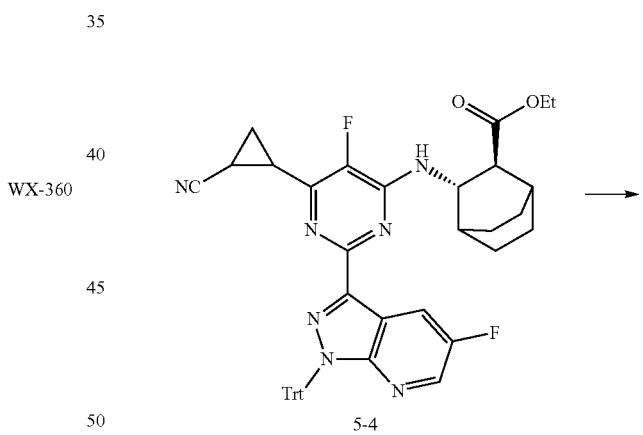
5-4
5-5
Synthetic Route:
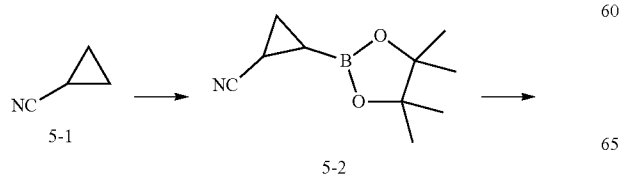
5-1  5-2

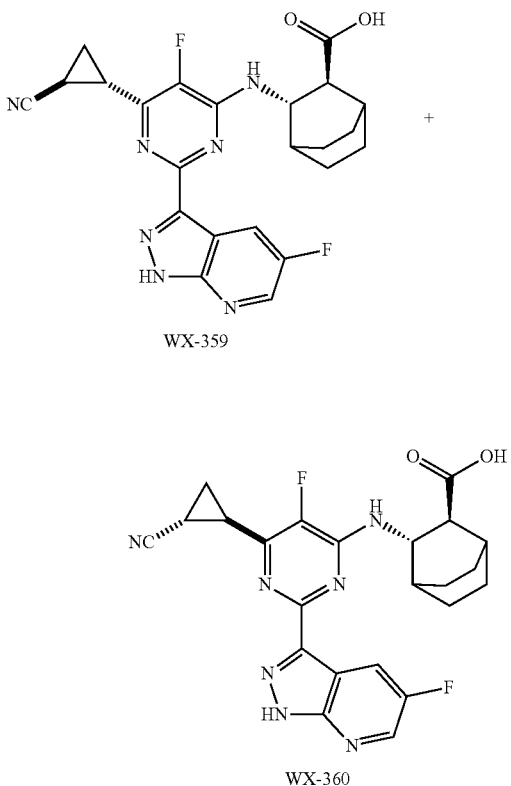

WX-359

WX-360

Step 1: Synthesis of Compound 5-2

Under the condition of room temperature, to a suspension of 5-1 (10.30 g, 153.58 mmol) and bis(pinacolato)diboron (30 g, 118.14 mmol) in tetrahydrofuran (150 mL) were added methoxy(cyclooctadiene)iridium dimer (3.13 g, 4.73 mmol) and 2,9-dimethyl-1,10-phenanthroline (984.14 mg, 4.73 mmol). The reaction liquid was protected under nitrogen, heated to 90° C. and reacted for 12 hours. The reaction liquid was filtered, the filtrate was concentrated at reduced pressure, the resulting crude product was purified over a silica gel chromatographic column (petroleum ether:ethyl acetate=10:1) to give the compound 5-2 (4.8 g, yield: 21%).

Step 2: Synthesis of Compound 5-3

Under the condition of room temperature, to a suspension of the compound 1-1 (1 g, 5.18 mmol) and compound 5-1 (2.06 g, 5.7 mmol) in tetrahydrofuran (20.00 mL) and water (1 mL) were added palladium 1,1'-bis(di-tert-butyl phosphino) ferrocene dichloride (337.61 mg, 518.00 mol) and anhydrous potassium phosphate (3.3 g, 15.54 mmol). The reaction liquid was heated to 50° C. under nitrogen and stirred for 12 hours. The reaction liquid was filtered, the filtrate was concentrated at reduced pressure, the resulting crude product was purified over a thin layer chromatographic plate (petroleum ether:ethyl acetate=5:1), to give the compound 5-3 (380.00 mg, yield 17.18%).

Step 3: Synthesis of Compound 5-4

Under the condition of room temperature, to a suspension of 5-3 (380.00 mg, 967.27 umol) and BB-4 (977.70 mg, 1.16 mmol) in 2-methyl tetrahydrofuran (5 mL) and water (0.5 mL) were added anhydrous potassium phosphate (615.97 mg, 2.90 mmol), 2-dicyclohexylphosphine-2',4',6'-triisopropyl biphenyl (92.22 mg, 193.45 mol), tri(dibenzylidene acetone) dipalladium (88.57 mg, 96.73 umol). The reaction liquid was heated to 80° C. under nitrogen and stirred for 12 hours. To the reaction liquid was added water (20 mL), extracted with ethyl acetate (30 mL×3). The organic phases were combined, and washed with saturated brine (20 mL), dried over anhydrous sodium sulfate, filtered, and concentrated at reduced pressure. The resulting crude product was purified by silica gel column chromatography (petroleum ether:ethyl acetate=5:1) to give 5-4 (0.88 g, yield 60%).

Step 4: Synthesis of Compound 5-5

Under the condition of room temperature, to a solution of the compound 5-4 (880.00 mg, 1.20 mmol) in dichloromethane (10.00 mL) was added triethyl hydrosilane (279.07 mg, 2.40 mmol) and trifluoroacetic acid (136.83 mg, 1.20 mmol). The reaction liquid was stirred at room temperature for 1 hour. The reaction liquid was concentrated, adjusted to pH 8-9 with a saturated NaHCO$_3$ solution, extracted with ethyl acetate (30 mL×3). The combined organic phases were washed with saturated brine (20 mL), dried over anhydrous sodium sulfate, filtered, and concentrated at reduced pressure. The crude product was purified by silica gel column chromatography (petroleum ether:ethyl acetate=3:1) to give the compound 5-5 (360.00 mg, yield 57.14%). $^1$H NMR (400 MHz, CDOLOFORM-d$_1$) δ 8.39-8.55 (m, 2H), 4.85-4.88 (m, 1H), 4.10-4.20 (m, 2H), 2.95-2.97 (m, 1H), 1.16-2.45 (m, 17H).

Step 5: Synthesis of WX-359, WX-360

Under the condition of room temperature, 5-5 (180.00 mg, 364.73 mol) was dissolved in tetrahydrofuran (2.00 mL), into which was added potassium trimethylsilanolate (233.96 mg, 1.82 mmol). After the addition, the reaction was reacted at 40° C. for 12 hours. The reaction liquid was concentrated, the resulting crude product was adjust to pH 5 with 1N hydrochloric acid solution, which was isolated by a preparative liquid chromatography (column: Boston Green ODS 150*30 5 u; mobile phase: [water(0.1% TFA)-ACN]; B %: 42%-52%, 8 min) to give the compound WX-359 (30.00 mg, yield: 14.19%, retention time=0.808 min) and the compound WX-360 (40.00 mg, yield 18.93%, retention time=0.814 min).

| Compound No. | Compound Structure | MS + 1 | 1HNMR |
|---|---|---|---|
| WX-359 | 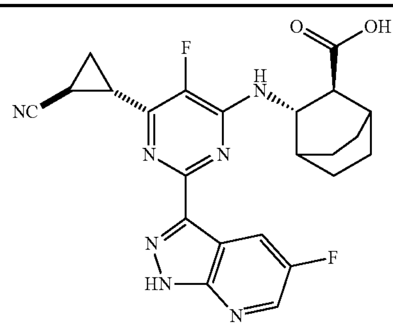 | 466.2 | ¹H NMR (400 MHz, METHANOL-d4) δ 8.47 (s, 2 H), 4.90-4.85 (m, 1 H), 2.94-2.93 (m, 1 H), 2.81-2.79 (m, 1 H), 2.49-2.48 (m, 1 H), 2.12-2.05 (m, 1 H). 1.86-1.49 (m, 11 H). |
| WX-360 | 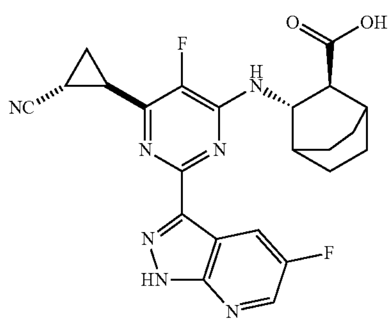 | 466.2 | ¹H NMR (400 MHz, METHANOL-d4) δ 8.58-8.56 (m, 1 H), 8.53-8.51 (m, 1 H), 4.94-4.93 (m, 1 H), 2.96-2.95 (m, 1 H), 2.82-2.80 (m, 1 H), 2.49-2.48 (m, 1 H). 2.13-2.08 (m, 1 H), 1.99-1.51 (m, 11 H). |
Example 6
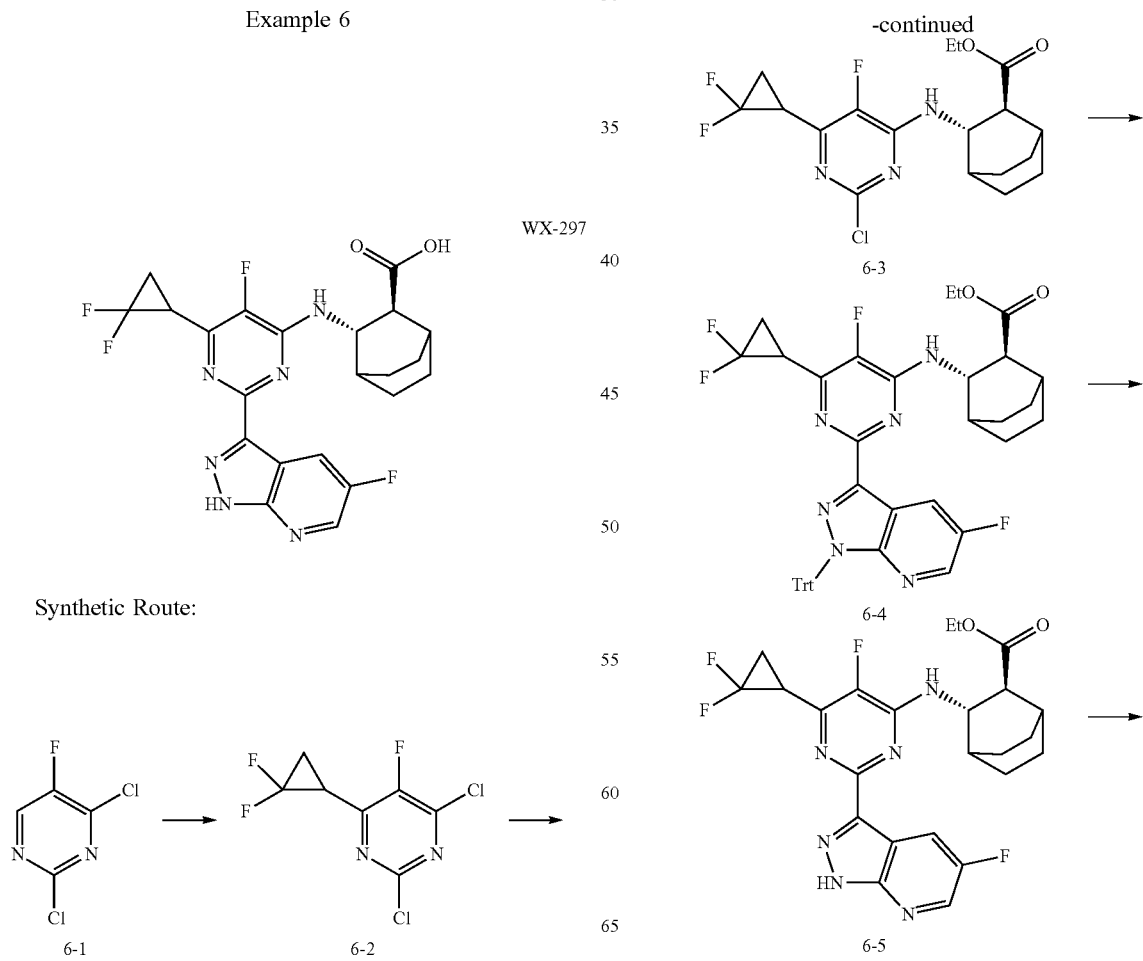

-continued

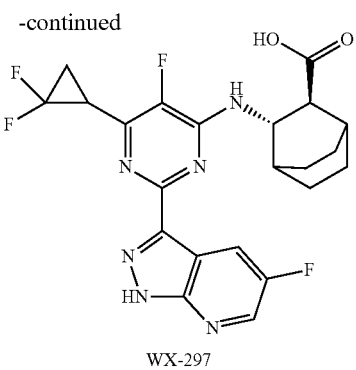

WX-297

Step 1: Synthesis of Compound 6-2

At room temperature, the compound 2,4-dichloro-5-fluoropyrimidine (1 g, 5.99 mmol) was dissolved in acetonitrile (5.00 mL) and water (5.00 mL), into which were added silver nitrate (2.03 g, 11.98 mmol), 2,2-difluorocyclopropyl carboxylic acid (2.19 g, 17.93 mmol), respectively. The reaction liquid was heated to 80° C., into which was then added a solution of ammonium persulfate (2.73 g, 11.98 mmol) in water (1 mL) dropwise. The reaction liquid was reacted at 80° C. overnight, then heated to 100° C. and reacted for 12 hours. The reaction liquid was cooled to room temperature, into which was added ethyl acetate (100 mL). The organic layer was washed with water (30 mL×3) and brine (30 mL) respectively, dried over sodium sulfate, filtered, and concentrated at reduced pressure. The crude product was purified over a silica gel column (petroleum ether:ethyl acetate 1:0 to 10:1) to give the compound 6-2 (121 mg, yield 8.3%). $^1$H NMR (400 MHz, CDOLOFORM-d$_1$) δ 2.98-3.05 (m, 1H), 2.47-2.52 (m, 1H), 1.94-1.98 (m, 1H).

Step 2: Synthesis of Compound 6-3

The compound BB-2 (147 mg, 0.75 mmol) and the compound 6-2 (121 mg, 0.49 mmol) were dissolved in tetrahydrofuran (3.00 mL), into which was added diisopropyl ethylamine (193 mg, 1.49 mmol). The reaction liquid was stirred at 50° C. for 1 hour. The reaction liquid was cooled to room temperature, into which was added ethyl acetate (50 mL). The organic layer was washed with brine (20 mL), dried over sodium sulfate, filtered, and concentrated at reduced pressure. The resulting crude product was purified by flash silica gel column chromatography (petroleum ether:ethyl acetate=20:1 to 10:1) to give the compound 6-3 (132.00 mg, yield 65.6%).

Step 3: Synthesis of Compound 6-4

At room temperature, the compound 6-3 (130 mg, 0.32 mmol) and BB-4 (195 g, 0.39 mmol) were dissolved in 2-methyl tetrahydrofuran (5.00 mL) and water (1.00 mL), into which were added potassium phosphate (136.67 mg, 0.64 mmol), tri(dibenzylidene acetone) dipalladium (14.7 mg, 16 umol) and 2-dicyclohexylphosphine-2',4',6'-triisopropyl biphenyl (30.69 mg, 64.38 umol), respectively. The reaction liquid was reacted at 80° C. for 2 hours. The reaction liquid was cooled to room temperature, into which was added water (30 mL), extracted with ethyl acetate (10 mL×3). The organic phases were combined, dried over anhydrous sodium sulfate, filtered, and concentrated at reduced pressure. The resulting crude product was purified over a flash silica gel column (ethyl acetate/petroleum ether=5%-15%) to give the compound 6-4 (150 mg, yield 62.4%). MS (ESI) m/z: 769.4 (M+23$^+$).

Step 4: Synthesis of Compound 6-5

At room temperature, the compound 6-4 (150.00 mg, 200.86 umol) was dissolved in dichloromethane (3.00 mL), into which was added trifluoroacetic acid (229.02 mg, 2.01 mmol) and triethyl hydrosilane (116.78 mg, 0.16 mmol). The reaction liquid was reacted at room temperature overnight. The reaction liquid was concentrated at reduced pressure. The resulting crude product was purified over a flash silica gel column (ethyl acetate/petroleum ether=10%-30%) to give the compound 6-5 (50.00 mg, yield 50%). MS (ESI) m/z: 505.1 (M+H$^+$).

Step 5: Synthesis of Compound WX-297

At room temperature, the compound 6-5 (50.00 mg, 99.11 umol) was dissolved in dioxane (2.00 mL) and water (1 mL), into which was added sodium hydroxide (19.82 mg, 0.49 mmol). The reaction liquid was reacted at 80° C. for 1 hour. The reaction liquid was concentrated at reduced pressure, into which was then added 1 M HCl to adjust to pH=5, and extracted with ethyl acetate (10 mL×3). The organic phases were combined, dried over anhydrous sodium sulfate, and concentrated at reduced pressure to give WX-297 (30 mg, yield 60.4%). $^1$H NMR (400 MHz, METHANOL-d$_4$) δ 8.57-8.67 (m, 1H), 8.53 (d, J=1.76 Hz, 1H), 4.94 (br d, J=6.78 Hz, 2H), 3.04-3.15 (m, 1H), 2.80 (br d, J=6.78 Hz, 1H), 2.64-2.75 (m, 1H), 2.12 (br s, 1H), 1.78-2.06 (m, 7H), 1.60-1.78 (m, 4H), 1.49-1.60 (m, 2H). MS m/z: 477.2 [M+1]+.

Biological Section
Experiment on Influenza Virus Cytopathic Effect (CPE)

The antiviral activity of the compound against influenza virus (IFV) was assessed by determining the median effective concentration (EC$_{50}$) value of the compound. Experiment on cytopathic effect has been extensively used to determine the protection of the compound to virus infected cells, thus reflecting the antiviral activity of the compound.
Experiment on Influenza Virus CPE MDCK cells (ATCC, Product No. CCL-34) were seeded into a black 384-well cell culture plate in a density of 2,000-3,000 cells per well, then placed in an incubator at 37° C., 5% CO$_2$ and cultivated overnight. The compound was diluted by an Echo555 contactless nano-acoustic pipetting system and added into the cell orifices (3-fold proportion dilution, 8 concentration testing points). Influenza virus A/Weiss/43 (H1N1) strains (ATCC, Product No. VR-96) were then added into cell culture wells at 1-2 90% tissue culture infection dose (TCID90) per well, the final concentration of DMSO in the culture medium was 0.5%. Virus control wells (into which were added DMSO and virus, without the compound) and cell control wells (into which was added DMSO, without the compound and virus) were set. The cell plates were placed in an incubator at 37° C., 5% CO$_2$ and cultivated for 5 days. After cultivation for 5 days, the cell activities were detected using a cell viability detection kit CCK8. The original data was used to calculate the antiviral activities of the compounds.

The antiviral activity of the compound was represented by the inhibition ratio (%) on the cell viral effects caused by the compounds to the virus, the calculation formula of which was as below:

$$\% \text{ inhibition ratio} = \left(\frac{\text{sample value} - \text{average value of virus control}}{\text{average value of cell control} - \text{average value of virus control}}\right) \times 100$$

A nonlinear fitting analysis was performed on the inhibition ratio of the compounds using the GraphPad Prism software, giving $EC_{50}$ values of the compounds. Results of the experiment were shown in Table 1.

TABLE 1

| Compound | $EC_{50}$ (nM) | Compound | $EC_{50}$ (nM) |
|---|---|---|---|
| WX-139 | 0.02 | WX-231 | 0.2 |
| WX-156 | 0.01 | WX-236 | 0.01 |
| WX-160 | 0.5 | WX-240 | 0.03 |
| WX-186 | 0.1 | WX-241 | 0.01 |
| WX-234 | 0.1 | WX-245 | 4 |
| WX-230 | 0.1 | WX-294 | 0.1 |
| WX-247 | 56.6 | WX-295 | 0.013 |
| WX-249 | 0.009 | WX-296 | 1 |
| WX-254 | 0.2 | WX-298 | 6.7 |
| WX-258 | 0.04 | WX-352 | 0.046 |
| WX-260 | 1.1 | WX-261 | 0.018 |
| WX-263 | 1.5 | WX-264 | 0.1 |
| WX-275 | 0.009 | WX-265 | 2.8 |
| WX-276 | 3.6 | WX-269 | 0.019 |
| WX-278 | 2.7 | WX-271 | 0.057 |
| WX-279 | 0.025 | WX-280 | 0.055 |
| WX-281 | 0.026 | WX-216 | 0.013 |
| WX-283 | 0.4 | WX-297 | 0.024 |
| WX-284 | 10 | WX-351 | 0.2 |
| WX-285 | 32 | WX-353 | 0.039 |
| WX-286 | 3.7 | WX-354 | 4.4 |
| WX-288 | 2.3 | WX-355 | 0.04 |
| WX-289 | 0.1 | WX-358 | 0.6 |
| WX-290 | 0.041 | WX-359 | 0.09 |
| WX-293 | 8 | WX-360 | 0.2 |
|  |  | WX-274 | 0.1 |

Results and Disscussion: The present compounds have exhibited positive effects in the tests of inhibiting the replication of influenza virus on the cellular level.

Experimental Example 2: Study of In Vivo Pharmacodynamics

The pharmacodynamics of the compounds in mouse infection models of influenza A virus H1N1 were assessed.

Mice were infected with influenza Avirus H1N1 (Virapur Co., Product No.: F1003A) by nasal instillation. After 36 hours post-infection, they were treated with the compounds by oral administration for 7 days, twice a day. Based on the observation on the mice weight changes and their survival rate, anti-influenza A virus H1N1 effects of the compounds in such model were assessed.

6-7 weeks old, female BALB/c mice of SPF grade (Shanghai Lingchang Biotechnology Co., Ltd.) were chosen to be used in the experiments. After arriving at BSL-2 animal houses, mice were acclimatized for at least 3 days prior to experiment. The day of infection was set as day 0 of the experiment. Mice were anesthetized by intraperitoneal injection of pentobarbital sodium (75 mg/kg, 10 ml/kg), which animals were infected with H1N1 A/WSN/33 virus by nasal instillation after entering the state of deep anesthesia, with the infection volume of 50 ul. From day 1 to day 7, the compounds to be tested were given 10 mg/kg (dosing volume of 10 ml/kg) every day by oral administration, twice a day. The first dosing time was 36 hours after infection. The states of mice were observed every day, and their weight and survival rate were recorded. On day 14, all surviving animals were euthanized.

The survival rate and the weight losing rate of animals were detected, as shown in the table below: the compound WX-231 may achieve protecting the weight losing rate of animals at 12.9%, the survival rate at 100% on day 9, the compound WX-216 may achieve protecting the weight losing rate of animals at 4.8%, the survival rate at 100% on day 9, WX-279 may achieve protecting the weight losing rate of animals at 28.7%, the survival rate at 100% on day 9, WX-290 may achieve protecting the weight losing rate of animals at 27.6%, the survival rate at 40% on day 9, WX-297 may achieve protecting the weight losing rate of animals at 27.3%, the survival rate at 100% on day 9, WX-351 may achieve protecting the weight losing rate of animals at 35.3%, the survival rate at 100% on day 9. Experimental results were seen in Table-2.

TABLE 2

| Compound | Weight Losing Rate (day 9) | Survival Rate (percentages) |
|---|---|---|
| WX-231 | 12.9% | 100% |
| WX-216 | 4.8% | 100% |
| WX-279 | 28.7% | 100% |
| WX-290 | 27.6% | 40% |
| WX-297 | 27.3% | 100% |
| WX-351 | 35.3% | 20% |

What is claimed is:

1. A method for treating influenza caused by influenza A, comprising administering a compound of formula (I) or a pharmaceutically acceptable salt thereof to a subject in need thereof:

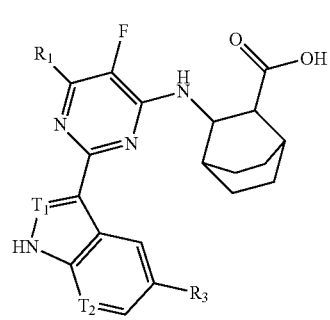

(I)

wherein
- $R_1$ is selected from $C_{1-6}$ alkylthio, 5-6 membered heteroaryl, $C_{2-6}$ alkynyl and $C_{3-6}$ cycloalkyl, each of which is optionally substituted with 1, 2 or 3 R or R';
- $T_1$ is N;
- $T_2$ is N;
- $R_3$ is selected from H, halogen, CN, $NH_2$, OH, or from $C_{1-6}$ alkyl which is optionally substituted with 1, 2 or 3 R or R';
- R is selected from halogen, OH, $NH_2$, CN, COOH,

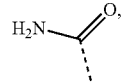

or from C$_{1-6}$ alkyl, C$_{1-6}$ heteroalkyl, C$_{3-6}$ cycloalkyl, 3-6 membered heterocycloalkyl, 3-6 membered heterocycloalkyl-C(=O)—, or 3-6 membered heterocycloalkyl-(CH$_2$)$_{1-3}$—, each of which is optionally substituted with 1, 2 or 3 R';

R' is selected from F, Cl, Br, I, CN, OH, NH$_2$, COOH, Me, NHCH$_3$, N(CH$_3$)$_2$,

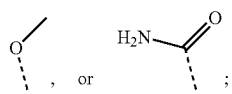

"hetero-" in the 5-6 membered heteroaryl, C$_{1-6}$ heteroalkyl, 3-6 membered heterocycloalkyl is selected from ~N=, —S—, —O—, or —NH—;

in any one of the aforesaid cases, the number of heteroatom(s) or heteroatomic group(s) is each independently selected from 1, 2 or 3.

2. The method according to claim 1, wherein, R is selected from F, Cl, Br, I, OH, NH$_2$, CN, COOH,

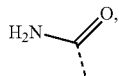

or from C$_{1-3}$ alkyl, C$_{1-3}$ heteroalkyl, C$_{3-6}$ cycloalkyl, 3-6 membered heterocycloalkyl, 3-6 membered heterocycloalkyl-C(=O)—, or 3-6 membered heterocycloalkyl-CH$_2$—, each of which is optionally substituted with 1, 2 or 3 R'.

3. The method according to claim 1, wherein, R is selected from F, Cl, Br, I, OH, NH$_2$, CN, COOH,

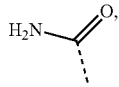

or from Me, Et, C$_{1-3}$ alkylthio, C$_{3-6}$ cycloalkyl, azetidinyl, pyrrolidinyl, piperazinyl, morpholinyl, piperazinyl-C(=O)—, morpholinyl-C(=O)—, pyrrolidinyl-C(=O)—, piperazinyl-CH$_2$—, morpholinyl-CH$_2$—, or pyrrolidinyl-CH$_2$—, each of which is optionally substituted with 1, 2 or 3 R'.

4. The method according to claim 3, wherein, R is selected from F, Cl, Br, I, OH, NH$_2$, CN, COOH,

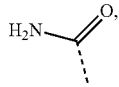

or from Me, Et,

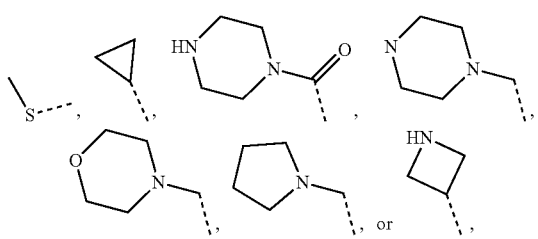

each of which is optionally substituted with 1, 2 or 3 R'.

5. The method according to claim 4, wherein, R is selected from F, Cl, Br, I, OH, NH$_2$, Me, Et, CN, COOH,

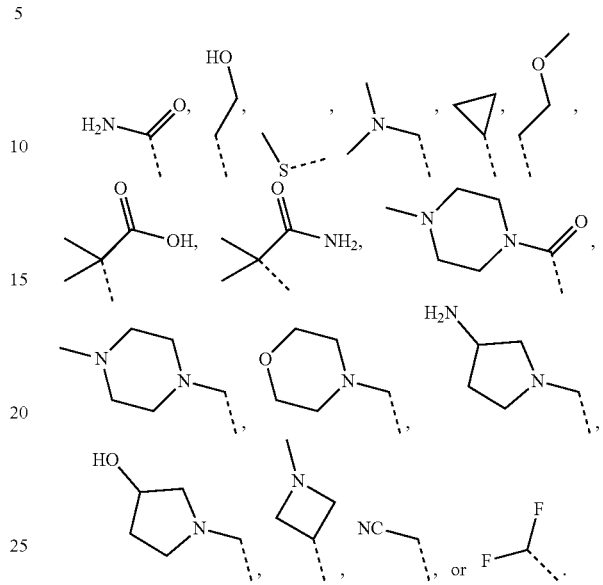

6. The method according to claim 1, wherein, R$_1$ is selected from C$_{1-3}$ alkylthio, C$_{2-4}$ alkynyl, or C$_{3-5}$ cycloalkyl, each of which is optionally substituted with 1, 2 or 3 R or R'.

7. The method according to claim 6, wherein, R$_1$ is selected from

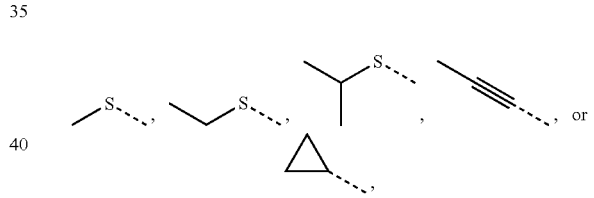

each of which is optionally substituted with 1, 2 or 3 R or R'.

8. The method according to claim 7, wherein, R$_1$ is selected from

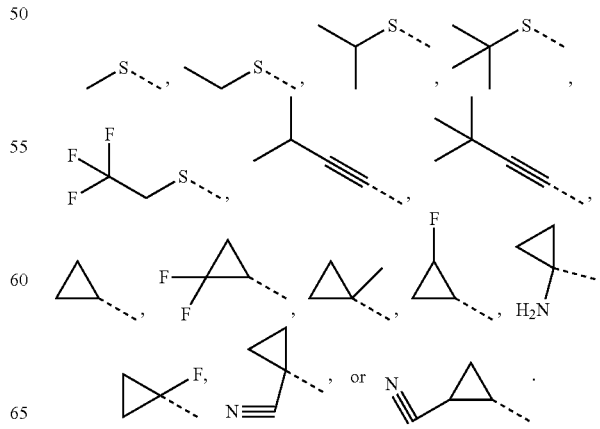

9. The method according to claim 1, wherein, $R_1$ is selected from pyridyl, pyrazolyl, imidazolyl, thienyl, oxazolyl, or isoxazolyl, each of which is optionally substituted with 1, 2 or 3 R or R'.

10. The method according to claim 9, wherein, $R_1$ is selected from

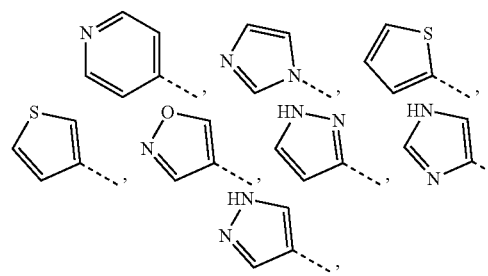

or each of which is optionally substituted with 1, 2 or 3 R or R'.

11. The method according to claim 10, wherein, $R_1$ is selected from

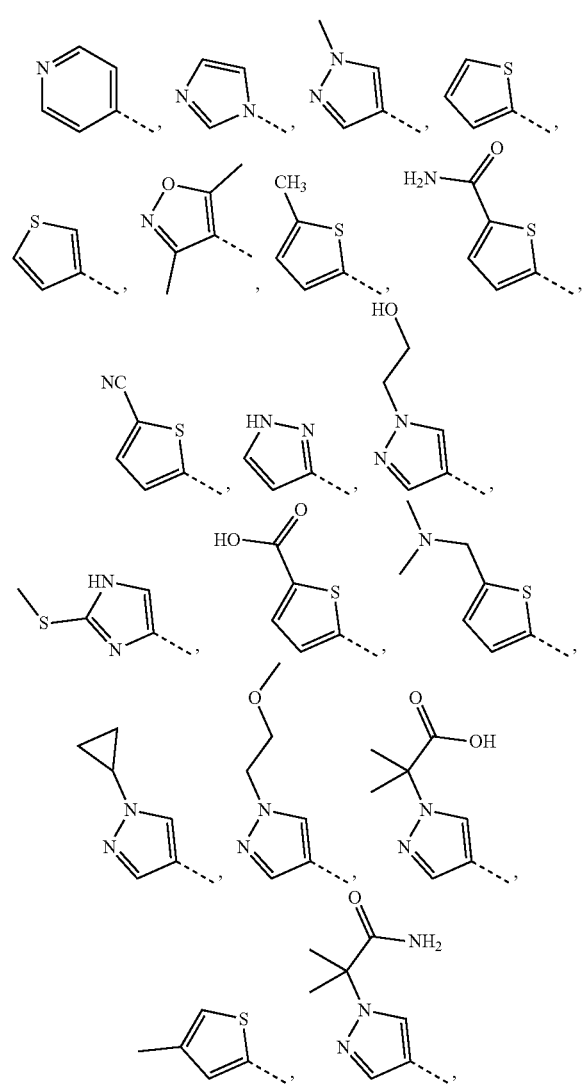

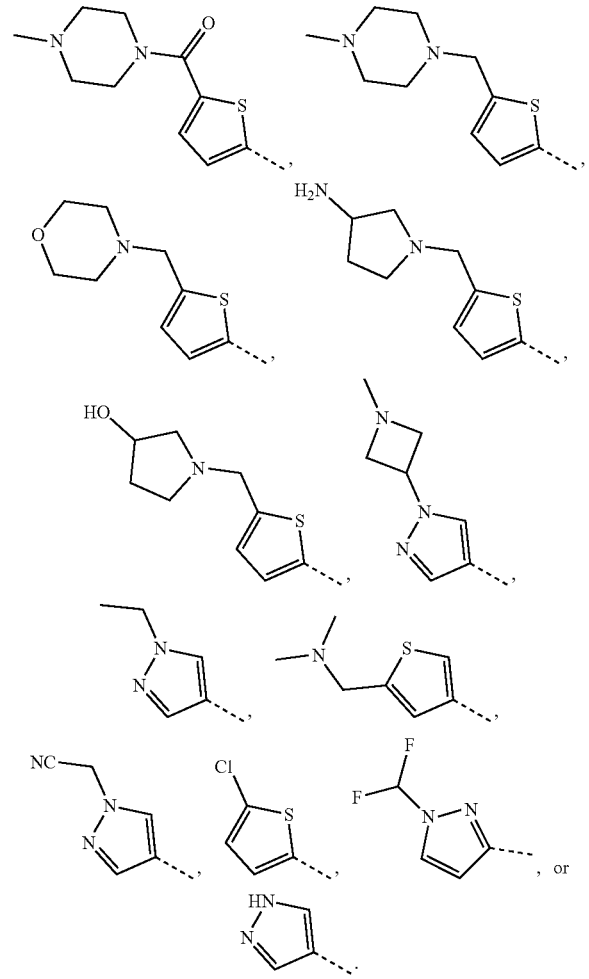

12. The method according to claim 1, wherein, $R_1$ is selected from

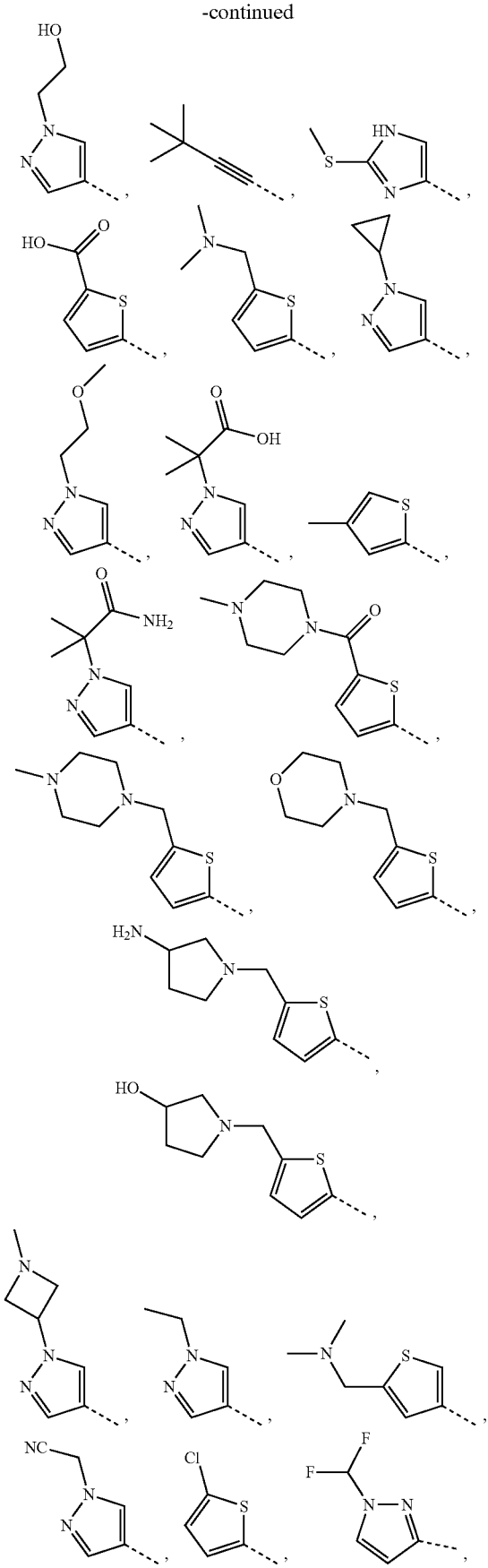

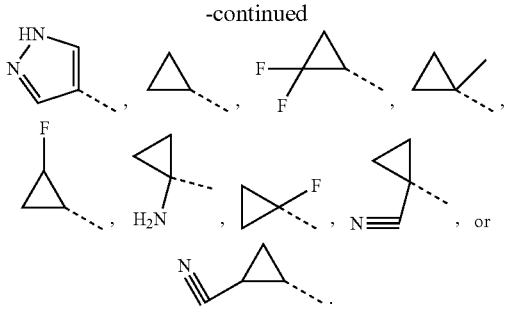

13. The method according to claim 1, wherein, $R_3$ is selected from H, halogen, CN, $NH_2$, OH, or from $C_{1-3}$ alkyl which is optionally substituted with 1, 2 or 3 R or R'.

14. The method according to claim 13, wherein, $R_3$ is selected from H, F, Cl, Br, I, CN, $NH_2$, OH, or from Me and Et, each of which is optionally substituted with 1, 2 or 3 R or R'.

15. The method according to claim 14, wherein, $R_3$ is selected from H, F, Cl, Br, I, CN, $NH_2$, OH, Me, Et, or $CF_3$.

16. A method for treating influenza caused by influenza A, comprising administering any one of the following compounds or the pharmaceutically acceptable salt thereof to a subject in need thereof.

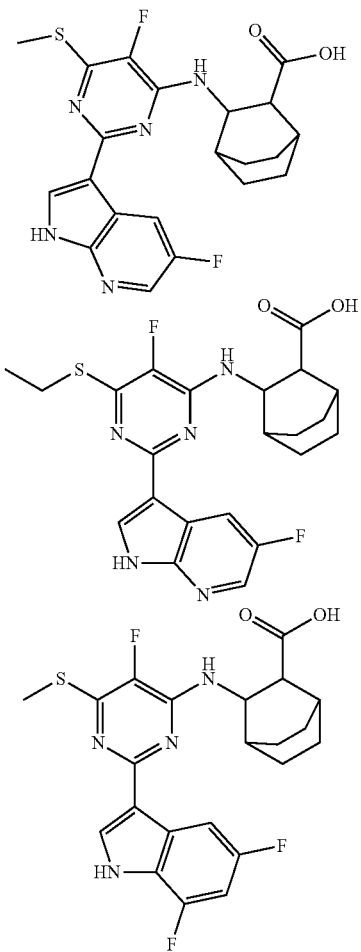

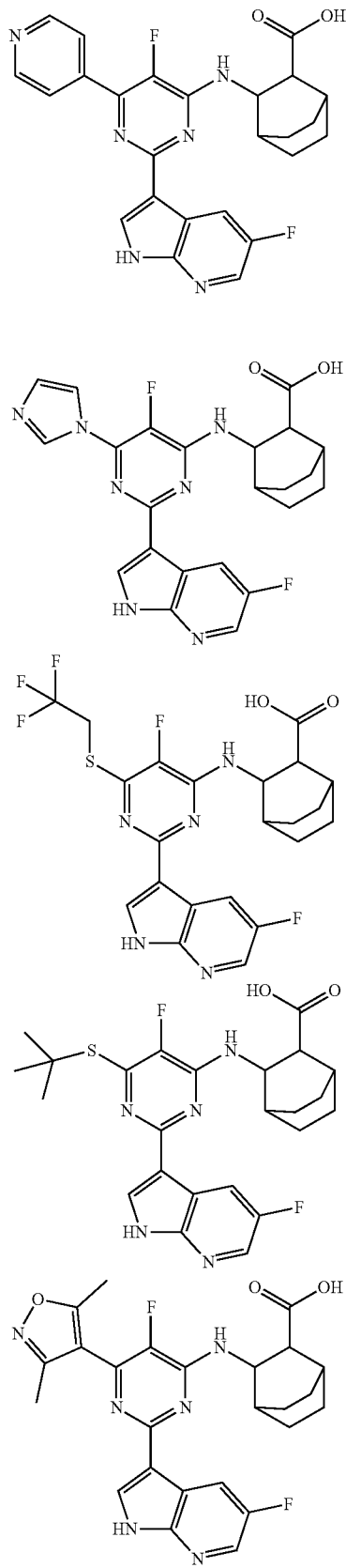
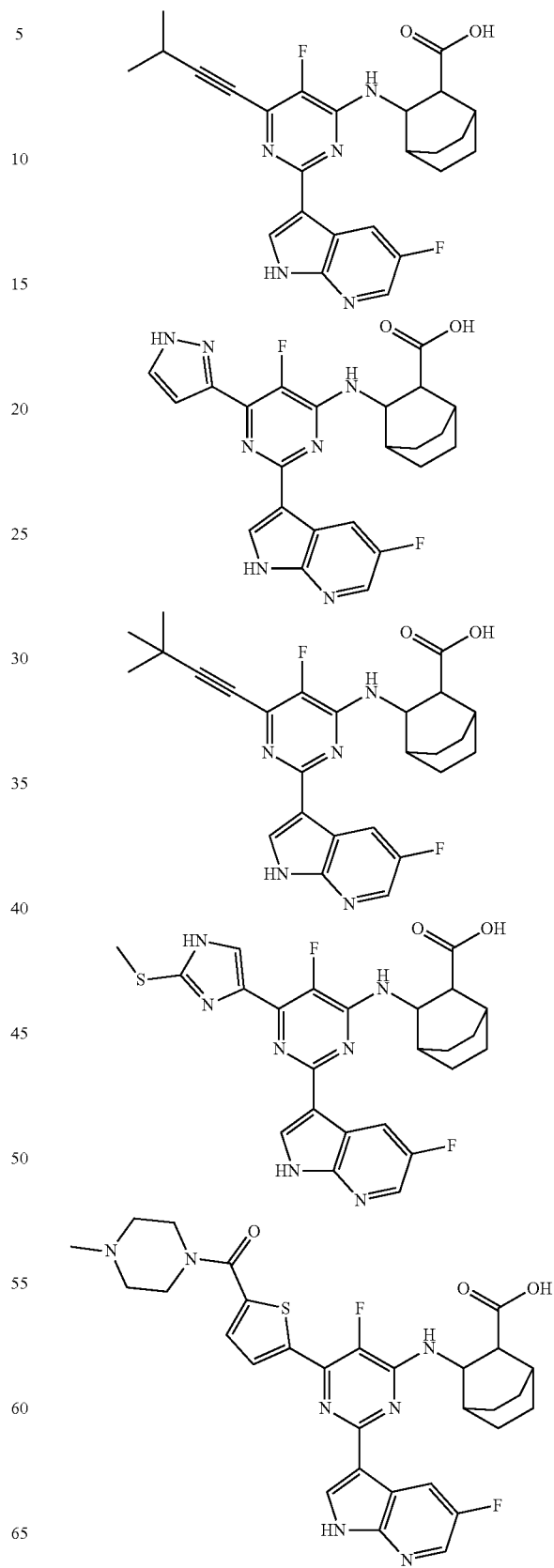

105
-continued
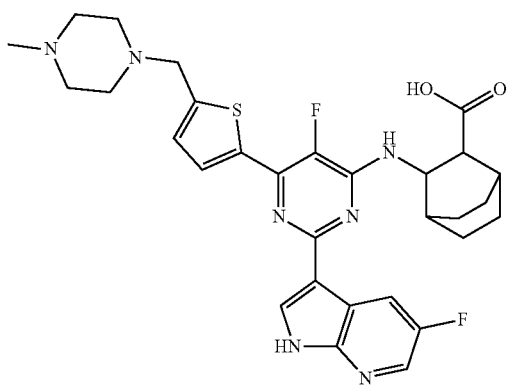
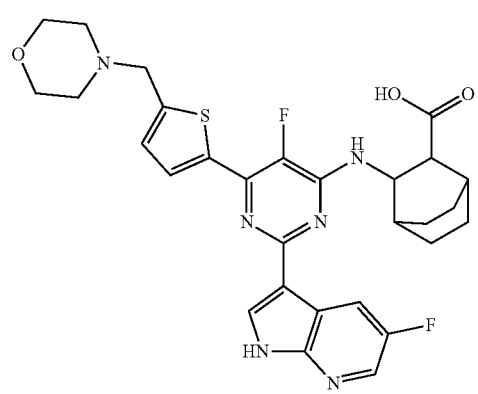
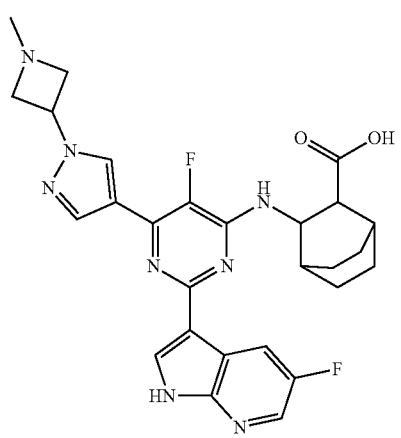
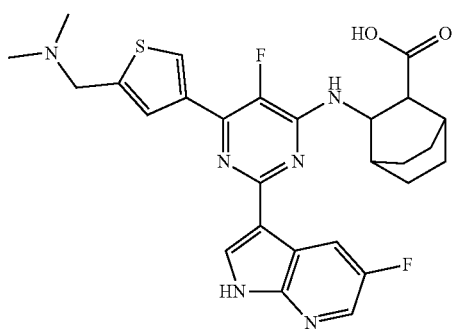
106
-continued
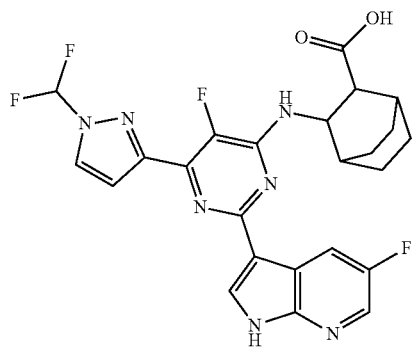
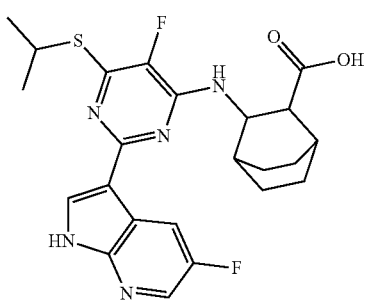
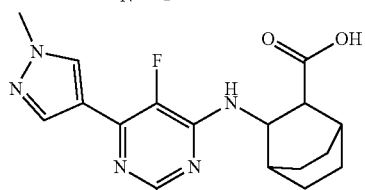
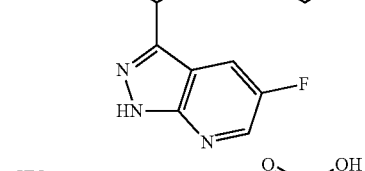
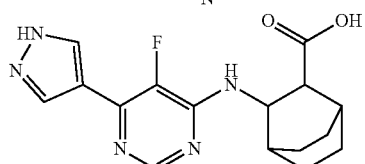
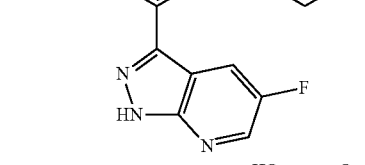
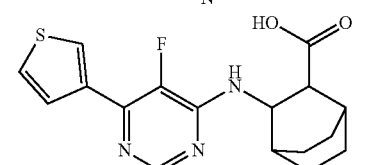
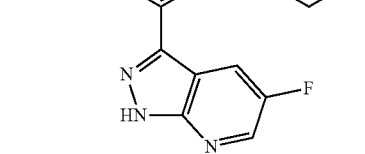

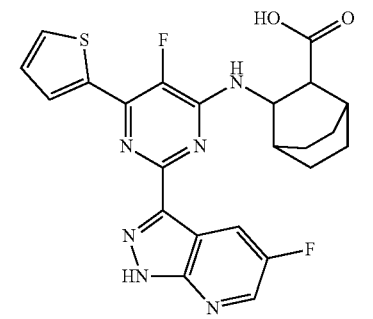
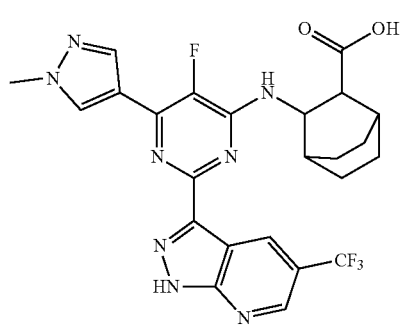
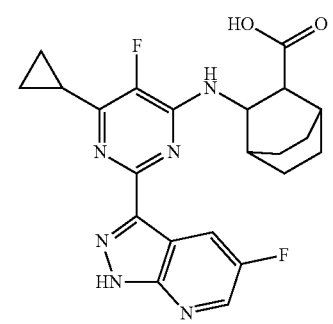
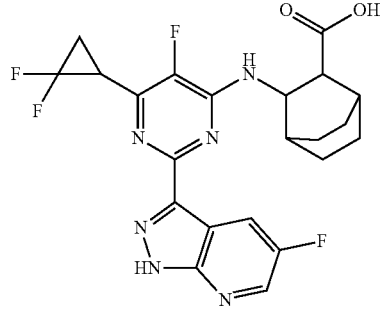
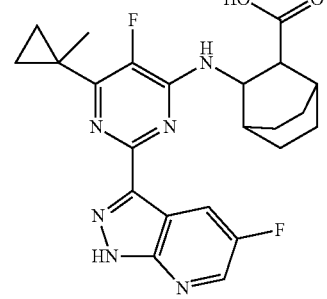
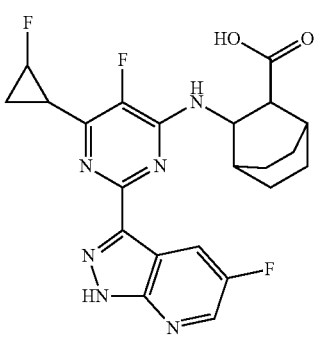
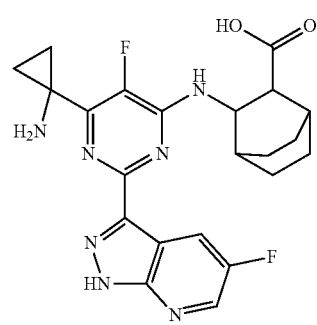
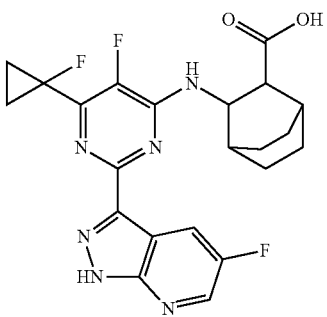
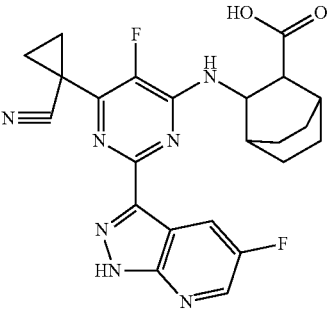
or

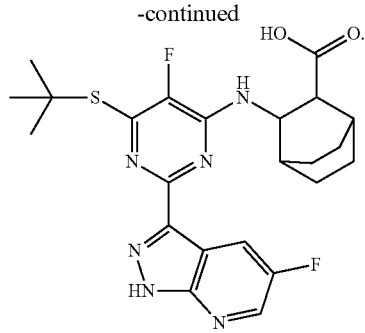
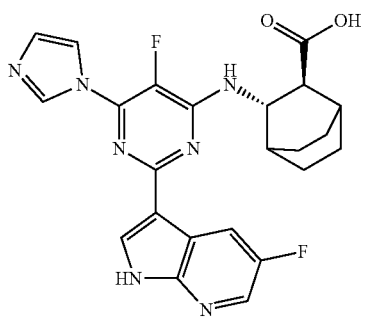
17. The method according to claim 16, wherein, the compound is selected from
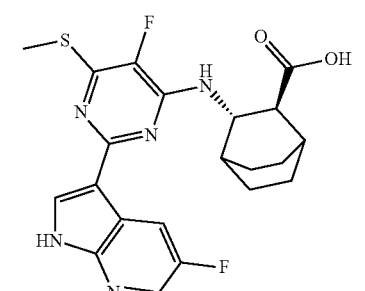
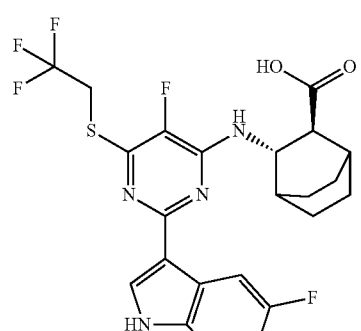
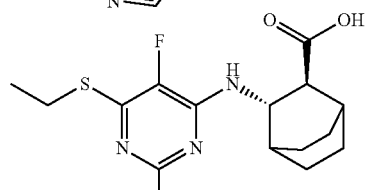
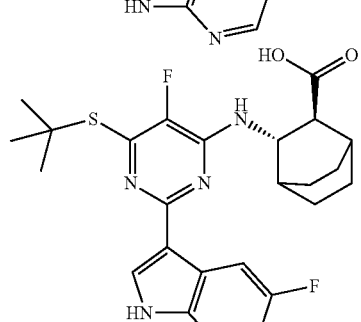
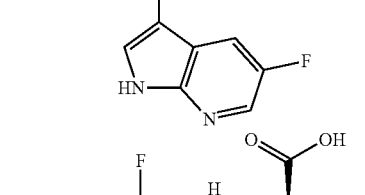
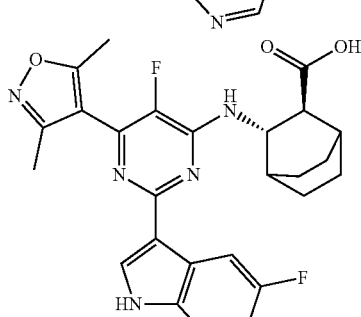
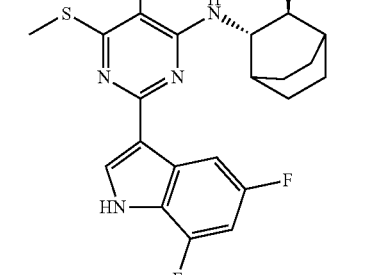
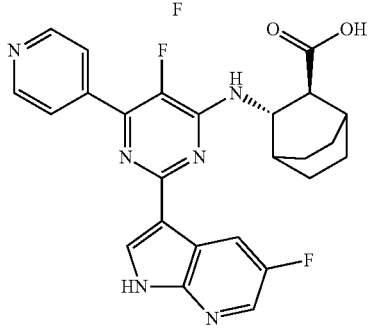
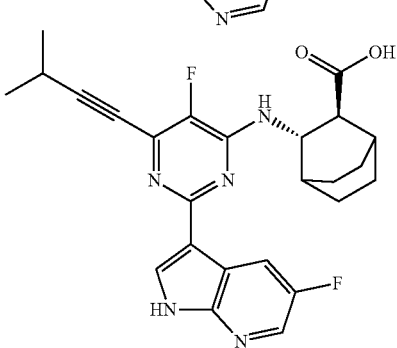

111
-continued
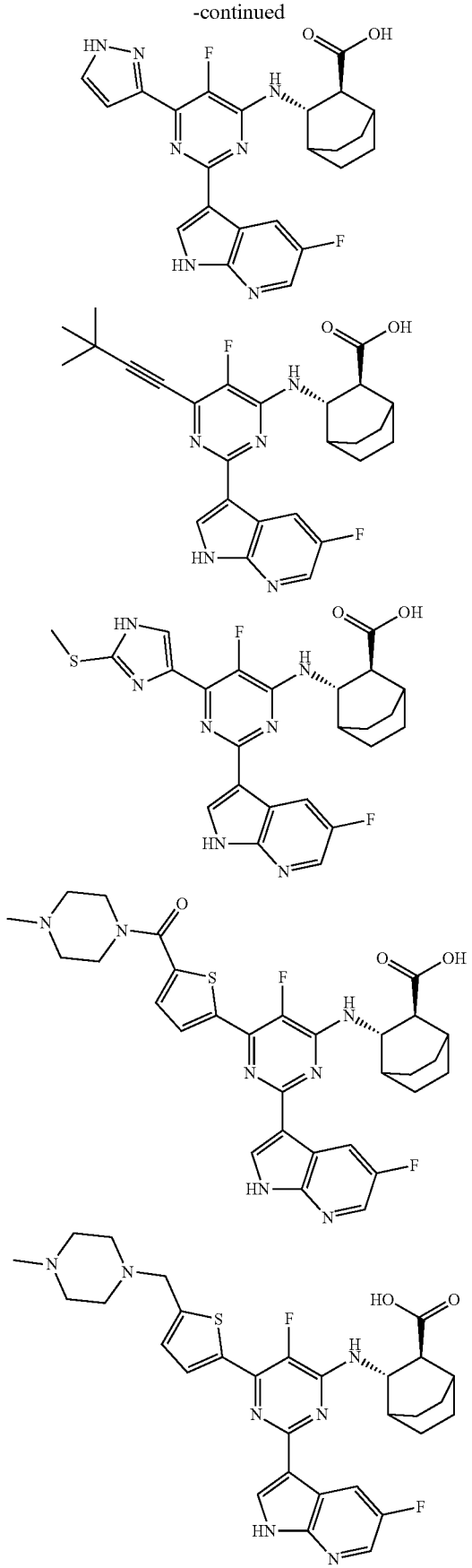
112
-continued
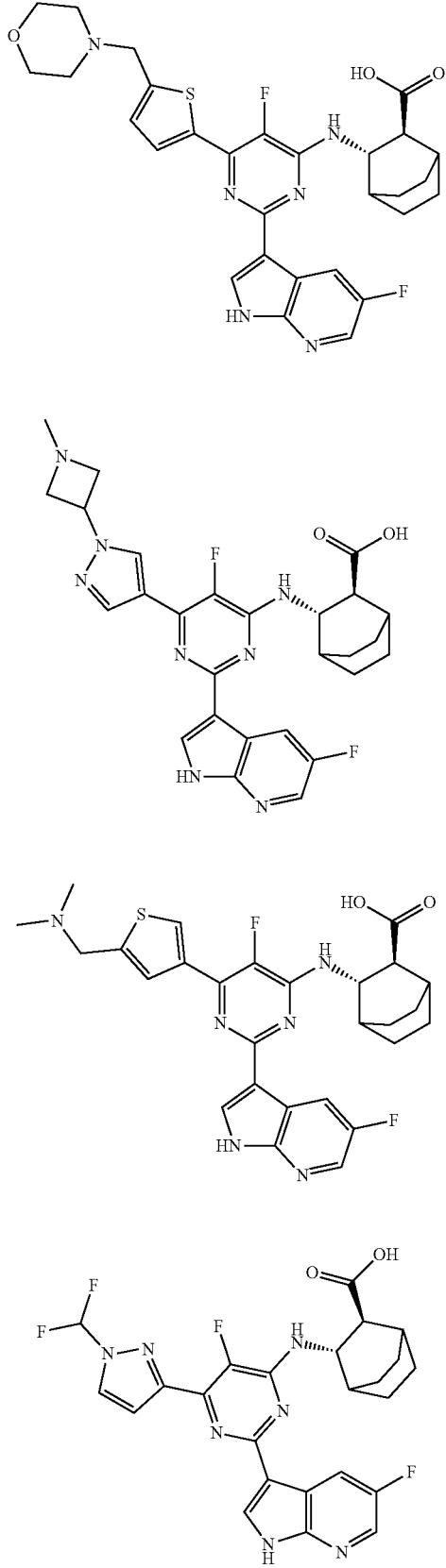

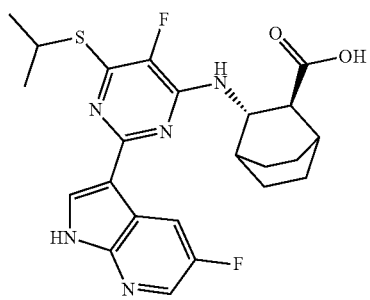
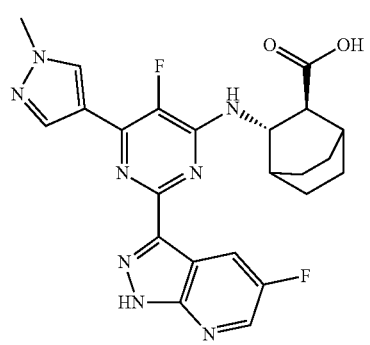
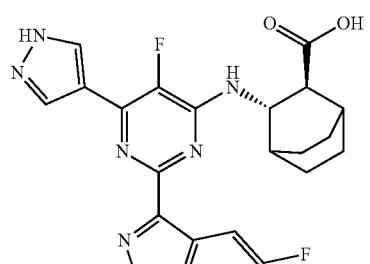
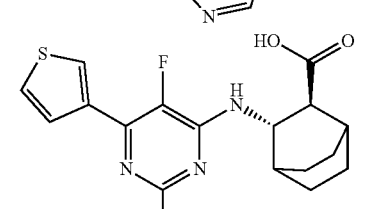
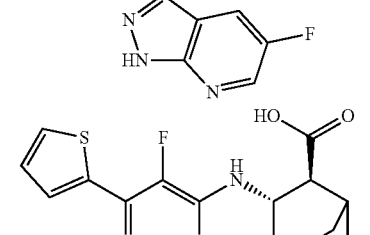
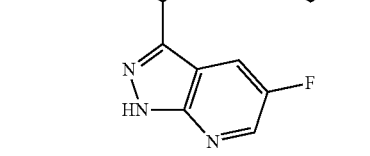
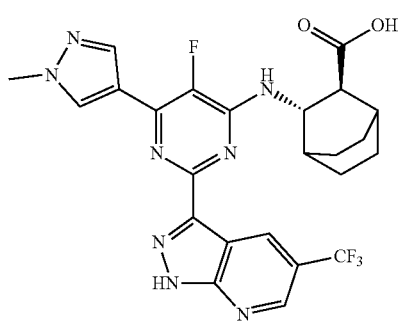
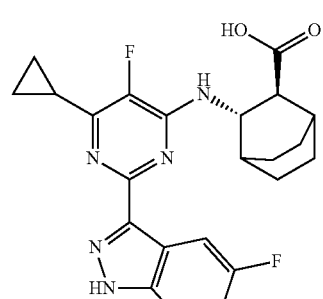
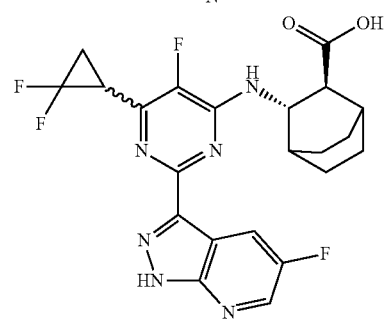
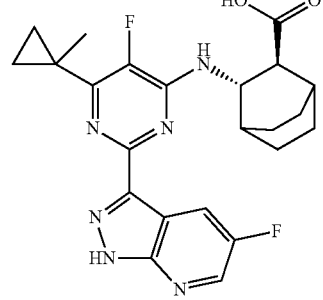
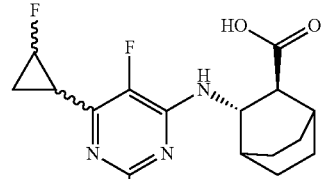
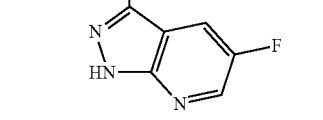

115
-continued
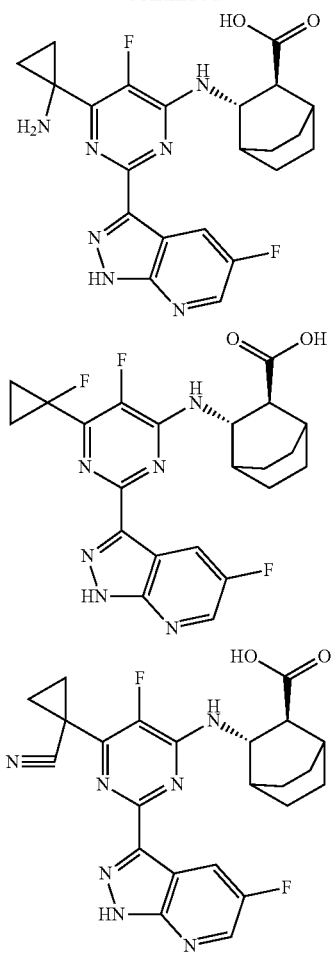
116
-continued
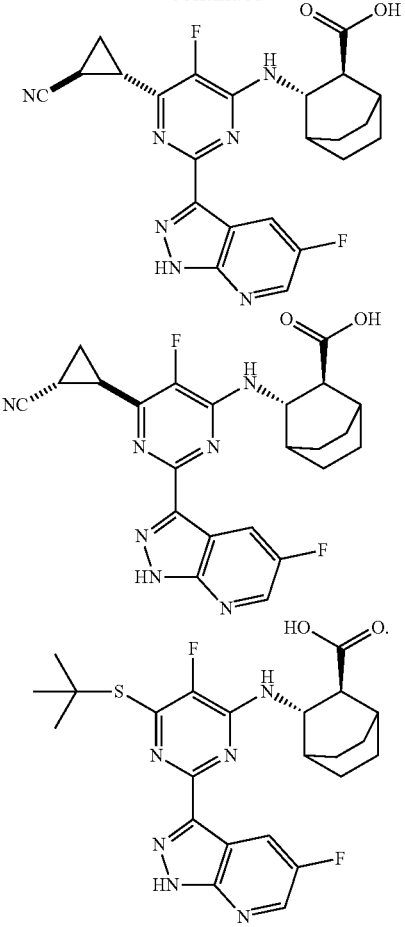
or
* * * * *